US008357518B2

(12) United States Patent
Han et al.

(10) Patent No.: US 8,357,518 B2
(45) Date of Patent: Jan. 22, 2013

(54) THERMOSTABLE ENZYMES FOR THE HYDROLYSIS OF MANNAN-CONTAINING POLYSACCHARIDES

(75) Inventors: Yejun Han, Urbana, IL (US); Dylan Dodd, Champaign, IL (US); Satish Nair, Champaign, IL (US); Roderick I. Mackie, Urbana, IL (US); Isaac K. O. Cann, Savoy, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 13/114,907

(22) Filed: May 24, 2011

(65) Prior Publication Data

US 2011/0294166 A1    Dec. 1, 2011

Related U.S. Application Data

(60) Provisional application No. 61/349,789, filed on May 28, 2010.

(51) Int. Cl.
| C12P 19/14 | (2006.01) |
| C12P 19/04 | (2006.01) |
| C12P 7/06  | (2006.01) |
| C12N 9/26  | (2006.01) |
| C11D 3/00  | (2006.01) |
| D06P 3/60  | (2006.01) |

(52) U.S. Cl. .............. 435/99; 435/201; 435/161; 8/137; 8/402

(58) Field of Classification Search .................. None
See application file for complete search history.

(56) References Cited

U.S. PATENT DOCUMENTS

2008/0064064 A1   3/2008   Kensch et al.

OTHER PUBLICATIONS

Aziz et al., "The RAST Server: Rapid Annotations Using Subsystems Technology", BMC Genomics, vol. 9, No. 75, 2008, pp. 1-15.
Bae et al., "Molecular Basis for the Selectivity and Specificity of Ligand Recognition by the Family 16 Carbohydrate-binding Modules from *Thermoanaerobacterium polysaccharolyticum* ManA", The Journal of Biological Chemistry, vol. 283, No. 18, May 2, 2008, pp. 12415-12425.
Cann et al., "Characterization of Two Novel Saccharolytic, Anaerobic Thermophiles, *Thermoanaerobacterium polysaccharolyticum* Sp. Nov. and *Thermoanaerobacterium zeae* Sp. Nov., and Emendation of the Genus *Thermoanaerobacterium*", International Journal of Systematic and Evolutionary Microbiology, vol. 51, 2001, pp. 293-302.
Cann et al., "Molecular Cloning, Sequencing, and Expression of a Novel Multidomain Mannanase Gene from *Thermoanaerobacterium polysaccharolyticum*", Journal of Bacteriology, vol. 181, No. 5, Mar. 1999, pp. 1643-1651.
Cartmell et al., "The *Cellvibrio japonicus* Mannanase CjMan26C Displays a Unique Exo-Mode of Action That Is Conferred by Subtle Changes to the Distal Region of the Active Site", The Journal of Biological Chemistry, vol. 283, No. 49, Dec. 5, 2008, pp. 34403-34413.
Charnock et al., "The Topology of the Substrate Binding Clefts of Glycosyl Hydrolase Family 10 Xylanases Are Not Conserved", The Journal of Biological Chemistry, vol. 273, No. 48, 1998, pp. 32187-32199.
Davies et al., "Recent Structural Insights into the Expanding World of Carbohydrate-Active Enzymes", Current Opinion in Structural Biology, vol. 15, 2005, pp. 637-645.
Dodd et al., Biochemical Analysis of a Beta-D-Xylosidase and a Bifunctional Xylanase-Ferulic Acid Esterase from a Xylanolytic Gene Cluster in *Prevotella ruminicola* 23, Journal of Bacteriology, vol. 191, No. 10, May 2009, pp. 3328-3338.
Dodd et al., "Enzymatic Deconstruction of Xylan for Biofuel Production", GCB Bioenergy, vol. 1, 2009, pp. 2-17.
Dominguez et al., "A Common Protein Fold and Similar Active Site in Two Distinct Families of Beta-Glycanases", Nature Structural Biology, vol. 2, No. 7, Jul. 1995, pp. 569-576.
Hilge et al., "High-Resolution Native and Complex Structures of Thermostable Beta-Mannanase from *Thermomonospora fusca*—Substrate Specificity in Glycosyl Hydrolase Family 5", Structure, vol. 6, No. 11, 1998, pp. 1433-1444.
King et al., "Purification and Characterization of a Thermostable Alpha-Galactosidase from *Thermoanaerobacterium polysaccharolyticum*", J. Agric. Food Chem., vol. 50, No. 20, 2002, pp. 5676-5682.
Kittur et al., "Fusion of Family 2b Carbohydrate-Binding Module Increases the Catalytic Activity of a Xylanase from *Thermotoga maritima* to Soluble Xylan", FEBS Letters, vol. 549, 2003, pp. 147-151.
Kurokawa et al., "*Clostridium thermocellum* Cellulase CelT, a Family 9 Endoglucanase without an Lg-Like Domain or Family 3c Carbohydrate-Binding Module", Appl Microbiol Biotechnol, vol. 59, 2002, pp. 455-461.
Lee, Y. C., "Carbohydrate Analyses with High-Performance Anion-Exchange Chromatography", Journal of Chromatography A, vol. 720, 1996, pp. 137-149.
Lee e tal., "Description of *Caldanaerobius fijiensis* Gen. Nov., Sp. Nov., An Inulin-Degrading, Ethanol-Producing, Thermophilic Bacterium from a Fijian Hot Spring Sediment, and Reclassification of *Thermoanaerobacterium polysaccharolyticum* and *Thermoanaerobacterium zeae* as *Caldanaerobius polysaccharolyticus* Comb. Nov. and *Caldanaerobius zeae* Comb. Nov.", International Journal of Systematic and Evolutionary Microbiology, vol. 58, 2008, pp. 666-670.
Lobley et al., "DICHROWEB: An Interactive Website for the Analysis of Protein Secondary Structure from Circular Dichroism Spectra", Bioinformatics Application Note, vol. 18, No. 1, 2002, pp. 211-212.
Matsui et al., "Subsite Structure of *Saccharomycopsis* Alpha-Amylase Secreted from *Saccharomyces cerevisiae*", J Biochem., vol. 109, 1991, pp. 566-569.

(Continued)

*Primary Examiner* — David J Steadman
*Assistant Examiner* — Paul Holland
(74) *Attorney, Agent, or Firm* — Morrison & Foerster LLP

(57) ABSTRACT

The present disclosure relates to hydrolysis of mannan-containing poly- or oligo-saccharides by use of a polypeptide having endo-β-mannanase activity. In particular the present disclosure relates to compositions comprising a bacterial endo-β-mannanase, polynucleotides encoding the endo-β-mannanase, and methods of use thereof.

16 Claims, 15 Drawing Sheets

OTHER PUBLICATIONS

Matuschek et al. ", Pullulanase of *Thermoanaerobacterium thermosulfurigenes* EM1 (*Clostridium thermosulfurogenes*): Molecular Analysis of the Gene, Composite Structure of the Enzyme, and a Common Model for Its Attachment to the Cell Surface", Journal of Bacteriology, vol. 176, No. 11, Jun. 1994, pp. 3295-3302.

Moreira et al., "An Overview of Mannan structure and Mannan-Degrading Enzyme Systems", Appl Microbiol Biotechnol, vol. 79, 2008, pp. 165-178.

Navas et al., "Site-Directed Mutagenesis of Conserved Residues of *Clostridzum thermocellum* Endoglucanase Celc", Biochemical and Biophysical Research Communications, vol. 189, No. 2, Dec. 15, 1992, pp. 807-812.

Shoseyov et al., "Carbohydrate Binding Modules: Biochemical Properties and Novel Applications", Microbiology and Molecular Biology Reviews, vol. 70, No. 2, Jun. 2006, pp. 283-295.

Teather et al., "Use of Congo Red-Polysaccharide Interactions in Enumeration and Characterization of Cellulolytic Bacteria from the Bovine Rumen", Applied and Environmental Microbiology, vol. 43, No. 4, Apr. 1982, pp. 777-780.

Vaaje-Kolstad et al., "The Non-Catalytic Chitin-Binding Protein CBP21 from *Serratia marcescens* Is Essential for Chitin Degradation", The Journal of Biological Chemistry, vol. 280, No. 31, 2005, pp. 28492-28497.

Weitzhandler et al., "Eliminating Monosaccharide Peak Tailing in High pH Anion-Exchange Chromatography with Pulsed Amperometric Detection", Analytical Biochemistry, vol. 241, 1996, pp. 135-136.

Yeoman et al., "Thermostable Enzymes as Biocatalysts in the Biofuel Industry", Advances in Applied Microbiology, vol. 70, 2010, pp. 1-55.

SEQUENCE LISTING

```
<160> NUMBER OF SEQ ID NOS: 55

<210> SEQ ID NO 1
<211> LENGTH: 31
<212> TYPE: PRT
<213> ORGANISM: Artificial Sequence
<220> FEATURE:
<223> OTHER INFORMATION: Synthetic Construct

<400> SEQUENCE: 1

Leu Asp Gln Ala Ile Ala Trp Phe Lys Glu Leu Ala Ala Lys Tyr Lys
1               5                   10                  15

Asp Asn Pro Tyr Val Trp Phe Asn Thr Met Asn Glu Pro Gly Ser
            20                  25                  30

<210> SEQ ID NO 2
<211> LENGTH: 31
<212> TYPE: PRT
<213> ORGANISM: Artificial Sequence
<220> FEATURE:
<223> OTHER INFORMATION: Synthetic Construct

<400> SEQUENCE: 2

Tyr Ile Asp Arg Ala Asn Ala Lys Gly Leu Tyr Val Phe Met Glu Glu
1               5                   10                  15

Tyr Gly Lys Asp Tyr Ser Asp Ala Ala Lys Glu Gly Val Lys Ser
            20                  25                  30

<210> SEQ ID NO 3
<211> LENGTH: 31
<212> TYPE: PRT
<213> ORGANISM: Artificial Sequence
<220> FEATURE:
<223> OTHER INFORMATION: Synthetic Construct

<400> SEQUENCE: 3
```

Asp Gln Ala Val Asp Tyr Trp Ile Glu Leu Lys Ser Val Leu Gln Gly
1               5                   10                  15

Glu Glu Asp Tyr Val Leu Ile Asn Ile Gly Asn Glu Pro Tyr Gly
            20                  25                  30

<210> SEQ ID NO 4
<211> LENGTH: 31
<212> TYPE: PRT
<213> ORGANISM: Artificial Sequence
<220> FEATURE:
<223> OTHER INFORMATION: Synthetic Construct

<400> SEQUENCE: 4

Tyr Leu Glu His Phe Val Asn Ala Gly Leu Pro Leu Ile Ile Gly Glu
1               5                   10                  15

Phe Gly His Asp His Ser Asp Gly Asn Pro Asp Glu Asp Thr Ile
            20                  25                  30

<210> SEQ ID NO 5
<211> LENGTH: 31
<212> TYPE: PRT
<213> ORGANISM: Artificial Sequence
<220> FEATURE:
<223> OTHER INFORMATION: Synthetic Construct

<400> SEQUENCE: 5

Val Asp Lys Ala Ile Glu Phe Phe Thr Lys Ile Ala Lys Ala Tyr Gly
1               5                   10                  15

Ser Tyr Pro His Val Leu Tyr Glu Thr Phe Asn Glu Pro Leu Gln
            20                  25                  30

<210> SEQ ID NO 6
<211> LENGTH: 31
<212> TYPE: PRT
<213> ORGANISM: Artificial Sequence
<220> FEATURE:
<223> OTHER INFORMATION: Synthetic Construct

<400> SEQUENCE: 6

Lys Leu Gln Thr Ala Ile Asn Asn Gly Leu Pro Ile Phe Val Thr Glu
1               5                   10                  15

Tyr Gly Thr Cys Ser Ala Asp Gly Asn Gly Asn Ile Asp Thr Asn
            20                  25                  30

<210> SEQ ID NO 7
<211> LENGTH: 31
<212> TYPE: PRT
<213> ORGANISM: Artificial Sequence
<220> FEATURE:
<223> OTHER INFORMATION: Synthetic Construct

<400> SEQUENCE: 7

Ala Thr Gln Ala Glu Ser Phe Phe Lys Ser Tyr Ala Ala Lys Tyr Lys
1               5                   10                  15

Ser Tyr Gly Asn Val Ile Phe Glu Val Cys Asn Glu Pro Thr Gly
            20                  25                  30

<210> SEQ ID NO 8
<211> LENGTH: 31
<212> TYPE: PRT
<213> ORGANISM: Artificial Sequence
<220> FEATURE:
<223> OTHER INFORMATION: Synthetic Construct

<400> SEQUENCE: 8

Lys Leu Gln Thr Ala Leu Asn Ala Gly Thr Pro Val Phe Val Ser Glu
1               5                   10                  15

Phe Gly Leu Cys Asp Ala Ser Gly Asn Gly Ile Asp Gln Asp
            20                  25                  30

<210> SEQ ID NO 9
<211> LENGTH: 31
<212> TYPE: PRT
<213> ORGANISM: Artificial Sequence
<220> FEATURE:
<223> OTHER INFORMATION: Synthetic Construct

<400> SEQUENCE: 9

Tyr Ser Gly Ala Gln Ser Phe Phe Asn Asp Ile Ser Thr Leu Tyr Pro
1               5                   10                  15

Asn Asn Lys Asn Ile Ile Tyr Glu Leu Cys Asn Glu Pro Asn Gly
            20                  25                  30

<210> SEQ ID NO 10
<211> LENGTH: 31
<212> TYPE: PRT
<213> ORGANISM: Artificial Sequence
<220> FEATURE:
<223> OTHER INFORMATION: Synthetic Construct

<400> SEQUENCE: 10

Asn Val Arg Tyr Ala Leu Asn His Gly Ala Ala Val Phe Ala Thr Glu
1               5                   10                  15

Trp Gly Thr Ser Leu Ala Thr Gly Thr Thr Gly Pro Tyr Leu Ala
            20                  25                  30

<210> SEQ ID NO 11
<211> LENGTH: 31
<212> TYPE: PRT
<213> ORGANISM: Artificial Sequence
<220> FEATURE:
<223> OTHER INFORMATION: Synthetic Construct

<400> SEQUENCE: 11

Leu Ser Phe Asp Leu Val Asn Glu Pro Pro Asn Ile Gly Gln Tyr Gly
1               5                   10                  15

Leu Thr Arg Glu Asn His Ala Ser Leu Ile Ile Arg Thr Val Glu
            20                  25                  30

<210> SEQ ID NO 12
<211> LENGTH: 30
<212> TYPE: PRT
<213> ORGANISM: Artificial Sequence
<220> FEATURE:
<223> OTHER INFORMATION: Synthetic Construct

<400> SEQUENCE: 12

Val Asn Val His Ile Gly Glu Phe Gly Cys Phe Asn Lys Thr Ser Asn
1               5                   10                  15

Asp Val Ala Ile Arg Trp Phe Glu Asp Val Leu Ser Leu Tyr
            20                  25                  30

<210> SEQ ID NO 13
<211> LENGTH: 31
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)...(31)

<223> OTHER INFORMATION: Xaa = Any amino acid

<400> SEQUENCE: 13

Leu Ser Phe Asn Leu Ile Asn Glu Pro Pro Phe Pro Asp Pro Gln Ile
1               5                   10                  15

Xaa Ser Val Glu Asp His Asn Ser Leu Ile Lys Arg Thr Ile Thr
            20                  25                  30

<210> SEQ ID NO 14
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)...(30)
<223> OTHER INFORMATION: Xaa = Any amino acid

<400> SEQUENCE: 14

Ile Glu Val Phe Cys Gly Glu Xaa Gly Ala Tyr Asn Lys Thr Pro His
1               5                   10                  15

Asp Val Val Leu Lys Trp Leu Glu Asp Leu Leu Glu Ile Phe
            20                  25                  30

<210> SEQ ID NO 15
<211> LENGTH: 31
<212> TYPE: PRT
<213> ORGANISM: Artificial Sequence
<220> FEATURE:
<223> OTHER INFORMATION: Synthetic Construct

<400> SEQUENCE: 15

Leu Ser Phe Asn Leu Ile Asn Glu Pro Pro Phe Pro Asp Pro Gln Ile
1               5                   10                  15

Met Ser Val Glu Asp His Asn Ser Leu Ile Lys Arg Thr Ile Thr
            20                  25                  30

<210> SEQ ID NO 16
<211> LENGTH: 30
<212> TYPE: PRT
<213> ORGANISM: Artificial Sequence
<220> FEATURE:
<223> OTHER INFORMATION: Synthetic Construct

<400> SEQUENCE: 16

Ile Glu Val Phe Cys Gly Glu Met Gly Ala Tyr Asn Lys Thr Pro His
1               5                   10                  15

Asp Val Val Leu Lys Trp Leu Glu Asp Leu Leu Glu Ile Phe
            20                  25                  30

<210> SEQ ID NO 17
<211> LENGTH: 31
<212> TYPE: PRT
<213> ORGANISM: Artificial Sequence
<220> FEATURE:
<223> OTHER INFORMATION: Synthetic Construct

<400> SEQUENCE: 17

Leu Ser Phe Asn Leu Val Asn Glu Pro Leu His Pro Ser Pro Glu Val
1               5                   10                  15

Met Thr Arg Asp Asp His Asn Arg Val Ile Arg Tyr Thr Val Glu
            20                  25                  30

<210> SEQ ID NO 18

```
<211> LENGTH: 30
<212> TYPE: PRT
<213> ORGANISM: Artificial Sequence
<220> FEATURE:
<223> OTHER INFORMATION: Synthetic Construct

<400> SEQUENCE: 18

Ile Gly Val His Cys Gly Glu Ala Gly Ala Tyr Lys Phe Thr Pro His
 1               5                  10                  15

Lys Val Val Leu Ala Trp Leu Arg Asp Leu Leu Glu Ile Leu
            20                  25                  30

<210> SEQ ID NO 19
<211> LENGTH: 31
<212> TYPE: PRT
<213> ORGANISM: Artificial Sequence
<220> FEATURE:
<223> OTHER INFORMATION: Synthetic Construct

<400> SEQUENCE: 19

Leu Ser Phe Asn Leu Val Asn Glu Pro Leu His Pro Ser Pro Glu Val
 1               5                  10                  15

Met Thr Arg Glu Asp His Asn Arg Val Ile Arg Arg Thr Val Glu
            20                  25                  30

<210> SEQ ID NO 20
<211> LENGTH: 30
<212> TYPE: PRT
<213> ORGANISM: Artificial Sequence
<220> FEATURE:
<223> OTHER INFORMATION: Synthetic Construct

<400> SEQUENCE: 20

Val Gly Val His Cys Gly Glu Ala Gly Ala Tyr Lys Phe Thr Pro His
 1               5                  10                  15

Lys Val Val Ile Ala Trp Leu Arg Asp Leu Leu Glu Ile Leu
            20                  25                  30

<210> SEQ ID NO 21
<211> LENGTH: 31
<212> TYPE: PRT
<213> ORGANISM: Artificial Sequence
<220> FEATURE:
<223> OTHER INFORMATION: Synthetic Construct

<400> SEQUENCE: 21

Leu Ser Phe Asp Leu Leu Asn Glu Pro Pro Asn Val Asp Gln Tyr Gly
 1               5                  10                  15

Leu Thr Arg Leu Asn His Ala Ala Ile Met Gln Arg Thr Val Ala
            20                  25                  30

<210> SEQ ID NO 22
<211> LENGTH: 30
<212> TYPE: PRT
<213> ORGANISM: Artificial Sequence
<220> FEATURE:
<223> OTHER INFORMATION: Synthetic Construct

<400> SEQUENCE: 22

Val Ala Ile His Ile Gly Glu Phe Gly Cys Tyr Asn Arg Thr Pro Asn
 1               5                  10                  15

Asp Val Ala Leu Arg Trp Phe Arg Asp Leu Leu Ser Val Tyr
            20                  25                  30

<210> SEQ ID NO 23
```

```
<211> LENGTH: 26
<212> TYPE: PRT
<213> ORGANISM: Artificial Sequence
<220> FEATURE:
<223> OTHER INFORMATION: Synthetic Construct

<400> SEQUENCE: 23

Ile Ala Phe Glu Leu Leu Asn Glu Val Val Glu Pro Asp Ser Thr Arg
 1               5                  10                  15

Trp Asn Lys Leu Met Leu Glu Cys Ile Lys
            20                  25

<210> SEQ ID NO 24
<211> LENGTH: 30
<212> TYPE: PRT
<213> ORGANISM: Artificial Sequence
<220> FEATURE:
<223> OTHER INFORMATION: Synthetic Construct

<400> SEQUENCE: 24

Cys Lys Leu Tyr Cys Gly Glu Phe Gly Val Ile Ala Ile Ala Asp Leu
 1               5                  10                  15

Glu Ser Arg Ile Lys Trp His Glu Asp Tyr Ile Ser Leu Leu
            20                  25                  30

<210> SEQ ID NO 25
<211> LENGTH: 3294
<212> TYPE: DNA
<213> ORGANISM: Artificial Sequence
<220> FEATURE:
<223> OTHER INFORMATION: Synthetic Construct

<400> SEQUENCE: 25
atgaaaaaag ttttgtccaa gttgatggtt tttgtaatgg tattgactgt tgctttaggc      60
aacggcgtat ttgtcggcga caggcaggca aaagctgccg ggacttccgg tgatgggcgc    120
tttcacgtag tgggcaataa aatcgttgac cccgatggaa aggattttat aatcaaaggc    180
gtgaacatcc agggataccg ttcctgggag aagagaagcg tccttcagga tgttcatctg    240
atcgctgatg tatggaagtt taatacagtg aggcttaact gctttatcgg caaaacaac    300 tgggggagg ggactggcgc caataacgat attgacgcca tcattaaggc ctttacggct    360 aaaaagtgg tagtagaaat tgaccttcac gacaccacgg ggtatccgcc attgagcaat    420
cctcctccag cgccaggaca gcccagttta gatcaggcta ttgcgtggtt taaggaattg    480
gccgctaaat acaaagacaa cccttatgtc tggtttaaca ccatgaatga gcctggctcg    540
tctaccgctc cgctagaccc acagtggaaa gtggctaatg aagagatcat taaagccata    600
aggtctacag gggcagacaa tattatagtg gtggatggtt ggagctatgc caacgaaggc    660
attgagcaaa acacacctac ggtagatgaa aagagaagcg cggttttgac ctacggtcag    720
gatctgttaa acgcggacag tgctaaaaac acgattttg cctttcacaa ctataacgaa    780
ggcgatatcc agaaaaaagt tgaagattac atagacagag ctaatgcgaa gggcttgtac    840
gtgttcatgg aggaatacgg caaggattac agcgatgccg cgaaagaagg cgtaaagtct    900
ggcttacagg cagtgatgaa caaaggtgcc ggaaggatat attggaactg ggatggttac    960
gatttatacg atctgacttc aggtaccgga agggaagcg ttgggagat caataaaacc    1020 gatggatcca agcccactaa tctgagctgg gtaggggata agatatggga tgacaatcat    1080
gggattacgc cgacctttga tgatcaaaat cccaaggtgg atcttgctct ggagagattg    1140
atcgccaata caacgggttt aaagcaggc gataaagtcc agtttaccac gttttacgc    1200
```

-continued

```
aattcagggg atttgcccat tggaaaagat agcaaagtcg ttgtcaaatt ttacgtagat       1260
ggcgtgcagc tgggagatcc tgtggaaatc agcggggga  tagctgtagg ccagaggata      1320
cctgtaacgt ctcccgaact cactgtttct aagaccgatt ttacggtaaa agctgttata      1380
gatagttcaa gtacctatgc tgatggtgca gaggatgcgg ttattgaaaa caattggatt      1440
gaagccgcgt ttaatagcac tgctccttct tctggctatg aactggttgt aaccgggata      1500 aaataactc  ctgatacggt aaaggaagga gattatgtgc aggctcaggt cacggttgcc      1560
aatcagggcc ctgaggccac acctgtcaca aatataatag gatggttcta cgtcaacggc      1620
tactattata cgttagatga cgccgctaaa tcctgtgcgg aacaggacaa tgtgacctta      1680
aaaccgggtg agtcaataac tttaagcaca aaggttaaat ataggggcggc ggctcctttt    1740 aactttagtt ttgtgctgga aaatttatac gctgatgatc agaaccaatc taataactcc     1800
attacagtaa acgtgccggt taagatgggc gaaggcggcg taaacatggt gagcaacccg     1860
ggctttgaag acggtctgga cagctggcaa gactggcagc aggacatgag cgcagtgcca     1920
gaggcggctc ataatggcgc tttggggctt aaaataggtg gtggaaaggc agcaggcggt    1980
gggcaggata taccgttaaa gcccaatacc acttatatct tagggggcatg ggctaaattt    2040 gacagcaagc ctgcagggac gtttgatgtg gtggtacagt atcacttaaa ggatgcaaac    2100 aataccta tg tccagcacat tttgaatttt aacgagacgg attggacata taagcagctg     2160
ctgtttacta cacccgacgt attcggatca acgccgcagc tggcccttg  gaaaggggat      2220 acgtcaaaag ccaacctgta cgtggatgat gtatatctcg tggaagtttc caatttaata    2280
gtgaacggaa cagcagagaa cgggatggac ggatggcctg attggggtta ccggttagc      2340 gctgtacctg aggccgctta tggggcact  aaggggttta agctgtcagg cggaaaacag    2400
gcaggaatgg gccagaaagt cgctttaaag cccaatacca cttatatctt aggggcatgg    2460
ggtaaattta ccgctaaacc tggtacttac tgcgatgtca tagttcagta tcacctgaag    2520
gacgccaata ataccta tgt gcaaaacata ttgaggttta ctgaaacgga ctggacttat     2580
aagcaggtcg tatttaccac ccctgatgca tttggatcag atccagaatt tgtgctgtgg    2640
aaagatgatg cgtcaaacgc cgatttttac gccgataata tcacgctcgt tgaagtacct    2700
tcctctatgg tcaataaagg cagtatagcg ccgaaattta ctgatatatc aagcagttgg   2760
gcaaaaaacg agatacaggt tctcgcatct aaaaacataa tatcgggtta tcctgacggt    2820
acatttaagc ctgacaagag aataacgaga gctgaattcg tatccatgct tgtaaaggcc    2880
ctggggataa agcaaagcat acctgatgtc cccaccttca gcgatgtcaa caagggagat   2940
tggtattatg gtttggtgga agccgctaag agtacaggga tcgcatcagg atatggaaag   3000
cagtttaagc ctgatatgca aattacaagg caggaaatga tggtaatggt tgtaaacgcc   3060
ttgagggtta acaaagtaga aaaatttgta tccaaaggcg atgtgtcggt actgggcaaa    3120
ttcaaagatg gcggcaaggt gcaaaattgg gcaaagacg  cgatggctat aggcgtgagt   3180
aatggcttga ttaaaggcac tggcgatgag tatctgtctc ctgacgggag ggctactagg   3240
gctcaagctg ctgcagtgat atacaggatg ttgttgcagc ttggtaggat atag          3294
```

<210> SEQ ID NO 26
<211> LENGTH: 1097
<212> TYPE: PRT
<213> ORGANISM: Caldanaerobius polysaccharolyticus

<400> SEQUENCE: 26

Met Lys Lys Val Leu Ser Lys Leu Met Val Phe Val Met Val Leu Thr
1               5                   10                  15

-continued

Val Ala Leu Gly Asn Gly Val Phe Val Gly Asp Arg Gln Ala Lys Ala
        20                  25                  30

Ala Gly Thr Ser Gly Asp Gly Arg Phe His Val Val Gly Asn Lys Ile
            35                  40                  45

Val Asp Pro Asp Gly Lys Asp Phe Ile Ile Lys Gly Val Asn Ile Gln
 50                  55                  60

Gly Tyr Arg Ser Trp Glu Lys Arg Ser Val Leu Gln Asp Val His Leu
 65                  70                  75                  80

Ile Ala Asp Val Trp Lys Phe Asn Thr Val Arg Leu Asn Cys Phe Ile
                85                  90                  95

Gly Gln Asn Asn Trp Gly Glu Gly Thr Gly Ala Asn Asn Asp Ile Asp
            100                 105                 110

Ala Ile Ile Lys Ala Phe Thr Ala Lys Lys Val Val Glu Ile Asp
            115                 120                 125

Leu His Asp Thr Thr Gly Tyr Pro Pro Leu Ser Asn Pro Pro Ala
        130                 135                 140

Pro Gly Gln Pro Ser Leu Asp Gln Ala Ile Ala Trp Phe Lys Glu Leu
145                 150                 155                 160

Ala Ala Lys Tyr Lys Asp Asn Pro Tyr Val Trp Phe Asn Thr Met Asn
            165                 170                 175

Glu Pro Gly Ser Ser Thr Ala Pro Leu Asp Pro Gln Trp Lys Val Ala
            180                 185                 190

Asn Glu Glu Ile Ile Lys Ala Ile Arg Ser Thr Gly Ala Asp Asn Ile
            195                 200                 205

Ile Val Val Asp Gly Trp Ser Tyr Ala Asn Glu Gly Ile Glu Gln Asn
210                 215                 220

Thr Pro Thr Val Asp Glu Lys Arg Ser Ala Val Leu Thr Tyr Gly Gln
225                 230                 235                 240

Asp Leu Leu Asn Ala Asp Ser Ala Lys Asn Thr Ile Phe Ala Phe His
            245                 250                 255

Asn Tyr Asn Glu Gly Asp Ile Gln Lys Lys Val Glu Asp Tyr Ile Asp
            260                 265                 270

Arg Ala Asn Ala Lys Gly Leu Tyr Val Phe Met Glu Glu Tyr Gly Lys
            275                 280                 285

Asp Tyr Ser Asp Ala Ala Lys Glu Gly Val Lys Ser Gly Leu Gln Ala
            290                 295                 300

Val Met Asn Lys Gly Ala Gly Arg Ile Tyr Trp Asn Trp Asp Gly Tyr
305                 310                 315                 320

Asp Leu Tyr Asp Leu Thr Ser Gly Thr Gly Arg Gly Ser Gly Trp Glu
            325                 330                 335

Ile Asn Lys Thr Asp Gly Ser Lys Pro Thr Asn Leu Ser Trp Val Gly
            340                 345                 350

Asp Lys Ile Trp Asp Asp Asn His Gly Ile Thr Pro Thr Phe Asp Asp
            355                 360                 365

Gln Asn Pro Lys Val Asp Leu Ala Leu Glu Arg Leu Ile Ala Asn Asn
            370                 375                 380

Asn Gly Phe Lys Ala Gly Asp Lys Val Gln Phe Thr Thr Phe Leu Arg
385                 390                 395                 400

Asn Ser Gly Asp Leu Pro Ile Gly Lys Asp Ser Lys Val Val Lys
            405                 410                 415

Phe Tyr Val Asp Gly Val Gln Leu Gly Asp Pro Val Glu Ile Ser Gly
            420                 425                 430

Gly Ile Ala Val Gly Gln Arg Ile Pro Val Thr Ser Pro Glu Leu Thr

-continued

```
                435                 440                 445
Val Ser Lys Thr Asp Phe Thr Val Lys Ala Val Ile Asp Ser Ser Ser
450                 455                 460
Thr Tyr Ala Asp Gly Ala Glu Asp Ala Val Ile Glu Asn Asn Trp Ile
465                 470                 475                 480
Glu Ala Ala Phe Asn Ser Thr Ala Pro Ser Ser Gly Tyr Glu Leu Val
                485                 490                 495
Val Thr Gly Ile Lys Ile Thr Pro Asp Thr Val Lys Glu Gly Asp Tyr
                500                 505                 510
Val Gln Ala Gln Val Thr Val Ala Asn Gln Gly Pro Glu Ala Thr Pro
                515                 520                 525
Val Thr Asn Ile Ile Gly Trp Phe Tyr Val Asn Gly Tyr Tyr Tyr Thr
                530                 535                 540
Leu Asp Asp Ala Ala Lys Ser Cys Ala Glu Gln Asp Asn Val Thr Leu
545                 550                 555                 560
Lys Pro Gly Glu Ser Ile Thr Leu Ser Thr Lys Val Lys Tyr Arg Ala
                565                 570                 575
Ala Ala Pro Phe Asn Phe Ser Phe Val Leu Glu Asn Leu Tyr Ala Asp
                580                 585                 590
Asp Gln Asn Gln Ser Asn Asn Ser Ile Thr Val Asn Val Pro Val Lys
                595                 600                 605
Met Gly Glu Gly Gly Val Asn Met Val Ser Asn Pro Gly Phe Glu Asp
610                 615                 620
Gly Leu Asp Ser Trp Gln Asp Trp Gln Gln Asp Met Ser Ala Val Pro
625                 630                 635                 640
Glu Ala Ala His Asn Gly Ala Leu Gly Leu Lys Ile Gly Gly Gly Lys
                645                 650                 655
Ala Ala Gly Gly Gly Gln Asp Ile Pro Leu Lys Pro Asn Thr Thr Tyr
                660                 665                 670
Ile Leu Gly Ala Trp Ala Lys Phe Asp Ser Lys Pro Ala Gly Thr Phe
                675                 680                 685
Asp Val Val Val Gln Tyr His Leu Lys Asp Ala Asn Asn Thr Tyr Val
                690                 695                 700
Gln His Ile Leu Asn Phe Asn Glu Thr Asp Trp Thr Tyr Lys Gln Leu
705                 710                 715                 720
Leu Phe Thr Thr Pro Asp Val Phe Gly Ser Thr Pro Gln Leu Ala Leu
                725                 730                 735
Trp Lys Gly Asp Thr Ser Lys Ala Asn Leu Tyr Val Asp Val Tyr
                740                 745                 750
Leu Val Glu Val Ser Asn Leu Ile Val Asn Gly Thr Ala Glu Asn Gly
                755                 760                 765
Met Asp Gly Trp Pro Asp Trp Gly Tyr Pro Val Ser Ala Val Pro Glu
770                 775                 780
Ala Ala Tyr Gly Gly Thr Lys Gly Phe Lys Leu Ser Gly Gly Lys Gln
785                 790                 795                 800
Ala Gly Met Gly Gln Lys Val Ala Leu Lys Pro Asn Thr Thr Tyr Ile
                805                 810                 815
Leu Gly Ala Trp Gly Lys Phe Thr Ala Lys Pro Gly Thr Tyr Cys Asp
                820                 825                 830
Val Ile Val Gln Tyr His Leu Lys Asp Ala Asn Asn Thr Tyr Val Gln
                835                 840                 845
Asn Ile Leu Arg Phe Thr Glu Thr Asp Trp Thr Tyr Lys Gln Val Val
850                 855                 860
```

```
Phe Thr Thr Pro Asp Ala Phe Gly Ser Asp Pro Glu Phe Val Leu Trp
865                 870                 875                 880

Lys Asp Asp Ala Ser Asn Ala Asp Phe Tyr Ala Asp Asn Ile Thr Leu
                885                 890                 895

Val Glu Val Pro Ser Ser Met Val Asn Lys Gly Ser Ile Ala Pro Lys
            900                 905                 910

Phe Thr Asp Ile Ser Ser Ser Trp Ala Lys Asn Glu Ile Gln Val Leu
        915                 920                 925

Ala Ser Lys Asn Ile Ile Ser Gly Tyr Pro Asp Gly Thr Phe Lys Pro
    930                 935                 940

Asp Lys Arg Ile Thr Arg Ala Glu Phe Val Ser Met Leu Val Lys Ala
945                 950                 955                 960

Leu Gly Ile Lys Gln Ser Ile Pro Asp Val Pro Thr Phe Ser Asp Val
                965                 970                 975

Asn Lys Gly Asp Trp Tyr Tyr Gly Leu Val Glu Ala Ala Lys Ser Thr
            980                 985                 990

Gly Ile Ala Ser Gly Tyr Gly Lys Gln Phe Lys Pro Asp Met Gln Ile
        995                 1000                1005

Thr Arg Gln Glu Met Met Val Met Val Val Asn Ala Leu Arg Val Asn
    1010                1015                1020

Lys Val Glu Lys Phe Val Ser Lys Gly Asp Val Ser Val Leu Gly Lys
1025                1030                1035                1040

Phe Lys Asp Gly Gly Lys Val Gln Asn Trp Ala Lys Asp Ala Met Ala
                1045                1050                1055

Ile Gly Val Ser Asn Gly Leu Ile Lys Gly Thr Gly Asp Glu Tyr Leu
            1060                1065                1070

Ser Pro Asp Gly Arg Ala Thr Arg Ala Gln Ala Ala Val Ile Tyr
        1075                1080                1085

Arg Met Leu Leu Gln Leu Gly Arg Ile
    1090                1095

<210> SEQ ID NO 27
<211> LENGTH: 1065
<212> TYPE: PRT
<213> ORGANISM: Caldanaerobius polysaccharolyticus

<400> SEQUENCE: 27

Ala Gly Thr Ser Gly Asp Gly Arg Phe His Val Val Gly Asn Lys Ile
1               5                   10                  15

Val Asp Pro Asp Gly Lys Asp Phe Ile Ile Lys Gly Val Asn Ile Gln
            20                  25                  30

Gly Tyr Arg Ser Trp Glu Lys Arg Ser Val Leu Gln Asp Val His Leu
        35                  40                  45

Ile Ala Asp Val Trp Lys Phe Asn Thr Val Arg Leu Asn Cys Phe Ile
    50                  55                  60

Gly Gln Asn Asn Trp Gly Glu Gly Thr Gly Ala Asn Asn Asp Ile Asp
65                  70                  75                  80

Ala Ile Ile Lys Ala Phe Thr Ala Lys Lys Val Val Val Glu Ile Asp
                85                  90                  95

Leu His Asp Thr Thr Gly Tyr Pro Pro Leu Ser Asn Pro Pro Pro Ala
            100                 105                 110

Pro Gly Gln Pro Ser Leu Asp Gln Ala Ile Ala Trp Phe Lys Glu Leu
        115                 120                 125

Ala Ala Lys Tyr Lys Asp Asn Pro Tyr Val Trp Phe Asn Thr Met Asn
    130                 135                 140
```

```
Glu Pro Gly Ser Ser Thr Ala Pro Leu Asp Pro Gln Trp Lys Val Ala
145                 150                 155                 160

Asn Glu Glu Ile Ile Lys Ala Ile Arg Ser Thr Gly Ala Asp Asn Ile
            165                 170                 175

Ile Val Val Asp Gly Trp Ser Tyr Ala Asn Glu Gly Ile Glu Gln Asn
        180                 185                 190

Thr Pro Thr Val Asp Glu Lys Arg Ser Ala Val Leu Thr Tyr Gly Gln
    195                 200                 205

Asp Leu Leu Asn Ala Asp Ser Ala Lys Asn Thr Ile Phe Ala Phe His
210                 215                 220

Asn Tyr Asn Glu Gly Asp Ile Gln Lys Val Glu Asp Tyr Ile Asp
225                 230                 235                 240

Arg Ala Asn Ala Lys Gly Leu Tyr Val Phe Met Glu Glu Tyr Gly Lys
                245                 250                 255

Asp Tyr Ser Asp Ala Ala Lys Glu Gly Val Lys Ser Gly Leu Gln Ala
            260                 265                 270

Val Met Asn Lys Gly Ala Gly Arg Ile Tyr Trp Asn Trp Asp Gly Tyr
        275                 280                 285

Asp Leu Tyr Asp Leu Thr Ser Gly Thr Gly Arg Gly Ser Gly Trp Glu
    290                 295                 300

Ile Asn Lys Thr Asp Gly Ser Lys Pro Thr Asn Leu Ser Trp Val Gly
305                 310                 315                 320

Asp Lys Ile Trp Asp Asp Asn His Gly Ile Thr Pro Thr Phe Asp Asp
                325                 330                 335

Gln Asn Pro Lys Val Asp Leu Ala Leu Glu Arg Leu Ile Ala Asn Asn
            340                 345                 350

Asn Gly Phe Lys Ala Gly Asp Lys Val Gln Phe Thr Thr Phe Leu Arg
        355                 360                 365

Asn Ser Gly Asp Leu Pro Ile Gly Lys Asp Ser Lys Val Val Lys
    370                 375                 380

Phe Tyr Val Asp Gly Val Gln Leu Gly Asp Pro Val Glu Ile Ser Gly
385                 390                 395                 400

Gly Ile Ala Val Gly Gln Arg Ile Pro Val Thr Ser Pro Glu Leu Thr
                405                 410                 415

Val Ser Lys Thr Asp Phe Thr Val Lys Ala Val Ile Asp Ser Ser Ser
            420                 425                 430

Thr Tyr Ala Asp Gly Ala Glu Asp Ala Val Ile Glu Asn Asn Trp Ile
        435                 440                 445

Glu Ala Ala Phe Asn Ser Thr Ala Pro Ser Ser Gly Tyr Glu Leu Val
    450                 455                 460

Val Thr Gly Ile Lys Ile Thr Pro Asp Thr Val Lys Glu Gly Asp Tyr
465                 470                 475                 480

Val Gln Ala Gln Val Thr Val Ala Asn Gln Gly Pro Glu Ala Thr Pro
                485                 490                 495

Val Thr Asn Ile Ile Gly Trp Phe Tyr Val Asn Gly Tyr Tyr Tyr Thr
            500                 505                 510

Leu Asp Asp Ala Ala Lys Ser Cys Ala Glu Gln Asp Asn Val Thr Leu
        515                 520                 525

Lys Pro Gly Glu Ser Ile Thr Leu Ser Thr Lys Val Lys Tyr Arg Ala
    530                 535                 540

Ala Ala Pro Phe Asn Phe Ser Phe Val Leu Glu Asn Leu Tyr Ala Asp
545                 550                 555                 560

Asp Gln Asn Gln Ser Asn Asn Ser Ile Thr Val Asn Val Pro Val Lys
                565                 570                 575
```

```
Met Gly Glu Gly Gly Val Asn Met Val Ser Asn Pro Gly Phe Glu Asp
              580                 585                 590

Gly Leu Asp Ser Trp Gln Asp Trp Gln Gln Asp Met Ser Ala Val Pro
          595                 600                 605

Glu Ala Ala His Asn Gly Ala Leu Gly Leu Lys Ile Gly Gly Gly Lys
    610                 615                 620

Ala Ala Gly Gly Gly Gln Asp Ile Pro Leu Lys Pro Asn Thr Thr Tyr
625                 630                 635                 640

Ile Leu Gly Ala Trp Ala Lys Phe Asp Ser Lys Pro Ala Gly Thr Phe
              645                 650                 655

Asp Val Val Val Gln Tyr His Leu Lys Asp Ala Asn Thr Tyr Val
              660                 665                 670

Gln His Ile Leu Asn Phe Asn Glu Thr Asp Trp Thr Tyr Lys Gln Leu
    675                 680                 685

Leu Phe Thr Thr Pro Asp Val Phe Gly Ser Thr Pro Gln Leu Ala Leu
          690                 695                 700

Trp Lys Gly Asp Thr Ser Lys Ala Asn Leu Tyr Val Asp Asp Val Tyr
705                 710                 715                 720

Leu Val Glu Val Ser Asn Leu Ile Val Asn Gly Thr Ala Glu Asn Gly
              725                 730                 735

Met Asp Gly Trp Pro Asp Trp Gly Tyr Pro Val Ser Ala Val Pro Glu
          740                 745                 750

Ala Ala Tyr Gly Gly Thr Lys Gly Phe Lys Leu Ser Gly Gly Lys Gln
              755                 760                 765

Ala Gly Met Gly Gln Lys Val Ala Leu Lys Pro Asn Thr Thr Tyr Ile
          770                 775                 780

Leu Gly Ala Trp Gly Lys Phe Thr Ala Lys Pro Gly Thr Tyr Cys Asp
785                 790                 795                 800

Val Ile Val Gln Tyr His Leu Lys Asp Ala Asn Asn Thr Tyr Val Gln
              805                 810                 815

Asn Ile Leu Arg Phe Thr Glu Thr Asp Trp Thr Tyr Lys Gln Val Val
          820                 825                 830

Phe Thr Thr Pro Asp Ala Phe Gly Ser Asp Pro Glu Phe Val Leu Trp
          835                 840                 845

Lys Asp Asp Ala Ser Asn Ala Asp Phe Tyr Ala Asp Asn Ile Thr Leu
850                 855                 860

Val Glu Val Pro Ser Ser Met Val Asn Lys Gly Ser Ile Ala Pro Lys
865                 870                 875                 880

Phe Thr Asp Ile Ser Ser Ser Trp Ala Lys Asn Glu Ile Gln Val Leu
              885                 890                 895

Ala Ser Lys Asn Ile Ile Ser Gly Tyr Pro Asp Gly Thr Phe Lys Pro
          900                 905                 910

Asp Lys Arg Ile Thr Arg Ala Glu Phe Val Ser Met Leu Val Lys Ala
          915                 920                 925

Leu Gly Ile Lys Gln Ser Ile Pro Asp Val Pro Thr Phe Ser Asp Val
    930                 935                 940

Asn Lys Gly Asp Trp Tyr Tyr Gly Leu Val Glu Ala Ala Lys Ser Thr
945                 950                 955                 960

Gly Ile Ala Ser Gly Tyr Gly Lys Gln Phe Lys Pro Asp Met Gln Ile
              965                 970                 975

Thr Arg Gln Glu Met Met Val Met Val Val Asn Ala Leu Arg Val Asn
    980                 985                 990

Lys Val Glu Lys Phe Val Ser Lys Gly Asp Val Ser Val Leu Gly Lys
```

```
                             995                 1000                1005
Phe Lys Asp Gly Gly Lys Val Gln Asn Trp Ala Lys Asp Ala Met Ala
    1010                1015                1020

Ile Gly Val Ser Asn Gly Leu Ile Lys Gly Thr Gly Asp Glu Tyr Leu
1025                1030                1035                1040

Ser Pro Asp Gly Arg Ala Thr Arg Ala Gln Ala Ala Ala Val Ile Tyr
                1045                1050                1055

Arg Met Leu Leu Gln Leu Gly Arg Ile
            1060                1065

<210> SEQ ID NO 28
<211> LENGTH: 867
<212> TYPE: PRT
<213> ORGANISM: Caldanaerobius polysaccharolyticus

<400> SEQUENCE: 28

Ala Gly Thr Ser Gly Asp Gly Arg Phe His Val Val Gly Asn Lys Ile
  1               5                  10                  15

Val Asp Pro Asp Gly Lys Asp Phe Ile Ile Lys Gly Val Asn Ile Gln
                 20                  25                  30

Gly Tyr Arg Ser Trp Glu Lys Arg Ser Val Leu Gln Asp Val His Leu
             35                  40                  45

Ile Ala Asp Val Trp Lys Phe Asn Thr Val Arg Leu Asn Cys Phe Ile
 50                  55                  60

Gly Gln Asn Asn Trp Gly Glu Gly Thr Gly Ala Asn Asn Asp Ile Asp
 65                  70                  75                  80

Ala Ile Ile Lys Ala Phe Thr Ala Lys Lys Val Val Glu Ile Asp
                 85                  90                  95

Leu His Asp Thr Thr Gly Tyr Pro Pro Leu Ser Asn Pro Pro Ala
                100                 105                 110

Pro Gly Gln Pro Ser Leu Asp Gln Ala Ile Ala Trp Phe Lys Glu Leu
             115                 120                 125

Ala Ala Lys Tyr Lys Asp Asn Pro Tyr Val Trp Phe Asn Thr Met Asn
130                 135                 140

Glu Pro Gly Ser Ser Thr Ala Pro Leu Asp Pro Gln Trp Lys Val Ala
145                 150                 155                 160

Asn Glu Glu Ile Ile Lys Ala Ile Arg Ser Thr Gly Ala Asp Asn Ile
                165                 170                 175

Ile Val Val Asp Gly Trp Ser Tyr Ala Asn Glu Gly Ile Glu Gln Asn
            180                 185                 190

Thr Pro Thr Val Asp Glu Lys Arg Ser Ala Val Leu Thr Tyr Gly Gln
        195                 200                 205

Asp Leu Leu Asn Ala Asp Ser Ala Lys Asn Thr Ile Phe Ala Phe His
    210                 215                 220

Asn Tyr Asn Glu Gly Asp Ile Gln Lys Val Glu Asp Tyr Ile Asp
225                 230                 235                 240

Arg Ala Asn Ala Lys Gly Leu Tyr Val Phe Met Glu Glu Tyr Gly Lys
                245                 250                 255

Asp Tyr Ser Asp Ala Ala Lys Glu Gly Val Lys Ser Gly Leu Gln Ala
            260                 265                 270

Val Met Asn Lys Gly Ala Gly Arg Ile Tyr Trp Asn Trp Asp Gly Tyr
        275                 280                 285

Asp Leu Tyr Asp Leu Thr Ser Gly Thr Gly Arg Gly Ser Gly Trp Glu
    290                 295                 300

Ile Asn Lys Thr Asp Gly Ser Lys Pro Thr Asn Leu Ser Trp Val Gly
```

-continued

```
             305                 310                 315                 320
Asp Lys Ile Trp Asp Asp Asn His Gly Ile Thr Pro Thr Phe Asp Asp
                 325                 330                 335

Gln Asn Pro Lys Val Asp Leu Ala Leu Glu Arg Leu Ile Ala Asn Asn
             340                 345                 350

Asn Gly Phe Lys Ala Gly Asp Lys Val Gln Phe Thr Thr Phe Leu Arg
         355                 360                 365

Asn Ser Gly Asp Leu Pro Ile Gly Lys Asp Ser Lys Val Val Lys
     370                 375                 380

Phe Tyr Val Asp Gly Val Gln Leu Gly Asp Pro Val Glu Ile Ser Gly
385                 390                 395                 400

Gly Ile Ala Val Gly Gln Arg Ile Pro Val Thr Ser Pro Glu Leu Thr
                 405                 410                 415

Val Ser Lys Thr Asp Phe Thr Val Lys Ala Val Ile Asp Ser Ser Ser
             420                 425                 430

Thr Tyr Ala Asp Gly Ala Glu Asp Ala Val Ile Glu Asn Asn Trp Ile
         435                 440                 445

Glu Ala Ala Phe Asn Ser Thr Ala Pro Ser Ser Gly Tyr Glu Leu Val
     450                 455                 460

Val Thr Gly Ile Lys Ile Thr Pro Asp Thr Val Lys Glu Gly Asp Tyr
465                 470                 475                 480

Val Gln Ala Gln Val Thr Val Ala Asn Gln Gly Pro Glu Ala Thr Pro
                 485                 490                 495

Val Thr Asn Ile Ile Gly Trp Phe Tyr Val Asn Gly Tyr Tyr Tyr Thr
             500                 505                 510

Leu Asp Asp Ala Ala Lys Ser Cys Ala Glu Gln Asp Asn Val Thr Leu
         515                 520                 525

Lys Pro Gly Glu Ser Ile Thr Leu Ser Thr Lys Val Lys Tyr Arg Ala
     530                 535                 540

Ala Ala Pro Phe Asn Phe Ser Phe Val Leu Glu Asn Leu Tyr Ala Asp
545                 550                 555                 560

Asp Gln Asn Gln Ser Asn Asn Ser Ile Thr Val Asn Val Pro Val Lys
                 565                 570                 575

Met Gly Glu Gly Gly Val Asn Met Val Ser Asn Pro Gly Phe Glu Asp
             580                 585                 590

Gly Leu Asp Ser Trp Gln Asp Trp Gln Gln Asp Met Ser Ala Val Pro
         595                 600                 605

Glu Ala Ala His Asn Gly Ala Leu Gly Leu Lys Ile Gly Gly Gly Lys
     610                 615                 620

Ala Ala Gly Gly Gly Gln Asp Ile Pro Leu Lys Pro Asn Thr Thr Tyr
625                 630                 635                 640

Ile Leu Gly Ala Trp Ala Lys Phe Asp Ser Lys Pro Ala Gly Thr Phe
                 645                 650                 655

Asp Val Val Val Gln Tyr His Leu Lys Asp Ala Asn Asn Thr Tyr Val
             660                 665                 670

Gln His Ile Leu Asn Phe Asn Glu Thr Asp Trp Thr Tyr Lys Gln Leu
         675                 680                 685

Leu Phe Thr Thr Pro Asp Val Phe Gly Ser Thr Pro Gln Leu Ala Leu
     690                 695                 700

Trp Lys Gly Asp Thr Ser Lys Ala Asn Leu Tyr Val Asp Asp Val Tyr
705                 710                 715                 720

Leu Val Glu Val Ser Asn Leu Ile Val Asn Gly Thr Ala Glu Asn Gly
                 725                 730                 735
```

```
Met Asp Gly Trp Pro Asp Trp Gly Tyr Pro Val Ser Ala Val Pro Glu
                740                 745                 750

Ala Ala Tyr Gly Gly Thr Lys Gly Phe Lys Leu Ser Gly Gly Lys Gln
            755                 760                 765

Ala Gly Met Gly Gln Lys Val Ala Leu Lys Pro Asn Thr Thr Tyr Ile
        770                 775                 780

Leu Gly Ala Trp Gly Lys Phe Thr Ala Lys Pro Gly Thr Tyr Cys Asp
785                 790                 795                 800

Val Ile Val Gln Tyr His Leu Lys Asp Ala Asn Asn Thr Tyr Val Gln
                805                 810                 815

Asn Ile Leu Arg Phe Thr Glu Thr Asp Trp Thr Tyr Lys Gln Val Val
            820                 825                 830

Phe Thr Thr Pro Asp Ala Phe Gly Ser Asp Pro Glu Phe Val Leu Trp
        835                 840                 845

Lys Asp Asp Ala Ser Asn Ala Asp Phe Tyr Ala Asp Asn Ile Thr Leu
850                 855                 860

Val Glu Val
865

<210> SEQ ID NO 29
<211> LENGTH: 576
<212> TYPE: PRT
<213> ORGANISM: Caldanaerobius polysaccharolyticus

<400> SEQUENCE: 29

Ala Gly Thr Ser Gly Asp Gly Arg Phe His Val Val Gly Asn Lys Ile
 1               5                  10                  15

Val Asp Pro Asp Gly Lys Asp Phe Ile Ile Lys Gly Val Asn Ile Gln
            20                  25                  30

Gly Tyr Arg Ser Trp Glu Lys Arg Ser Val Leu Gln Asp Val His Leu
        35                  40                  45

Ile Ala Asp Val Trp Lys Phe Asn Thr Val Arg Leu Asn Cys Phe Ile
    50                  55                  60

Gly Gln Asn Asn Trp Gly Glu Gly Thr Gly Ala Asn Asn Asp Ile Asp
65                  70                  75                  80

Ala Ile Ile Lys Ala Phe Thr Ala Lys Lys Val Val Val Glu Ile Asp
                85                  90                  95

Leu His Asp Thr Thr Gly Tyr Pro Pro Leu Ser Asn Pro Pro Pro Ala
            100                 105                 110

Pro Gly Gln Pro Ser Leu Asp Gln Ala Ile Ala Trp Phe Lys Glu Leu
        115                 120                 125

Ala Ala Lys Tyr Lys Asp Asn Pro Tyr Val Trp Phe Asn Thr Met Asn
    130                 135                 140

Glu Pro Gly Ser Ser Thr Ala Pro Leu Asp Pro Gln Trp Lys Val Ala
145                 150                 155                 160

Asn Glu Glu Ile Ile Lys Ala Ile Arg Ser Thr Gly Ala Asp Asn Ile
                165                 170                 175

Ile Val Val Asp Gly Trp Ser Tyr Ala Asn Glu Gly Ile Glu Gln Asn
            180                 185                 190

Thr Pro Thr Val Asp Glu Lys Arg Ser Ala Val Leu Thr Tyr Gly Gln
        195                 200                 205

Asp Leu Leu Asn Ala Asp Ser Ala Lys Asn Thr Ile Phe Ala Phe His
    210                 215                 220

Asn Tyr Asn Glu Gly Asp Ile Gln Lys Lys Val Glu Asp Tyr Ile Asp
225                 230                 235                 240
```

```
Arg Ala Asn Ala Lys Gly Leu Tyr Val Phe Met Glu Glu Tyr Gly Lys
                245                 250                 255

Asp Tyr Ser Asp Ala Ala Lys Glu Gly Val Lys Ser Gly Leu Gln Ala
        260                 265                 270

Val Met Asn Lys Gly Ala Gly Arg Ile Tyr Trp Asn Trp Asp Gly Tyr
            275                 280                 285

Asp Leu Tyr Asp Leu Thr Ser Gly Thr Gly Arg Gly Ser Gly Trp Glu
    290                 295                 300

Ile Asn Lys Thr Asp Gly Ser Lys Pro Thr Asn Leu Ser Trp Val Gly
305                 310                 315                 320

Asp Lys Ile Trp Asp Asn His Gly Ile Thr Pro Thr Phe Asp Asp
                325                 330                 335

Gln Asn Pro Lys Val Asp Leu Ala Leu Glu Arg Leu Ile Ala Asn Asn
                340                 345                 350

Asn Gly Phe Lys Ala Gly Asp Lys Val Gln Phe Thr Thr Phe Leu Arg
            355                 360                 365

Asn Ser Gly Asp Leu Pro Ile Gly Lys Asp Ser Lys Val Val Val Lys
    370                 375                 380

Phe Tyr Val Asp Gly Val Gln Leu Gly Asp Pro Val Glu Ile Ser Gly
385                 390                 395                 400

Gly Ile Ala Val Gly Gln Arg Ile Pro Val Thr Ser Pro Glu Leu Thr
                405                 410                 415

Val Ser Lys Thr Asp Phe Thr Val Lys Ala Val Ile Asp Ser Ser Ser
            420                 425                 430

Thr Tyr Ala Asp Gly Ala Glu Asp Ala Val Ile Glu Asn Asn Trp Ile
    435                 440                 445

Glu Ala Ala Phe Asn Ser Thr Ala Pro Ser Ser Gly Tyr Glu Leu Val
450                 455                 460

Val Thr Gly Ile Lys Ile Thr Pro Asp Thr Val Lys Glu Gly Asp Tyr
465                 470                 475                 480

Val Gln Ala Gln Val Thr Val Ala Asn Gln Gly Pro Glu Ala Thr Pro
                485                 490                 495

Val Thr Asn Ile Ile Gly Trp Phe Tyr Val Asn Gly Tyr Tyr Tyr Thr
            500                 505                 510

Leu Asp Asp Ala Ala Lys Ser Cys Ala Glu Gln Asp Asn Val Thr Leu
    515                 520                 525

Lys Pro Gly Glu Ser Ile Thr Leu Ser Thr Lys Val Lys Tyr Arg Ala
530                 535                 540

Ala Ala Pro Phe Asn Phe Ser Phe Val Leu Glu Asn Leu Tyr Ala Asp
545                 550                 555                 560

Asp Gln Asn Gln Ser Asn Asn Ser Ile Thr Val Asn Val Pro Val Lys
                565                 570                 575

<210> SEQ ID NO 30
<211> LENGTH: 993
<212> TYPE: DNA
<213> ORGANISM: Artificial Sequence
<220> FEATURE:
<223> OTHER INFORMATION: Synthetic Construct

<400> SEQUENCE: 30
atgaaaaaat atggctttaa cttccaatgg atgtacgtat gggaggaagg aagagaaccc    60
gagcctccag ataaaaaagc gttggatttt ttagcagaga caggatttaa ctttgtcagg   120 ataccgttg attatagatt ttggacgaga aattttgatt actttaaccc tgataaaaaa    180
gtttttgagt atatcgattt ataccttagg gaatgcagcg ctaggaacat tcacatgtgt   240
```

-continued

```
ttgaatttgc acagggctcc tggttattgc ataaaccgca acgatataga gcgcgacaac    300
ttgtggctgg ataaaagagc gcaagacggc tttgtatacc agtgggagct ttttgcaaag    360
cggtataaag gagtttctag caagttttta agctttgatc tcgtaaatga acctcctaat    420
atcggccaat acggcttgac aagagaaaac catgcttctc ttataattcg tacggtagaa    480
gccatacgca aaatagatcc tgaccgcgaa atagtgatag acggtttggg aggtggaaat    540
atcgccatgc cagagctggc ccatttaggt gttgtgcaca gcggcagagg ttatcaaccc    600
atggctttga ctcattatca ggctagctgg tgggatggcc acaaaggctt gcctgaaccc    660
tattatcctg atttgttgtg gcaaggtaaa gtatggaaca aggatacgtt acgagaatac    720
tataaaccat ggcgtgattt gcagcaaaaa ggagttaatg tgcacatagg ggaatttgga    780
tgctttaata agacctctaa cgatgtggct attaggtggt ttgaagatgt gttgagcctg    840
tataaggaat ttgaatgggg atattccctg tggaatttta aagggccttt tgggattgta    900
gagcatggcc gtccaggtgc caaatatgaa tattatcgcg gtttcaaagt agatagagaa    960
ttgctggatt tgcttgtgga aatagagta taa                                  993
```

```
<210> SEQ ID NO 31
<211> LENGTH: 330
<212> TYPE: PRT
<213> ORGANISM: Caldanaerobius polysaccharolyticus

<400> SEQUENCE: 31

Met Lys Lys Tyr Gly Phe Asn Phe Gln Trp Met Tyr Val Trp Glu Glu
  1               5                  10                  15

Gly Arg Glu Pro Glu Pro Pro Asp Lys Lys Ala Leu Asp Phe Leu Ala
             20                  25                  30

Glu Thr Gly Phe Asn Phe Val Arg Ile Pro Val Asp Tyr Arg Phe Trp
         35                  40                  45

Thr Arg Asn Phe Asp Tyr Phe Asn Pro Asp Lys Lys Val Phe Glu Tyr
     50                  55                  60

Ile Asp Leu Tyr Leu Arg Glu Cys Ser Ala Arg Asn Ile His Met Cys
 65                  70                  75                  80

Leu Asn Leu His Arg Ala Pro Gly Tyr Cys Ile Asn Arg Asn Asp Ile
                 85                  90                  95

Glu Arg Asp Asn Leu Trp Leu Asp Lys Arg Ala Gln Asp Gly Phe Val
            100                 105                 110

Tyr Gln Trp Glu Leu Phe Ala Lys Arg Tyr Lys Gly Val Ser Ser Lys
        115                 120                 125

Phe Leu Ser Phe Asp Leu Val Asn Glu Pro Pro Asn Ile Gly Gln Tyr
    130                 135                 140

Gly Leu Thr Arg Glu Asn His Ala Ser Leu Ile Ile Arg Thr Val Glu
145                 150                 155                 160

Ala Ile Arg Lys Ile Asp Pro Asp Arg Glu Ile Val Ile Asp Gly Leu
                165                 170                 175

Gly Gly Gly Asn Ile Ala Met Pro Glu Leu Ala His Leu Gly Val Val
            180                 185                 190

His Ser Gly Arg Gly Tyr Gln Pro Met Ala Leu Thr His Tyr Gln Ala
        195                 200                 205

Ser Trp Trp Asp Gly His Lys Gly Leu Pro Glu Pro Tyr Tyr Pro Asp
    210                 215                 220

Leu Leu Trp Gln Gly Lys Val Trp Asn Lys Asp Thr Leu Arg Glu Tyr
225                 230                 235                 240
```

-continued

Tyr Lys Pro Trp Arg Asp Leu Gln Gln Lys Gly Val Asn Val His Ile
                245                 250                 255

Gly Glu Phe Gly Cys Phe Asn Lys Thr Ser Asn Asp Val Ala Ile Arg
            260                 265                 270

Trp Phe Glu Asp Val Leu Ser Leu Tyr Lys Glu Phe Gly Trp Gly Tyr
        275                 280                 285

Ser Leu Trp Asn Phe Lys Gly Pro Phe Gly Ile Val Glu His Gly Arg
    290                 295                 300

Pro Gly Ala Lys Tyr Glu Tyr Tyr Arg Gly Phe Lys Val Asp Arg Glu
305                 310                 315                 320

Leu Leu Asp Leu Leu Val Glu Asn Arg Val
                325                 330

<210> SEQ ID NO 32
<211> LENGTH: 30
<212> TYPE: DNA
<213> ORGANISM: Artificial Sequence
<220> FEATURE:
<223> OTHER INFORMATION: Synthetic Construct

<400> SEQUENCE: 32
catatggccg ggacttccgg tgatgggcgc                                    30

<210> SEQ ID NO 33
<211> LENGTH: 34
<212> TYPE: DNA
<213> ORGANISM: Artificial Sequence
<220> FEATURE:
<223> OTHER INFORMATION: Synthetic Construct

<400> SEQUENCE: 33
ctcgagctat acttcaacga gcgtgatatt atcg                               34

<210> SEQ ID NO 34
<211> LENGTH: 30
<212> TYPE: DNA
<213> ORGANISM: Artificial Sequence
<220> FEATURE:
<223> OTHER INFORMATION: Synthetic Construct

<400> SEQUENCE: 34
catatggccg ggacttccgg tgatgggcgc                                    30

<210> SEQ ID NO 35
<211> LENGTH: 35
<212> TYPE: DNA
<213> ORGANISM: Artificial Sequence
<220> FEATURE:
<223> OTHER INFORMATION: Synthetic Construct

<400> SEQUENCE: 35
ctcgagctac ttaaccggca cgtttactgt aatgg                              35

<210> SEQ ID NO 36
<211> LENGTH: 42
<212> TYPE: DNA
<213> ORGANISM: Artificial Sequence
<220> FEATURE:
<223> OTHER INFORMATION: Synthetic Construct

<400> SEQUENCE: 36
gacgacgaca agatgaaaaa atatggcttt aacttccaat gg                      42

<210> SEQ ID NO 37

```
<211> LENGTH: 41
<212> TYPE: DNA
<213> ORGANISM: Artificial Sequence
<220> FEATURE:
<223> OTHER INFORMATION: Synthetic Construct

<400> SEQUENCE: 37
gaggagaagc ccggttatac tctattctcc acaagcaaat c                    41

<210> SEQ ID NO 38
<211> LENGTH: 36
<212> TYPE: DNA
<213> ORGANISM: Artificial Sequence
<220> FEATURE:
<223> OTHER INFORMATION: Synthetic Construct

<400> SEQUENCE: 38
tctggtttaa caccatgaat gcgcctggct cgtcta                          36

<210> SEQ ID NO 39
<211> LENGTH: 36
<212> TYPE: DNA
<213> ORGANISM: Artificial Sequence
<220> FEATURE:
<223> OTHER INFORMATION: Synthetic Construct

<400> SEQUENCE: 39
tagacgagcc aggcgcattc atggtgttaa accaga                          36

<210> SEQ ID NO 40
<211> LENGTH: 33
<212> TYPE: DNA
<213> ORGANISM: Artificial Sequence
<220> FEATURE:
<223> OTHER INFORMATION: Synthetic Construct

<400> SEQUENCE: 40
gtctggttta acaccatgaa tcagcctggc tcg                             33

<210> SEQ ID NO 41
<211> LENGTH: 32
<212> TYPE: DNA
<213> ORGANISM: Artificial Sequence
<220> FEATURE:
<223> OTHER INFORMATION: Synthetic Construct

<400> SEQUENCE: 41
gagccaggct gattcatggt gttaaaccag ac                              32

<210> SEQ ID NO 42
<211> LENGTH: 35
<212> TYPE: DNA
<213> ORGANISM: Artificial Sequence
<220> FEATURE:
<223> OTHER INFORMATION: Synthetic Construct

<400> SEQUENCE: 42
gtacgtgttc atggaggcat acggcaagga ttaca                           35

<210> SEQ ID NO 43
<211> LENGTH: 35
<212> TYPE: DNA
<213> ORGANISM: Artificial Sequence
<220> FEATURE:
<223> OTHER INFORMATION: Synthetic Construct

<400> SEQUENCE: 43
```

```
tgtaatcctt gccgtatgcc tccatgaaca cgtac                                      35
```

<210> SEQ ID NO 44
<211> LENGTH: 41
<212> TYPE: DNA
<213> ORGANISM: Artificial Sequence
<220> FEATURE:
<223> OTHER INFORMATION: Synthetic Construct

<400> SEQUENCE: 44

```
cttgtacgtg ttcatggagc agtacggcaa ggattacagc g                               41
```

<210> SEQ ID NO 45
<211> LENGTH: 41
<212> TYPE: DNA
<213> ORGANISM: Artificial Sequence
<220> FEATURE:
<223> OTHER INFORMATION: Synthetic Construct

<400> SEQUENCE: 45

```
cgctgtaatc cttgccgtac tgctccatga acacgtacaa g                               41
```

<210> SEQ ID NO 46
<211> LENGTH: 41
<212> TYPE: DNA
<213> ORGANISM: Artificial Sequence
<220> FEATURE:
<223> OTHER INFORMATION: Synthetic Construct

<400> SEQUENCE: 46

```
tttaagcttt gatctcgtaa atgcacctcc taatatcggc c                               41
```

<210> SEQ ID NO 47
<211> LENGTH: 41
<212> TYPE: DNA
<213> ORGANISM: Artificial Sequence
<220> FEATURE:
<223> OTHER INFORMATION: Synthetic Construct

<400> SEQUENCE: 47

```
ggccgatatt aggaggtgca tttacgagat caaagcttaa a                               41
```

<210> SEQ ID NO 48
<211> LENGTH: 45
<212> TYPE: DNA
<213> ORGANISM: Artificial Sequence
<220> FEATURE:
<223> OTHER INFORMATION: Synthetic Construct

<400> SEQUENCE: 48

```
caagttttta gctttgatc tcgtaaatca gcctcctaat atcgg                            45
```

<210> SEQ ID NO 49
<211> LENGTH: 46
<212> TYPE: DNA
<213> ORGANISM: Artificial Sequence
<220> FEATURE:
<223> OTHER INFORMATION: Synthetic Construct

<400> SEQUENCE: 49

```
gccgatatta ggaggctgat ttacgagatc aaagcttaaa aacttg                          46
```

<210> SEQ ID NO 50
<211> LENGTH: 43
<212> TYPE: DNA
<213> ORGANISM: Artificial Sequence
<220> FEATURE:

<223> OTHER INFORMATION: Synthetic Construct

<400> SEQUENCE: 50
gagttaatgt gcacataggg gcatttggat gctttaataa gac         43

<210> SEQ ID NO 51
<211> LENGTH: 43
<212> TYPE: DNA
<213> ORGANISM: Artificial Sequence
<220> FEATURE:
<223> OTHER INFORMATION: Synthetic Construct

<400> SEQUENCE: 51
gtcttattaa agcatccaaa tgccctatg tgcacattaa ctc           43

<210> SEQ ID NO 52
<211> LENGTH: 45
<212> TYPE: DNA
<213> ORGANISM: Artificial Sequence
<220> FEATURE:
<223> OTHER INFORMATION: Synthetic Construct

<400> SEQUENCE: 52
ggagttaatg tgcacatagg gcagtttgga tgctttaata agacc        45

<210> SEQ ID NO 53
<211> LENGTH: 45
<212> TYPE: DNA
<213> ORGANISM: Artificial Sequence
<220> FEATURE:
<223> OTHER INFORMATION: Synthetic Construct

<400> SEQUENCE: 53
ggtcttatta aagcatccaa actgccctat gtgcacatta actcc        45

<210> SEQ ID NO 54
<211> LENGTH: 13
<212> TYPE: DNA
<213> ORGANISM: Artificial Sequence
<220> FEATURE:
<223> OTHER INFORMATION: Synthetic Construct

<400> SEQUENCE: 54
gacgacgaca aga                                            13

<210> SEQ ID NO 55
<211> LENGTH: 15
<212> TYPE: DNA
<213> ORGANISM: Artificial Sequence
<220> FEATURE:
<223> OTHER INFORMATION: Synthetic Construct

<400> SEQUENCE: 55
gaggagaagc ccggt                                          15

THERMOSTABLE ENZYMES FOR THE HYDROLYSIS OF MANNAN-CONTAINING POLYSACCHARIDES

This application claims the benefit under 35 USC 119(e) of U.S. Provisional Patent Application No. 61/349,789, filed May 28, 2010, the disclosure of which is hereby incorporated by reference in its entirety.

SUBMISSION OF SEQUENCE LISTING AS ASCII TEXT FILE

The content of the following submission on ASCII text file is incorporated herein by reference in its entirety: a computer readable form (CRF) of the Sequence Listing (file name: 658012000600SeqList.txt, date recorded: May 10, 2011, size: 51 kB).

FIELD

The present disclosure relates to hydrolysis of mannan-containing poly- or oligo-saccharides by use of a polypeptide having endo-β-mannanase activity. In particular the present disclosure relates to compositions comprising a bacterial endo-β-mannanase, polynucleotides encoding the endo-β-mannanase, and methods of use thereof.

BACKGROUND

Bioenergy feedstocks consist primarily of the plant cell wall components cellulose and hemicellulose, and hydrolysis of these polysaccharides to their monomeric sugars involves a set of enzymes acting synergistically to cleave the different chemical linkages (Dodd and Cann, GCB Bioenergy, 1:2, 2009). Although cellulose consists of glucose units linked together in β-1,4-glycosidic linkages, the hemicellulosic component of feedstock may vary in chemical composition. Some feedstock hemicellulose are mainly composed of β-1, 4-linked xylose backbones with arabinose side chains, while others are comprised of a larger variety of sugars including galactose and mannose existing as various forms of mannan. Mannans constitute a less significant portion of hemicellulose in bioenergy feedstocks such as switchgrass. However, the presence of mannan may result in linkages that restrict release of fermentable sugars.

A variety of mannans are found in nature. These include linear mannan, glucomannan, galactomannan, and glucogalactomannan. In each case, the polysaccharide contains a β-1,4-linked backbone of mannose residues that may be substituted up to 33% (or up to 50% in hardwoods) with glucose residues (Yeoman et al., Adv Appl Microbiol, Elsivier). In galactomannans or glucogalactomannnans, galactose residues are linked in β-1,6-linkages to the mannan backbone (Moreira and Filho, Appl Microbiol Biotechnol, 79:165, 2008). Therefore, hydrolysis of mannan to its component sugars requires endo-1,4-β-mannanases that hydrolyze the backbone linkages to generate short chain manno-oligosaccharides that are further degraded to monosaccharides by 1,4-β-mannosidases.

Reactions at high temperatures are critical for the enzymatic conversion of plant cell wall polysaccharides to fermentable sugars in the emerging biofuel industry. Thus what is needed in the art are thermostable enzymes for the hydrolysis of mannans contained in biofuel feedstocks. Compositions and methods comprising thermostable endo-β-mannanases will find utility in the enzymatic depolymerization of lignocellulose.

BRIEF SUMMARY

The present disclosure relates to isolated bacterial endo-β-mannanase polypeptides such as *Caldanaerobius polysaccharolyticus* endo-β-mannanase 5B (Man5B), *Caldanaerobius polysaccharolyticus* endo-β-mannanase 5A (Man5A), and fragments thereof. The present disclosure also relates to isolated polynucleotides encoding the endo-β-mannanase polypeptides, as well as vectors and genetically modified host cells containing such isolated polynucleotides. The present disclosure further relates to compositions comprising an isolated endo-β-mannanase or enriched in such endo-β-mannanase. Moreover the present disclosure relates to methods for the production of a endo-β-mannanase, and methods for hydrolysis of a mannan-containing poly- or oligo-saccharides with such compositions.

In particular, the present disclosure provides isolated proteins comprising the amino acid sequence that is at least 85% identical (85%, 86%, 87%, 88%, 89%, 90%, 91%, 92%, 93%, 94%, 95%, 96%, 97%, 98%, 99%, or 100%) to *Caldanaerobius polysaccharolyticus* endo-β-mannanase 5B (Man5B) of SEQ ID NO: 31. In some embodiments, the amino acid sequence is at least 95% (95%, 96%, 97%, 98%, 99% or 100%) identical to the Man5B of SEQ ID NO: 31. Also provided are compositions comprising the isolated proteins. In some embodiments, the compositions further comprise a second isolated protein comprising the second amino acid sequence that is at least 95% identical (95%, 96%, 97%, 98%, 99%, or 100%) to one of the group consisting of *Caldanaerobius polysaccharolyticus* endo-β-mannanase 5A (Man5A) of SEQ ID NO: 27, a long Man5 fragment (Man5ATM1) of SEQ ID NO: 28, and a short Man5 fragment (Man5ATM2) of SEQ ID NO: 29. In some embodiments, the second amino acid sequence is at least 95% identical (95%, 96%, 97%, 98%, 99%, or 100%) to the Man5A of SEQ ID NO: 27. In other embodiments, the second amino acid sequence is at least 95% identical (95%, 96%, 97%, 98%, 99%, or 100%) to the Man5ATM1 of SEQ ID NO: 28. Alternatively, the second amino acid sequence is at least 95% identical (95%, 96%, 97%, 98%, 99%, or 100%) to the Man5ATM2 of SEQ ID NO: 29. In still further embodiments, the second isolated protein comprises two or more of Man5A, Man5ATM1, and Man5ATM2.

In addition the present disclosure provides isolated nucleic acids encoding an endo-β-mannanase comprising the amino acid sequence that is at least 85% identical (85%, 86%, 87%, 88%, 89%, 90%, 91%, 92%, 93%, 94%, 95%, 96%, 97%, 98%, 99%, or 100%) to *C. polysaccharolyticus* endo-β-mannanase 5B (Man5B) of SEQ ID NO: 31. In some embodiments, expression vectors are provided comprising the isolated nucleic acid in operably linked to a regulatory sequence. In other embodiments, host cells are provided comprising the expression vector. In still further embodiments, methods are provided for producing the endo-β-mannanase, comprising: culturing the host cell in a culture medium, under suitable conditions to produce the endo-β-mannanase. The present disclosure also provides compositions comprising the host cell and culture medium, and compositions comprising the endo-β-mannanase in supernatant of the culture medium.

Moreover the present disclosure provides methods of employing a composition of any of the preceding paragraphs (e.g., composition comprising a protein comprising the amino acid sequence that is at least 85% identical (85%, 86%, 87%, 88%, 89%, 90%, 91%, 92%, 93%, 94%, 95%, 96%, 97%, 98%, 99%, or 100%) to *C. polysaccharolyticus* Man5B of SEQ ID NO: 31. In some embodiments, methods are provided for converting biomass to sugars comprising contacting the biomass with the composition. In some embodiments, methods are provided for producing a fuel comprising: contacting a biomass with the composition to yield a sugar solution; and culturing the sugar solution with a fermentative microorganism under conditions sufficient to produce a fuel. In some preferred embodiments, the biomass comprises a plant material. In exemplary embodiments, the plant material is selected from the group consisting of Miscanthus, switchgrass, cord grass, rye grass, reed canary grass, common reed, wheat straw, barley straw, canola straw, oat straw, corn stover, soybean stover, oat hulls, sorghum, rice hulls, sugarcane bagasse, corn fiber, Distillers Dried Grains with Solubles (DDGS), Blue Stem, corncobs, pine, willow, aspen, poplar wood, and energy cane. In some embodiments, the biomass comprises a softwood, while in others the biomass comprises a hardwood. In some preferred embodiments, the biomass comprises a woody feedstock with a mannan content of at least 2% by weight (from 2% to 90% w/w, preferably at least 5% w/w, preferably at least 10% w/w). In further embodiments, methods are provided for food processing, comprising: contacting a plant material with the composition to yield a treated plant material. In certain embodiments, the treated plant material is fed to animals. In other embodiments, the plant material is selected from palm kernel, coconut, konjac, locust bean gum, gum guar, soy beans, barley, oats, flax, wheat, corn, linseed, citrus pulp, cottonseed, groundnut, rapeseed, sunflower, peas, and lupines. In still further embodiments, there is provided food additives comprising the composition. Also provided are methods for textile cleaning, comprising: contacting a soiled textile with the composition of to yield a clean textile. In addition, methods are provided for paper pulp bleaching, comprising: contacting paper pulp with the composition to yield bleached paper pulp. In some embodiments, the contacting is conducted at a pH between 4.5 and 7, preferably at a pH between 5.5 and 6. In further embodiments, the contacting is conducted at a temperature between 45 and 80° C., preferably between 60 to 70° C.

BRIEF DESCRIPTION OF THE DRAWINGS

In FIG. 4A, the proteins (50 nM, final concentration) were incubated with each substrate (0.5% w/v) in citrate reaction buffer (50 mM, pH 5.5) for 5 min at 65° C., and the amounts of reducing ends released were determined. For each experiment, the reactions were performed three independent times and the data were reported as means±standard deviations from the mean. In FIG. 4B, either buffer or protein (40 µmol each) was spotted on an agar plate infused with the appropriate polysaccharide (0.2% w/v) and the plate was incubated at 65° C. for 3 h followed by staining with Congo red. The proteins spotted on the agar plates are as follows: 1, Man5A-TM1; 2, Man5A-TM2; and 3, Man5B.

FIG. 6A provides amino acid sequences of two conserved regions adjacent to the predicted active sites of: Man5ATM1 (SEQ ID NO: 1 and 2); Tfu 1BGC_A (SEQ ID NO: 3 and 4); Gro AAC63988 (SEQ ID NO: 5 and 6); Asp AAC)6196 (SEQ ID NO: 7 and 8); and Cce ZP_04805792 (SEQ ID NO: 9 and 10). FIG. 6B provides a three-dimensional homology model of Man5A-TM1 including putative active site residues (Glu 177 and Glu 285, indicated by arrows). The model was created by using the *Thermobifida fusca* β-mannanase (Tfu-1BQC_A, Protein Data Bank Accession No. 1BQC_A) as the template. FIGS. 6C and 6D provide CD-spectra analysis and SDS-PAGE respectively, of wild type and/or mutants of Man5A-TM1.

FIG. 7A provides amino acid sequences of two conserved regions adjacent to the predicted active sites: Man5B (SEQ ID NO: 11 and 12); Tma 1VJZ_A (SEQ ID NO: 13 and 14); Tma NP_229550 (SEQ ID NO: 15 and 16); Dth YP_002250389 (SEQ ID NO: 17 and 18); Dth YP_0023570 (SEQ ID NO: 19 and 20); Hau YP_0015443664 (SEQ ID NO: 21 and 22); and Cth 1CEC_A (SEQ ID NO: 23 and 24). FIG. 7B provides a three-dimensional homology model of Man5B, including putative active site residues catalytic residues (Glu 137 and Glu 258, indicated by arrows). The model was created by using the structure of a *Thermotoga maritima* endoglucanase (Tma-1VJZ_A, Protein Data Bank Accession No.) as the template. FIGS. 7C and 7D provide CD-spectra SDS-PAGE analyses, respectively wild type and mutants of Man5B.

FIG. 10A shows the results of the Control. FIG. 10B shows the results of Man5ATM1. FIG. 10C shows the results of Man5ATM2. FIG. 10D shows the results of Man5B. FIG. 10E shows the results of the combination of Man5ATM1 and Man5ATM2. FIG. 10F shows results of the combination of Man5ATM1 and Man5B. FIG. 10G shows the results of the combination of Man5ATM2 and Man5B.

FIG. 11A shows the results of the Control. FIG. 11B shows the results of Man5ATM1. FIG. 11C shows the results of Man5ATM2. FIG. 11D shows the results of Man5B. FIG. 11E shows the results of the combination of Man5ATM1 and Man5ATM2. FIG. 11F shows results of the combination of Man5ATM1 and Man5B. FIG. 11G shows the results of the combination of Man5ATM2 and Man5B.

FIG. 12A shows the results of the Control. FIG. 12B shows the results of Man5ATM1. FIG. 12C shows the results of Man5ATM2. FIG. 12D shows the results of Man5B. FIG. 12E shows the results of the combination of Man5ATM1 and Man5ATM2. FIG. 12F shows results of the combination of Man5ATM1 and Man5B. FIG. 12G shows the results of the combination of Man5ATM2 and Man5B.

FIG. 13A shows the results of the Control. FIG. 13B shows the results of Man5ATM1. FIG. 13C shows the results of Man5ATM2. FIG. 13D shows the results of Man5B. FIG. 13E shows the results of the combination of Man5ATM1 and Man5ATM2. FIG. 13F shows results of the combination of Man5ATM1 and Man5B. FIG. 13G shows the results of the combination of Man5ATM2 and Man5B.

FIG. 14A shows the results of the Control. FIG. 14B shows the results of Man5ATM1. FIG. 14C shows the results of Man5ATM2. FIG. 14D shows the results of Man5B. FIG. 14E shows the results of the combination of Man5ATM1 and Man5ATM2. FIG. 14F shows results of the combination of Man5ATM1 and Man5B. FIG. 14G shows the results of the combination of Man5ATM2 and Man5B.

DEFINITIONS

Figure 1:
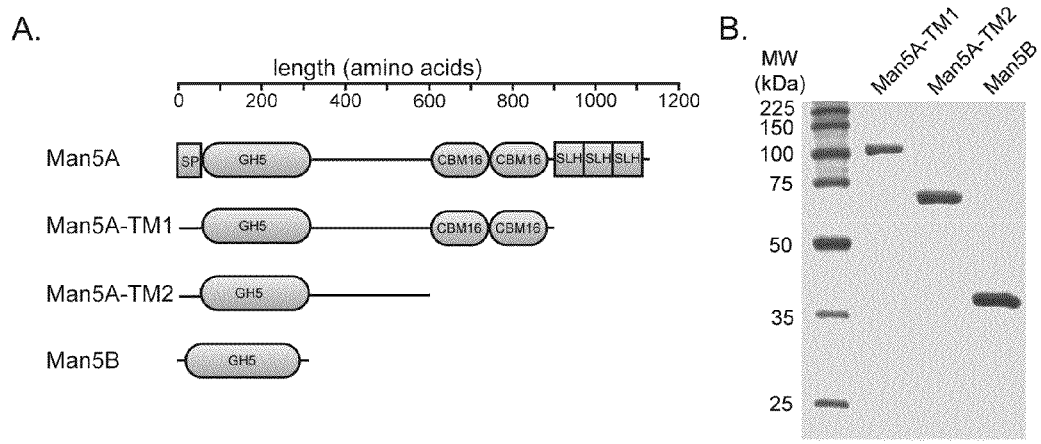
FIG. 1A provides schematics of the domain architecture for Man5A, Man5A-TM1, Man5A-TM2 and Man5B enzymes. The functional domains were assigned by using the Conserved Domains Database (CDD) search tool (NCBI website).
FIG. 1B shows the pooled elution fractions from cobalt affinity chromatography for Man5A-TM1, Man5A-TM2, and Man5B, as analyzed by 12% SDS-PAGE.

The terms "mannan endo-1,4-β-mannosidase," "endo-1,4-β-mannanase," "endo-β-1,4-mannase," "β-mannanase B," "β-1,4-mannan 4-mannanohydrolase," "endo-β-mannanase," "β-D-mannanase," and "1,4-β-D-mannan mannanohydrolase" refer to an enzyme capable of the random hydrolysis of 1, 4-β-D-mannosidic linkages in mannans, galactomannans and glucomannans (EC 3.2.1.78). In particular, endo-β-mannanases constitute a group of polysaccharases that degrade mannans and denote enzymes that are capable of cleaving polyose chains containing mannose units (i.e. are capable of cleaving glycosidic bonds in mannans, glucomannans, galactomannans and galactogluco-mannans). The "endo-β-mannanases of the present disclosure may possess additional enzymatic activities (e.g., endo-1,4-β-glucanase, 1,4-β-mannosidase, cellodextrinase activities, etc.).

"Mannans" are polysaccharides having a backbone composed of β-1,4-linked mannose; "glucomannans" are polysaccharides having a backbone of more or less regularly alternating β-1,4 linked mannose and glucose; "galactomannans" and "galactoglucomannans" are mannans and glucomannans with alpha-1,6 linked galactose sidebranches. These compounds may be acetylated. The degradation of galactomannans and galactoglucomannans is facilitated by full or partial removal of the galactose sidebranches. Further the degradation of the acetylated mannans, glucomannans, galactomannans and galactogluco-mannans is facilitated by full or partial deacetylation. Acetyl groups can be removed by alkali or by mannan acetylesterases. The oligomers that are released from the mannanases or by a combination of mannanases and alpha-galactosidase and/or mannan acetyl esterases can be further degraded to release free maltose by β-mannosidase and/or β-glucosidase.

The term "catalytic activity" or "activity" describes quantitatively the conversion of a given substrate under defined reaction conditions. The term "residual activity" is defined as the ratio of the catalytic activity of the enzyme under a certain set of conditions to the catalytic activity under a different set of conditions. The term "specific activity" describes quantitatively the catalytic activity per amount of enzyme under defined reaction conditions.

The term "thermostability" describes the property of a protein to withstand a limited heat exposure without losing the activity it possesses at lower temperatures (e.g., at the temperature where its activity is measurable).

The term "pH-stability" describes the property of a protein to withstand a limited exposure to pH-values significantly deviating from the pH where its stability is optimal (e.g., more than one pH-unit above or below the pH-optimum, without losing its activity under conditions where its activity is measurable).

The term "hemicellulose" refers to a polymer of short, highly-branched chains of mostly five-carbon pentose sugars (e.g., xylose and arabinose) and to a lesser extent six-carbon hexose sugars (e.g., galactose, glucose and mannose). Hemicelluloses may comprise, for example, xylan, glucuronoxylan, arabinoxylan, glucomannan, or xyloglucan. Non-limiting examples of sources of hemicellulose include grasses (e.g., switchgrass, Miscanthus), rice hulls, bagasse, cotton, jute, hemp, flax, bamboo, sisal, abaca, straw, leaves, grass clippings, corn stover, corn cobs, distillers grains, legume plants, sorghum, sugar cane, sugar beet pulp, wood chips, sawdust, and biomass crops (e.g., *Crambe*).

The term "renewable resources" refers to biomass substrates that are grown and harvested, like crops, straw, wood and wood products. The term "biological fuels" refers to solid, liquid, or gas fuel consisting of, or derived from biomass, like biodiesel, biogas, vegetable oil, bioethanol, biohydrogen, and the like.

The term "softwood" is used herein to refer to wood from conifers or the trees themselves. Softwood trees include narrow leafed trees such as evergreens, as well as wood from bald cypress and the larches. The mannan content of softwood is on the order of 10 to 15% by weight.

The term "hardwood" is used herein to refer to wood from non-monocot angiosperm trees or the trees themselves. Hardwood trees include broad-leafed trees such as oak, beech, ash, maple and cherry. Other examples of hardwood trees include holly, boxwood, teak, and mahogany. The mannan content of hardwood is on the order of 2 to 3% by weight.

DETAILED DESCRIPTION

The complete hydrolysis of (hetero) mannans into their component monosaccharides requires the synergistic action of endo-acting β-mannanases, exo-acting β-mannosidases, exo-acting β-glucosidases, α-galactosidases, and acetylmannan esterases (Moreira et al., Appl Microbiol Biotechnol, 79:165, 2008). Galactose and acetyl decorations are removed by the side-chain cleaving activities of α-galactosidases and acetylmannan esterases. The internal glycosidic linkages within the backbone of mannans are hydrolyzed into manno-oligosaccharides or gluco-manno-oligosaccharides by endo-β-1,4-mannanases, and then β-mannosidases and β-glucosidasesrelease mannose or glucose, respectively, from the nonreducing end.

Embodiments

The present disclosure relates to isolated bacterial endo-β-mannanase polypeptides such as *C. polysaccharolyticus* endo-β-mannanase 5B (Man5B), *C. polysaccharolyticus* endo-β-mannanase 5A (Man5A), or fragments thereof. The present disclosure also relates to isolated polynucleotides encoding the bacterial endo-β-mannanase polypeptides, as well as vectors and genetically modified host cells containing such isolated polynucleotides. The present disclosure further relates to compositions comprising an isolated endo-β-mannanase or enriched in such endo-β-mannanase. Moreover the present disclosure relates to methods for the production of a endo-β-mannanase, and methods for hydrolysis of a mannan-containing poly- or oligo-saccharides with such compositions.

Polypeptides

The present disclosure relates to isolated bacterial endo-β-mannanase polypeptides, or fragments thereof. In particular, the present disclosure provides *C. polysaccharolyticus* endo-β-mannanase 5B (Man5B) of SEQ ID NO: 31, *C. polysaccharolyticus* endo-β-mannanase 5A (Man5A) of SEQ ID NO: 27, or fragments thereof (e.g., Man5ATM1 of SEQ ID NO: 28 or Man5ATM2 of SEQ ID NO: 29). In some embodiments, the endo-β-mannanase has a sequence identity of at least 85%, preferably at least 90%, preferably at least 95%, or 100% to SEQ ID NO: 31, SEQ ID NO: 27, SEQ ID NO: 28, or SEQ ID NO: 29. In some preferred embodiments, the polypeptide is an endo-β-mannanase comprising the amino acid sequence of SEQ ID NO: 31, or a variant thereof having from one to 16 mutations while retaining wild type Man5B active site residues (e.g., E137 and E258 of SEQ ID NO: 31). In other embodiments, the polypeptide is an endo-β-mannanase comprising the amino acid sequence of SEQ ID NO: 27, or a variant thereof having from one to 53 mutations while retaining wild type Man5A active site residues (e.g., E177 and E285 of SEQ ID NO: 26). In still further embodiments, the polypeptide is a carbohydrate binding module (CBM) of Man5A, or a variant thereof with a sequence identity of at least 85%, preferably at least 90%, preferably at least 95%, or 100% to residues 614 to 743, residues 757 to 883, or residues 637 to 899 of SEQ ID NO: 26.

In some embodiments, the endo-β-mannanase polypeptides are produced recombinantly, while in others the endo-β-mannanases polypeptides are produced synthetically, or are purified from a native source (*C. polysaccharolyticus*).

In some embodiments, the endo-β-mannanase amino acid sequences and derivatives are produced as a N- and/or C-terminal fusion protein, for example to aid in extraction, detection and/or purification and/or to add functional properties to the endo-β-mannanase. Examples of fusion protein partners include, but are not limited to, glutathione-S-transferase (GST), 6×His, GAL4 (DNA binding and/or transcriptional activation domains), FLAG-, MYC-tags or other tags well known to anyone skilled in the art. In some embodiments, a proteolytic cleavage site is provided between the fusion protein partner and the protein sequence of interest to allow removal of fusion protein sequences. Preferably, the fusion protein does not hinder the activity of the endo-β-mannanase.

In some embodiments, the endo-β-mannanase is fused to a functional domain including a leader peptide, propeptide, binding domain and/or catalytic domain. Suitable binding domains include, but are not limited to, carbohydrate-binding domains (e.g., CBM) of various specificities, providing increased affinity to carbohydrate components present during the application of the endo-β-mannanase. Suitable enzymatically active domains possess an activity that supports the action of the endo-β-mannanase in producing the desired product. Non-limiting examples of catalytic domains include: cellulases, hemicellulases such as xylanase, exomannanases, glucanases, arabinases, galactosidases, pectinases, and/or other activities such as proteases, lipases, acid phosphatases and/or others or functional fragments thereof. Fusion proteins are optionally linked to the mannanase through a linker sequence that simply joins the endo-β-mannanase and the fusion domain without significantly affecting the properties of either component, or the linker optionally has a functional importance for the intended application.

Alternatively, the endo-β-mannanases described herein are used in conjunction with one or more additional proteins of interest. Non-limiting examples of proteins of interest include: hemicellulases, alpha-galactosidases, beta-galactosidases, lactases, beta-glucanases, endo-beta-1,4-glucanases, cellulases, xylosidases, xylanases, xyloglucanases, xylan acetylesterases, galactanases, exo-mannanases, pectinases, pectin lyases, pectinesterases, polygalacturonases, arabinases, rhamnogalacturonases, laccases, reductases, oxidases, phenoloxidases, ligninases, proteases, amylases, phosphatases, lipolytic enzymes, cutinases and/or other enzymes.

Polynucleotides

In another aspect, the disclosure provides an isolated and/or purified nucleic acid molecule encoding a bacterial endo-β-mannanase. In some embodiments, the isolated polynucleotide encodes *C. polysaccharolyticus* endo-β-mannanase 5B (Man5B) of SEQ ID NO: 31, *C. polysaccharolyticus* endo-β-mannanase 5A (Man5A) of SEQ ID NO: 27, or fragments thereof (e.g., Man5ATM1 of SEQ ID NO: 28 or Man5ATM2 of SEQ ID NO: 29). In other embodiments the isolated polynucleotide encodes a polypeptide having a sequence identity of at least 85%, preferably at least 90%, preferably at least 95%, or 100% to SEQ ID NO: 31, SEQ ID NO: 27, SEQ ID NO:28, SEQ ID NO: 29 or a carbohydrate binding module (CBM) of Man5A (e.g., residues 614 to 743, residues 757 to 883, or residues 637 to 899 of SEQ ID NO: 26). In some embodiments, the polynucleotide comprises the nucleic acid sequence of SEQ ID NO: 25, SEQ ID NO: 30, or a nucleic acid sequence that is at least 85% identical thereto or an effective fragment thereof.

Vectors and Host Cells

In order to produce a bacterial endo-β-mannanase, the DNA encoding the enzyme can be chemically synthesized from published sequences or obtained directly from host cells harboring the gene (e.g., by cDNA library screening or PCR amplification). In some embodiments, the endo-β-mannanase polynucleotide is included in an expression cassette and/or cloned into a suitable expression vector by standard molecular cloning techniques. Such expression cassettes or vectors contain sequences that assist initiation and termination of transcription (e.g., promoters and terminators), and generally contain a selectable marker.

The expression cassette or vector is introduced in a suitable expression host cell, which then expresses the corresponding endo-β-mannanase polynucleotide. Particularly suitable expression hosts are bacterial expression host genera including *Escherichia* (e.g., *Escherichia coli*), *Pseudomonas* (e.g., *P. fluorescens* or *P. stutzerei*), *Proteus* (e.g., *Proteus mirabilis*), *Ralstonia* (e.g., *Ralstonia eutropha*), *Streptomyces*, *Staphylococcus* (e.g., *S. carnosus*), *Lactococcus* (e.g., *L. lactis*), or *Bacillus* (*subtilis*, *megaterium*, *lichenifonnis*, etc.). Also particularly suitable are yeast expression hosts such as *Saccharomyces cerevisiae*, *Schizosaccharomyces pombe*, *Yarrowia lipolytica*, *Hansenula polymorpha*, *Kluyveromyces lactis* or *Pichia pastoris*. Especially suited are fungal expression hosts such as *Aspergillus niger*, *Chrysosporium lucknowense*, *Aspergillus* (e.g., *A. oryzae*, *A. niger*, *A. nidulans*, etc.) or *Trichoderma reesei*. Also suited are mammalian expression hosts such as mouse (e.g., NS0), Chinese Hamster Ovary (CHO) or Baby Hamster Kidney (BHK) cell lines. Other eukaryotic hosts such as insect cells or viral expression systems (e.g., bacteriophages such as M13, T7 phage or Lambda, or viruses such as Baculovirus) are also suitable for producing the endo-β-mannanases.

Promoters and/or signal sequences associated with secreted proteins in a particular host of interest are candidates for use in the heterologous production and secretion of endo-β-mannanases in that host or in other hosts. As an example, in filamentous fungal systems, the promoters that drive the genes for cellobiohydrolase I (cbh1), glucoamylase A (glaA), TAKA-amylase (amyA), xylanase (ex1A), the gpd-promoter cbh1, cbh11, endoglucanase genes EGI-EGV, Ce161B, Ce174A, egl1-egl5, gpd promoter, Pgk1, pkil, EF-1alpha, teff, cDNA1 and hex1 are particularly suitable and can be derived from a number of different organisms (e.g., *A. niger*, *T. reesei*, *A. oryzae*, *A. awamori* and *A. nidulans*). In some embodiments, the endo-β-mannanase polynucleotide is recombinantly associated with a polynucleotide encoding a suitable homologous or heterologous signal sequence that leads to secretion of the endo-β-mannanase enzyme into the extracellular (or periplasmic) space, thereby allowing direct detection of enzyme activity in the cell supernatant (or periplasmic space or lysate). Particularly suitable signal sequences for *Escherichia coli*, other Gram negative bacteria and other organisms known in the art include those that drive expression of the HlyA, DsbA, Pbp, PhoA, PelB, OmpA, OmpT or M13 phage GIII genes. For *Bacillus subtilis*, Gram-positive organisms and other organisms known in the art, particularly suitable signal sequences further include those that drive expression of the AprE, NprB, Mpr, AmyA, AmyE, BlaC, SacB, and for *S. cerevisiae* or other yeast, include the killer toxin, Bar1, Suc2, Mating factor alpha, Inu1A or Ggp1p signal sequence. Signal sequences can be cleaved by a number of signal peptidases, thus removing them from the rest of the expressed protein. In some embodiments, the rest of the endo-β-mannanases is expressed alone or as a fusion with other peptides, tags or proteins located at the N- or C-terminus (e.g., 6×His, HA or FLAG tags). Suitable fusions include tags, peptides or proteins that facilitate affinity purification or detection (e.g., 6×His, HA, chitin binding protein, thioredoxin or FLAG tags), as well as those that facilitate expression, secretion or processing of the target endo-β-mannanase. Suitable processing sites include enterokinase, STE13, Kex2 or other protease cleavage sites for cleavage in vivo or in vitro.

Endo-β-mannanase polynucleotides are introduced into expression host cells by a number of transformation methods including, but not limited to, electroporation, lipid-assisted transformation or transfection ("lipofection"), chemically mediated transfection (e.g., CaCl and/or CaP), lithium acetate-mediated transformation (e.g., of host-cell protoplasts), biolistic "gene gun" transformation, PEG-mediated transformation (e.g., of host-cell protoplasts), protoplast fusion (e.g., using bacterial or eukaryotic protoplasts), liposome-mediated transformation, *Agrobacterium tumefaciens*, adenovirus or other viral or phage transformation or transduction.

Alternatively, the endo-β-mannanases are expressed intracellularly. Optionally, after intracellular expression of the enzyme variants, or secretion into the periplasmic space using signal sequences such as those mentioned above, a permeabilisation or lysis step can be used to release the endo-β-mannanase into the supernatant. The disruption of the membrane barrier is effected by the use of mechanical means such as ultrasonic waves, pressure treatment (French press), cavitation or the use of membrane-digesting enzymes such as lysozyme or enzyme mixtures. As a further alternative, the polynucleotides encoding the endo-β-mannanase are expressed by use of a suitable cell-free expression system. In cell-free systems, the polynucleotide of interest is typically transcribed with the assistance of a promoter, but ligation to form a circular expression vector is optional. In other embodiments, RNA is exogenously added or generated without transcription and translated in cell free systems.

Degradation of Biomass to Mono- and Oligosaccharides

The endo-β-mannanases and host cells of the present disclosure find use in a variety of industrial applications (See, e.g., US 2008/0064064). For instance the endo-β-mannanases disclosed herein find use in biofuel production, food processing, textile cleaning and paper pulp bleaching.

Biofuel Production

The endo-β-mannanases of the present disclosure find use in the production of monosaccharides, disaccharides, and oligosaccharides as chemical or fermentation feedstocks from biomass for the production of ethanol, other products, or intermediates. The endo-β-mannanases are in the form of a crude fermentation broth with or without the cells removed or in the form of a semi-purified or purified enzyme preparation. Alternatively, a host cell of the present disclosure is used as a source of the variant in a fermentation process with the biomass.

Biomass can include, but is not limited to, plant material, municipal solid waste, and wastepaper. Polymannose-containing plant material includes but is not limited to palm kernel, coconut, konjac, locust bean gum, gum guar, soy beans. Suitable crop residue for production of biomass includes but is not limited to palm kernel meal, palm kernel expellers, copra meal, copra pellets and soy bean hulls. The predominant polysaccharide in the primary cell wall of biomass is cellulose, the second most abundant is hemicellulose, and the third is pectin. The secondary cell wall, produced after the cell has stopped growing, also contains polysaccharides and is strengthened through polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which helps stabilize the cell wall matrix.

Ethanol is produced by enzymatic degradation of biomass and conversion of the released saccharides to ethanol. This kind of ethanol is often referred to as bioethanol or biofuel. It is used as a fuel additive or extender in blends of from less than 1% and up to 100% (a fuel substitute). Accordingly the endo-β-mannanases of the present disclosure find use in the degradation of mannan in hemicellulose to aid in the liberation of mannose from biomass. The mannose in turn is used in the production of ethanol. In particular, the endo-β-mannanases of the present disclosure are placed in contact with a polymannose-containing material for the production of mannose and mannopolymers such as mannobiose, mannotriose, mannotetraose, mannopentaose, and/or mannohexaose. In a further preferred embodiment, the endo-β-mannanase is used in combination with other carbohydrases (e.g., glucanase, xylanase, alpha-galactosidase and/or cellulase) for more extensive hydrolysis of the plant material.

Food Processing

Several anti-nutritional factors limit the use of specific plant material in the preparation of animal feed and food for humans. Plant material containing oligomannans such as mannan, galactomannan, glucomannan and galactoglucomannan reduces the digestibility and absorption of nutritional compounds such as minerals, vitamins, sugars and fats by the animals. The negative effects are in particular due to the high viscosity of the mannopolymers and to the ability of the mannopolymers to adsorb nutritional compounds. These effects are reduced through the use of mannopolymer degrading enzymes, namely endo-β-mannanase enzymes, which permits a higher proportion of mannopolymer containing cheap plant material to be included in the feed resulting in a reduction of feed costs. Additionally, through the activity of the endo-β-mannanases, mannopolymers are broken down to simpler sugars, which can be more readily assimilated to provide additional energy. Accordingly, compositions comprising the endo-β-mannanases of the present disclosure are preferably used for processing and/or manufacturing of food or animal feed.

The endo-β-mannanases of the present disclosure are useful as additives to feed for monogastric animals such as poultry and swine, as well as for human food. In some embodiments, the endo-β-mannanases are used to pretreat the feed instead of as a feed additive. In some preferred embodiment, the endo-β-mannanases are added to or used to pretreat feed for weanling pigs, nursery pigs, piglets, fattening pigs, growing pigs, finishing pigs, laying hens, broiler chicks, and turkeys. In some embodiment, the endo-β-mannanases are added to or used to pretreat feed from plant material such as palm kernel, coconut, konjac, locust bean gum, gum guar, soy beans, barley, oats, flax, wheat, corn, linseed, citrus pulp, cottonseed, groundnut, rapeseed, sunflower, peas, and lupines.

Since the endo-β-mannanases of the present disclosure are thermostable enzymes, they find used in processes of producing pelleted feed in which heat is applied to the feed mixture before the pelleting step, as it is the case in most commercial pellet mills. The endo-β-mannanases are to the other feed ingredients in advance of the pelleting step or after the pelleting step to the already formed feed pellets.

In compositions comprising the endo-β-mannanases intended for food processing or as a feed supplement, the compositions optionally contain other substituents such as coloring agents, aroma compounds, stabilizers, vitamins, minerals, other feed or food enhancing enzymes and the like. This applies in particular to the so-called pre-mixes. Food additives according to this present invention may be combined with other food components to produce processed food products. The resulting, combined food additive is mixed in an appropriate amount with other food components such as cereal or plant proteins to form a processed food product.

Textile Cleaning

The endo-β-mannanases of the present disclosure find use in detergent compositions to facilitate the removal of mannopolymer containing stains/soils. In a preferred embodiment the endo-β-mannanases are used in detergent compositions in combination with other enzymes from the group of amylases, cellulases, lipases, pectinases, proteases and endoglucanases.

Detergent compositions of the present disclosure comprising the endo-β-mannanases are in any convenient form (e.g., a bar, a tablet, a powder, a granule, a paste or a liquid). A liquid detergent is generally aqueous, typically containing up to 70% water and 0-30% organic solvent(s), or non-aqueous component(s).

The detergent composition comprises one or more surfactants (e.g., non-ionic including semi-polar, anionic, cationic and/or zwitterionic). The surfactants are typically present at a level of from 0.1% to 60% by weight. When included, detergents typically contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid, or soap. When included, detergents typically contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl N-alkyl derivatives of glucosamine (glucamides).

Detergent compositions optionally comprise 0-65% of a detergent builder or complexing agent such as zeolite, diphosphate, triphosphate, phosphonate, carbonate, citrate, nitrilotriacetic acid, ethylenediaminetetraacetic acid, diethylenetriaminepentaacetic acid, alkyl- or alkenylsuccinic add, soluble silicates, or layered silicates. Detergent compositions optionally comprise one or more polymers such as carboxymethylcellulose (CMC), poly(vinylpyrrolidone), poly(ethylene glycol), poly(vinyl alcohol), poly(vinylpyridine-N-oxide), poly (vinylimidazole), polycarboxylates such as polyacrylates, maleic/acrylic acid copolymers, and lauryl methacrylate/acrylic acid copolymers. The detergent optionally comprises a bleaching system (e.g., hydrogen peroxide source) such as perborate or percarbonate, which may be combined with a peracid-forming bleach activator such as tetraacetylethylenediamine or nonanoyloxybenzenesulfonate. Alternatively, the bleaching system comprise peroxyacids of the amide, imide, or sulfone type.

In detergent compositions, the endo-β-mannanases are added in an amount corresponding to 0.01-100 mg of enzyme protein per liter of wash liquor, preferably 0.05-5 mg of enzyme protein per liter of wash liquor, in particular 0.1-1 mg of enzyme protein per liter of wash liquor.

Paper Pulp Bleaching

The endo-β-mannanases of the present disclosure find use in the enzyme aided bleaching of paper pulps such as chemical pulps, semi-chemical pulps, kraft pulps, mechanical pulps or pulps prepared by the sulfite method. In some embodiments, the pulps are chlorine free pulps bleached with oxygen, ozone, peroxide or peroxyacids. In some embodiments, the endo-β-mannanases are used in enzyme aided bleaching of pulps produced by modified or continuous pulping methods that exhibit low lignin contents. In some embodiments, the endo-β-mannanases are applied alone or preferably in combination with xylanase and/or endoglucanase and/or alpha-galactosidase and/or cellobiohydrolase enzymes.

Discussion

*Caldanaerobius polysaccharolyticus* (Lee et al., Int J System Evol Microbiol, 58:666, 2008), originally named *Thermoanaerobacterium polysaccharolyticum* (Cann et al., Int J System Evol Microbiol, 51:293, 2001), is a thermophilic bacterium isolated from a waste pile from a canning factory in Illinois, USA. It was demonstrated that the *C. polysaccharolyticus* genome encodes Man5A, a modular bifunctional mannanase/endoglucanase (Cann et al., J Bacteriol, 181:1643, 1999), and recently the structures of the individual carbohydrate binding modules (CBM) that occur in tandem in this enzyme have been solved both in the apo-form and also in complex with ligand (Bae et al., J Biol Chem, 283:12415, 2008). During development of the present disclosure, *C. polysaccharolyticus* was found to contain a second mannanase gene, man5B. Interestingly, the gene product Man5B lacks the CBMs and the surface layer homology (SLH) modules found in Man5A. The *C. polysaccharolyticus* Man5B hydrolyzes mannan containing polysaccharides and both manno- and cello-oligosaccharides. Furthermore, Man5B was found to act synergistically with Man5A-TM1, a derivative of Man5A, to release products from substrates such as beta-mannan and carboxymethyl cellulose (CMC). The kinetic parameters of Man5A-TM1, Man5A-TM2, and Man5B were determined on different substrates, and site directed mutagenesis was used to identify the critical residues involved in catalysis in Man5A and Man5B. The results provide herein provide insight into how *C. polysaccharolyticus* utilizes these enzymes in nutrient acquisition, especially from mannan-containing polysaccharides and how these enzymes can be utilized for biofuel production.

Deletion of the two family 16 carbohydrate binding modules (CBMs) from Man5A resulted in a significant loss of both mannanase and carboxymethyl cellulase (CMCase) activities (Cann et al., J Bacteriol, 181:1643, 1999). During development of the present disclosure, the influence of the CBM domains on Man5A catalytic activity with a variety of different oligosaccharide and polysaccharide substrates was assessed. When the two CBM domains were deleted from Man5A, catalytic activity with polysaccharides was drastically reduced. This indicates that the CBMs influence the catalytic activity of Man5A. This effect is consistent with results from previous studies which indicate that carbohydrate binding modules increase the catalytic activities of associated catalytic modules (Shoseyov et al., Microbiol Molecular Biol Rev, 70:283, 2006). CBMs are generally thought to influence catalytic activities of associated catalytic domains mainly on insoluble substrates. The results provided herein, however, indicate that the catalytic activities with soluble substrates (locust bean gum, guar gum, carboxymethyl cellulose, and glucomannan) were also increased by the presence of the CBMs. This observation had been made in connection with a xylanase (Kittur et al., FEBS Letters, 549:147, 2003), and is hereby extended to a mannanase.

Both truncation mutants of Man5A had no detectable hydrolytic activity with manno- or cello-oligosaccharides with a degree of polymerization (DP) less than 4, but cleaved cello- and manno-oligosaccharides from 4-6 DP. Conversely, Man5B cleaved shorter manno- and cello-oligosaccharides as small as DP of 2, in addition to the longer oligosaccharides. Man5A and Man5B both have catalytic domains that group within the glycoside hydrolase (GH) family 5 (CAZY website). Despite this similar domain grouping, the two proteins share relatively low amino acid sequence similarity (23% identity over 115 amino acids aligned). The differences in amino acid sequence between these two proteins has consequences for the catalytic activities of these enzymes, apparently accounting for the differences in substrate specificities and end product distributions for Man5A and Man5B. The observation that Man5A-TM1 and Man5A-TM2 released similar products from polysaccharides indicates that the two CBM domains do not influence the product distribution for Man5A and further indicate that end product distribution is largely determined by the GH5 catalytic module.

Both Man5A-TM1 and Man5A-TM2 are hereby shown to hydrolyze polysaccharides: locust bean gum, guar gum, β-mannan, CMC and glucomannan. The catalytic activity of Man5A-TM1 on glucomannan was the highest among the 5 polysaccharides. The results agree well with the data from crystal structural analysis for the two CBMs of Man5A. It was shown that the CBMs bind to both β-1,4-cello- and β-1,4-manno-oligosaccharides, and as confirmed in the present studies, glucomannan was predicted to be the natural substrate for the enzyme (Bae et al., J Biol Chem, 283:12415, 2008).

Interestingly, the hydrolytic activity of Man5A-TM1 for locust bean gum was considerably higher than that of β-mannan and guar gum. These results indicate that a lower degree of α-linked galactose substitution (mannose:galactose ratio of 4:1) found in locust bean gum (Moreira et al., Appl Microbiol Biotechnol, 79:165, 2008) promotes the hydrolysis of the mannan backbone, whereas the higher galactose substitution in guar gum (mannose:galactose ratio of 2:1) decreases the accessibility of substrates to the CBMs or active site of Man5A-TM1. Interestingly, C. polysaccharolyticus has been demonstrated to elaborate an enzyme with such activity alpha-galactosidase activity (King et al., J Agric Food Chem, 50:5676, 2002).

During the course of the substrate specificity analyses described herein, Man5B showed endo-1, 4-β-mannanase, 1,4-β-mannosidase and endo-1,4-β-endoglucanase activities. Though lacking a CBM, Man5B exhibited an extensive substrate specificity profile, and was able to cleave polysaccharides (locust bean gum, guar gum, β-mannan, CMC, glucomannan), manno-oligosaccharides (DP 2-5), cello-oligosaccharides (DP 3-6), galacto-manno-oligosaccharides ($GM_2$, $GM_3$), and pNP-substrates. The degree of hydrolysis of mannose-containing polysaccharides decreases with increasing substitution by galactose. For instance, the specific activity against locust bean gum (mannose:galactose ratio of 4:1) and guar gum (mannose:galactose ratio of 2:1) were 1400 and 310 IU/mg, respectively. This observation indicates that activity decreased with increasing galactose substitution and that the galactose residues obstruct accessibility to the mannan backbone. These results further indicate that β-mannanase activity is limited by the number of branched α-galactose residues in mannose-containing substrates (Aziz et al., BMC Genomics, 9:75, 2008). Interestingly, Man5B exhibited a higher activity with the heterogeneous polysaccharide glucomannan (mannose:glucose ratio of 3:2) compared to the linear homopolysaccharide β-mannan. This indicates that glucose molecules within the backbone chain of glucomannan represent significant determinants of substrate specificity.

Synergism was detected in the Man5A-TM1/Man5B and to some extent Man5A-TM2/Man5B binary mixtures with CMC and β-mannan as substrates. Accordingly, Man5B and Man5A are predicted to release different products from polysaccharides and that Man5A cleaves polysaccharides into oligosaccharides that are subsequently converted to mono- or disaccharides by Man5B. The solubility of guar gum and β-mannan was low, thus the accessibility of glycosidic bonds to enzymes is decreased. Some CBMs have been found to have "disruptive" activity on substrate, and promoting catalysis by increasing access to polysaccharides (Davies et al., Cur Opin Structural Biol, 15:637, 2005; and Vaaje-Kolstad et al., J Biol Chem, 280:11313, 2005). The hydrolytic activity of Man5A-TM1 was stimulated in presence of Man5A-TM2 with β-mannan as substrate, which is predicted to be attributable to the CBMs of Man5A-TM1 making the substrate more accessible.

Man5A has a putative N-terminal Sec-dependent signal peptide, which indicates that it is apparently secreted outside of the cell. Man5A also contains three SLH repeats in the C-terminal region, which indicates that it is apparently anchored to the cell surface (Matuschek et al., J Bacteriol, 176:3295, 1994). Together these observations indicate that Man5A is secreted by C. polysaccharolyticus and subsequently tethered to the outside of the cell surface. The data provided herein further indicate that the products of enzymatic hydrolysis of mannan polysaccharides by Man5A are relatively long manno-oligosaccharides. Thus, Man5A apparently cleaves polysaccharides into oligosaccharides in close proximity to the cell surface such that they are transferred into the cell by a membrane associated transport system (FIG. 8A). In fact, clustering with man5B in the genome of C. polysaccharolyticus is an ABC transporter predicted to serve this function (FIG. 8B). Man5B, which does not have a putative Sec-dependent signal peptide, is predicted to remain cytoplasmically located to cleave the transported oligosaccharides into mono- and disaccharides, which are subsequently metabolized.

In short, the biochemical characterization of the two thermostable β-mannanases described herein, provides guidance as to the synergistic use of Man5A and Man5B for the saccharification of mannan containing plant cell wall polysaccharides for subsequent biofuels production. Knowledge of the mechanism of action is not necessary in order to make and use the present disclosure.

EXPERIMENTAL

Abbreviations. carbohydrate binding module (CBM), cellobiose ($G_2$); cellotriose ($G_3$); cellotetraose ($G_4$); cellopentaose ($G_5$); cellohexaose ($G_6$); α-1,6-galactosyl-mannobiose ($GM_2$); α-1,6-galactosyl-mannotriose ($GM_3$); β-D-mannanase/endoglucanase (Man5B); mannobiose ($M_2$); mannotriose ($M_3$); mannotetraose ($M_4$); mannopentaose ($M_5$); mannohexaose ($M_6$); molecular weight cut off (MWCO); para-nitrophenol (pNP); carboxymethyl cellulose (CMC); surface layer homology (SLH).

Example 1

Materials and Methods

Materials. *Thermoanaerobacterium polysaccharolyticum* (ATCC strain no. BAA-17) was originally isolated from the waste pile of a canning factory in Hoopeston, Ill. (Cann et al., Int J System Evol Microbiol, 51: 293, 2001). Recently, the strain was reclassified under a new genus and given the name *Caldanaerobius polysaccharolyticus* (Lee et al., Int J System Evol Microbiol, 58: 666, 2008. *E. coli* JM109 and BL21-CODONPLUS™ (DE3) RIL competent cells and the PicoMaxx high fidelity PCR system were purchased from Stratagene (La Jolla, Calif.). The pGEM-T TA-cloning vector and GOTAQ® DNA polymerase were acquired from Promega (Madison, Wis.). The pET-28a vector and the pET-46b EK/LIC cloning kit were obtained from Novagen (San Diego, Calif.). The NdeI, XhoI, and DpnI restriction endonucleases were purchased from New England Biolabs (Ipswich, Mass.). The DNeasy Blood and Tissue kit and the QIAprep Spin Miniprep Kit were obtained from QIAGEN, Inc. (Valencia, Calif.). Talon Metal Affinity Resin was purchased from Clontech Laboratories, Inc. (Mountain View, Calif.). Amicon Ultra-15 centrifugal filter units with 10,000 MWCO (molecular cut-off) and 50,000 MWCO were obtained from Millipore (Billerica, Mass.).

Manno-oligosaccharides, cello-oligosaccharides, α-1,6-galactosyl-mannobiose ($GM_2$), α-1,6-galactosyl-mannotriose ($GM_3$), 1,4-β-D-mannan, and Konjac glucomannan were all obtained from Megazyme (Bray, Ireland). Sodium carboxymethyl cellulose (CMC) was purchased from Acros Organics (Geel, Belgium). Gel filtration standards were obtained from Bio-Rad (Hercules, Calif.). All other reagents were of the highest possible purity and purchased from Sigma-Aldrich (St. Louis, Mo.).

Cloning, expression, and purification of Man5A-TM1, Man5A-TM2 and Man5B. *C. polysaccharolyticus* was cultured in TYG medium and DNA was isolated from mid-log cultures and purified using the Qiagen DNeasy Blood and Tissue kit with an integrated RNase treatment step. The genome of *C. polysaccharolyticus* was partially sequenced by the W. M. Keck Biotechnology Center at the University of Illinois at Urbana-Champaign. A Newbler assembly was generated which is comprised of ½ plate of FLX PE 454 data and ½ plate of 8 kb paired-end GSFLX Titanium data using a Genome Sequencer instrument from 454 Life Sciences (Branford, Conn.). The partial genome sequence was uploaded onto the Rapid Annotation using Subsystem Technology (RAST) server (Aziz et al., BMC Genomics, 9:75, 2008). Auto-annotation of the *C. polysaccharolyticus* partial genome sequence identified ORF0760 as a gene predicted to encode a bifunctional β-D-mannanase/endoglucanase (Man5B). Man5A was previously identified in a recombinant phage library of *C. polysaccharolyticus* genomic DNA, which was screened for endoglucanase activity (Cann et al., J Bacteriol, 181:1643, 1999) and the full sequence of this gene was also identified in the partial genome sequence for *C. polysaccharolyticus*.

The DNA sequence corresponding to man5B was amplified by the PicoMaxx high fidelity PCR kit using genomic DNA as the template with the primer set Man5B-Forward and Man5B-Reverse (Table 1-1). The primers were engineered to incorporate a 5'-GACGACGACAAGA (SEQ ID NO: 54) extension in Man5B-F and a 5'-GAGGAGAAGCCCGGT (SEQ ID NO: 55) extension in Man5B-R, which facilitated subsequent directional cloning. The resultant man5B amplicon was then digested with T4 DNA polymerase exonuclease activity, annealed with a similarly digested pET-46b vector and introduced into *E. coli* JM109 by electroporation. Man5A-TM1 was amplified using genomic DNA as template with primers Man5A-TM1-F and Man5A-TM1-R (Table 1-1). The primer sets for Man5A-TM1 and Man5A-TM2 were designed to include 5'-NdeI and 3'-XhoI restriction sites for subsequent directional cloning. The resulting amplicons were then cloned into the pGEM-T vector via TA-cloning and subcloned in-frame with the hexahistidine ($His_6$) encoding sequence of a modified pET-28a expression vector via its NdeI-XhoI polylinker site. The truncated protein Man5A-TM2 originally named ManA-SLH-CBD was cloned as described in a previous study (Cann et al., J Bacteriol, 181: 1643, 1999). Expression of each of the resulting gene constructs yielded fusion proteins containing an N-terminal polyhistidine tag sequence to facilitate affinity purification via metal chelate chromatography. The resulting plasmid constructs pET46-Man5B, pET28a-Man5A-TM1, and pET-28a-Man5A-TM2 were sequenced to confirm the integrity of the cloned genes (W. M. Keck Center for Comparative and Functional Genomics at the University of Illinois at Urbana-Champaign).

TABLE 1-1

Oligonucleotide Primers Used For Cloning

| Gene | Direction | SEQ ID | Sequence (5'→3')[a] |
|---|---|---|---|
| Man5ATM1 | Forward | 32 | 5'-CATATGGCCGGGACTTCCGGTGATGGGCGC-3' |
| | Reverse | 33 | 5'-CTCGAGCTATACTTCAACGAGCGTGATATTATCG-3' |
| Man5ATM2 | Forward | 34 | 5'-CATATGGCCGGGACTTCCGGTGATGGGCGC-3' |
| | Reverse | 35 | 5'-CTCGAGCTACTTAACCGGCACGTTTACTGTAATGG-3' |
| Man5B | Forward | 36 | 5'-GACGACGACAAGATGAAAAAATATGGCTTTAACTTCCAATGG-3' |
| | Reverse | 37 | 5'-GAGGAGAAGCCCGGTTATACTCTATTCTCCACAAGCAAATC-3' |

[a]Oligonucleotide primers were synthesized by Integrated DNA Technologies (Coralville, IA).

The plasmid constructs were then introduced into *E. coli* BL-21 CodonPlus (DE3) RIL competent cells by heat shock, and grown overnight in lysogeny broth (LB) agar medium supplemented with ampicillin (100 µg/mL) and chloramphenicol (50 µg/mL) at 37° C. After 12 h, single colonies were selected and used to inoculate fresh LB (10 mL) supplemented with the antibiotics above at the same concentrations, followed by culturing with aeration for 8 h at 37° C. The pre-cultures were then inoculated into fresh LB (1 L) supplemented with ampicillin and chloramphenicol and the cultures were incubated at 37° C. with vigorous aeration (225 rpm/min). The cultures were grown to an optical density of 0.3 at 600 nm, and the temperature was shifted to 16° C. and gene expression was induced by the addition of 0.1 mM isopropyl β-D-thiogalactopyranoside (IPTG). After 16 h of growth, the cells were harvested by centrifugation (4000×g, 15 min, 4° C.), the cell pellets were then re-suspended in 30 mL lysis buffer (50 mM Tris-HCl, 300 mM NaCl, pH 7.0), and ruptured by two passages through an EmulsiFlex C-3 cell homogenizer from Avestin (Ottawa, Canada). The cell lysate was then clarified by centrifugation at 20,000×g for 30 min at 4° C. to remove cell debris. The lysate containing recombinant protein was then incubated at 65° C. for 30 min, and centrifuged at 20,000×g for 15 min at 4° C. to remove heat labile E. coli proteins. The recombinant proteins were then purified from the heat treated supernatant using the Talon Metal Affinity Resin according to the supplier's protocol, with the exception that Tris-based binding (50 mM Tris-HCl, 300 mM NaCl, pH 7.5), and elution (50 mM Tris-HCl, 300 mM NaCl, 250 mM Imidazole, pH 7.5) buffers were employed. Aliquots of eluted fractions were analyzed by sodium dodecyl sulfate-polyacrylamide gel electrophoresis (SDS-PAGE) and protein bands were visualized by staining with Coomassie brilliant blue G-250. Elution fractions were pooled and the proteins were then exchanged into protein storage buffer (50 mM Tris-HCl, 150 mM NaCl, pH 7.5) by three successive concentration and dilution cycles with Amicon Ultra-15 centrifugal filter units (Man5A-TM1, Man5A-TM2, 50,000 MWCO; Man5B, 10,000 MWCO). The UV absorbances of the protein solutions were recorded at 280 nm using a Nanoprop 1000 from Thermo Scientific (Waltham, Mass.) and the protein concentrations were calculated using the following extinction coefficients: Man5A-TM1, $\epsilon_{280\ nm}$=189 mM$^{-1}$ cm$^{-1}$; Man5A-TM2, $\epsilon_{280\ nm}$=113 mM$^{-1}$ cm$^{-1}$; Man5B, $\epsilon_{280\ nm}$=103 mM$^{-1}$ cm$^{-1}$.

Hydrolysis of para-nitrophenyl (pNP) linked sugars. The hydrolytic activity of Man5A-TM1, Man5A-TM2 and Man5B with para-nitrophenyl (pNP) linked substrates was assayed using a thermostated Cary 300 UV-Vis spectrophotometer from Varian Inc. (Palo Alto, Calif.). Fifteen different substrates were screened including: pNP-α-L-arabinopyranoside, pNP-α-L-arabinofuranoside, pNP-β-D-fucopyranoside, pNP-α-L-fucopyranoside, pNP-α-D-galactopyranoside, pNP-β-D-galactopyranoside, pNP-α-D-glucopyranoside, pNP-β-D-glucopyranoside, pNP-β-D-maltopyranoside, pNP-α-D-maltopyranoside, pNP-α-D-mannopyranoside, pNP-β-D-mannopyranoside, pNP-α-L-rhamnopyranoside, pNP-β-D-xylopyranoside, and pNP-β-D-cellobioside. Different pNP substrates (1.0 mM, final concentration) were incubated at 65° C. in the presence or absence of Man5A-TM1, Man5A-TM2 or Man5B (100 nM, final concentration) in citrate buffer (50 mM, pH 5.5) for 30 min and the rate of pNP release was determined by monitoring the absorbance at 400 nm continuously. The extinction coefficient of pNP at pH 5.5 was determined as 1636 M$^{-1}$ cm$^{-1}$.

Optimal temperature and pH for Man5B. The optimum temperature for Man5B was determined by incubating the protein (5 nM, final concentration) with pNP-β-D-mannopyranoside or pNP-β-D-cellobioside in citrate buffer (50 mM sodium citrate, pH 5.5) at temperatures ranging from 45-80° C. in increments of 5° C. The optimum pH for Man5B was determined with pNP-β-D-mannopyranoside and pNP-β-D-cellobioside at 65° C. Buffers of different pH values ranging from 3.0 to 10.0 in increments of 0.5 pH values (pH 3.0-6.0, citrate buffer: 50 mM; pH 6.5, phosphate-citrate buffer: 50 mM; pH 7.0-8.0, Tris-HCl buffer: 50 mM; pH 9.0-10.0, Gly-cine buffer: 50 mM) were employed. For both the pH and temperature optimum experiments, the release of pNP was followed by continuously monitoring the absorbance at 400 nm. Extinction coefficients were determined for para-nitrophenol (pNP) in each of the different buffers and the resulting values were used to calculate initial velocities from slopes of the changes in absorbance at 400 nm as a function of time.

Determination of kinetic properties for wild type and mutant Man5B with pNP-linked sugars. Kinetic properties of wild type and mutant Man5B were determined for pNP-β-D-mannopyranoside and pNP-β-D-cellobioside. The substrate concentrations ranged from 0.06 to 10 mM and reactions were performed at 65° C. in citrate buffer (50 mM sodium citrate, pH 5.5). The reactions were equilibrated to 65° C. using a thermostated Cary 300 UV-Vis spectrophotometer, and the reactions were initiated by the addition of wild type (5 nM, final concentration) or mutant (2 μM, final concentration) Man5B. The rate of pNP release was determined by continuously monitoring the absorbance at 400 nm. Initial rate data were then plotted against the substrate concentrations, and the values of the Michaelis-Menten constant ($K_M$) and the maximum velocity ($V_{max}$) were estimated from a nonlinear curve fit using GraphPad Prism v5.01 from GraphPad Software (San Diego, Calif.). The $k_{cat}$ was calculated as the quotient of the $V_{max}$ and the concentration of enzyme used in the reaction.

Hydrolysis of oligosaccharides by Man5A-TM1, Man5A-TM2 and Man5B. The capacity of Man5A-TM1, Man5A-TM2 and Man5B to hydrolyze oligosaccharides was assessed by incubating the enzymes with cello-oligosaccharides (cellobiose: $G_2$, cellotriose: $G_3$, cellotetraose: $G_4$, cellopentaose: $G_5$, cellohexaose: $G_6$), manno-oligosaccharides (mannobiose: $M_2$, mannotriose: $M_3$, mannotetraose: $M_4$, mannopentaose: $M_5$, mannohexaose: $M_6$), or galacto-manno-oligosaccharides (α-1,6-galactosyl-mannobiose: $GM_2$, α-1,6-galactosyl-mannotriose: $GM_3$) and measuring the products released by either high performance anion exchange chromatography (HPAEC) or thin layer chromatography (TLC).

For end point assays, the substrates (10 mg/mL) were independently incubated with Man5A-TM1, Man5A-TM2, or Man5B (0.5 μM, final concentration) in citrate buffer (50 mM sodium citrate, pH 5.5) (10 μL, final volume) at 65° C. After 12 h of incubation, two volumes of ethanol were added to the hydrolysates and then the mixtures were evaporated using a Savant DNA120 SPEEDVAC® Concentrator (Ramsey, Minn.), and the end products were re-suspended in 2.5 μL of ddH$_2$O. For TLC analysis, 0.5 μL of sample were spotted on Silica Gel 60 F$_{254}$ TLC plates from Merck (Whitehouse Station, N.J.). Sugar standards including mannose ($M_1$), glucose ($G_1$), manno-oligosaccharides ($M_2$-$M_4$) or cello-oligosaccharides ($G_2$-$G_4$) (2.5 μg each) were spotted onto TLC plates where appropriate. Products of enzyme reactions with cello-oligosaccharides were resolved by one ascent with a mobile phase consisting of 1-butanol/acetic acid/H$_2$O 10:5:1, (v/v/v) (Kurokawa et al., Appl Microbiol Biotechnol, 59:455, 2002). Products of enzyme reactions with manno-oligosaccharides or galactosyl-manno-oligosaccharides were resolved by one ascent with a mobile phase consisting of n-propanol/ethanol/water 7:1:2 (v/v/v) according to Megazyme's instructions. The plates were then visualized by spraying with a 1:1 (v/v) mixture of methanolic orcinol (0.1%, w/v) and sulfuric acid (10%, v/v), followed by heating at 75° C. for 10 min (Dodd et al., J Bacteriol, 191:3328, 2009). For HPAEC-PAD analysis, a SYSTEM GOLD® HPLC instrument from Beckman Coulter (Fullerton, Calif.) equipped with a CARBOPAC™ PA1 guard column (4×50 mm) and a CARBOPAC™ PA1 analytical column (4×250 mm) from Dionex Corporation (Sunnyvale, Calif.) and a COULOCHEM® III electrochemical detector from ESA Biosciences (Chelmsford, Mass.) was employed. The re-suspended hydrolysate was diluted 100-fold in ddH$_2$O and 30 uL was injected onto the column. The elution conditions for HPAEC were as follows: 0-25 min, 0-0.3 M sodium acetate gradient in 100 mM NaOH; 25-30 min, 0.3-1 M sodium acetate gradient in 100 mM NaOH; 30-50 min, 100 mM NaOH (Lee et al., J Chromatography, 720:137, 1996; and Weitzhandler et al., Analytical Biochem, 241:135, 1996). Monomeric mannose ($M_1$) and α-1,6-galactosyl-mannobiose ($GM_2$) were used as standards.

Determination of catalytic efficiencies for Man5A-TM1, Man5A-TM2, and Man5B with oligosaccharides. The catalytic efficiencies of Man5A-TM1, Man5A-TM2 and Man5B for manno-oligosaccharides ($M_2$-$M_6$), gluco-oligosaccharides ($G_2$-$G_6$), and galactosyl-manno-oligosaccharides ($GM_2$, $GM_3$) were determined by HPAEC using a published method (Matsui et al., J Biochem, 109:566, 1991). Reactions were prepared with oligosaccharide substrates (30 μM, final concentration) in citrate buffer (50 mM sodium citrate, pH 5.5) and were initiated by the addition of Man5A-TM1, Man5A-TM2 (0.3 μM, final concentration), or Man5B (3 nM, final concentration). The relationship between hydrolysis rate and oligosaccharide substrates concentration (0, 30, 60, 90 μM) was linear, therefore the substrate concentration of 30 μM should be well below $K_m$. A linear relationship was also observed between substrates depletion and hydrolysis time (0, 5, 10, 15 min), so the hydrolytic reactions were terminated at 5 min. The substrate concentrations at the beginning of the reaction [$S_0$] and at specified times [$S_t$] (5 min) during the reaction were fitted to equation 1 (Cartmell et al., J Biol Chem, 283:34403, 2008; and Charnock et al., J Biol Chem, 273:32187, 1998).

$$k=\ln[S_0]/[S_t], \text{where } k=(k_{cat}/K_m)([\text{enzyme}])(\text{time}) \quad \text{(equation 1)}$$

Hydrolysis of plant polysaccharides by Man5A-TM1, Man5A-TM2 and Man5B. To evaluate enzyme activity on polysaccharide substrates, Man5A-TM1, Man5A-TM2 and Man5B (3 nmol each) were spotted onto agar (1% w/v) plates with citrate buffer (50 mM sodium citrate, pH 5.5) containing various polysaccharides (guar gum, locust bean gum, glucomannan, β-mannan, CMC, xylan, or lichenan) at 0.2% (w/v) final concentration. The plates were then incubated at 65° C. for 3 h and stained by incubating with congo red (0.1% w/v) for 5 min, followed by destaining with 1 M NaCl (Teather et al., Appl Environ Microbiol, 43:777, 2006).

To provide a more quantitative assessment of the hydrolysis of polysaccharides substrates, a reducing sugar assay was employed. The polysaccharide substrates (0.5%, w/v) were incubated with the Man5A-TM1, Man5A-TM2, or Man5B (50 nM, final concentration) in citrate buffer (50 mM sodium citrate, pH 5.5) at 65° C. After 5 min of incubation, the reactions were terminated by heating at 100° C. for 10 min and then centrifuged at 13,000 rpm for 10 min, and the reducing end concentration in the supernatant was determined using the para-hydroxybenzoic acid hydrazide (PHBAH) method with glucose as a standard (Lever, Analytical Biochem, 47:273, 1972).

To assess the synergistic activities of Man5A-TM1, Man5A-TM2 and Man5B in the hydrolysis of polysaccharide substrates (locust bean gum, guar gum, glucomannan, β-mannan and CMC) the substrates (0.5% w/v) were incubated with each enzyme in citrate buffer (50 mM sodium citrate, pH 5.5) at 65° C. in a final reaction volume of 2.5 mL. The enzymes and enzyme mixtures analyzed for hydrolysis were as follows: 1, Man5A-TM1 (50 nM); 2, Man5A-TM2 (50 nM); 3, Man5B (50 nM); 4, Man5A-TM1 (25 nM) and Man5A-TM2 (25 nM); 5, Man5A-TM1 (25 nM) and Man5B (25 nM); 6, Man5A-TM2 (25 nM) and Man5B (25 nM). At regular time intervals (5, 10, 20, 30, 60 min), 100-4, aliquots were removed from reaction mixtures and the enzymes were inactivated by heating at 100° C. for 10 min. The concentration of reducing ends was then determined using the PHBAH method.

Amino acid sequence alignment. Multiple amino acid sequence alignments were constructed using ClustalW (align.genome.jp). The alignment file (.aln) was then uploaded onto ESPript (espript website and processed for black shading and square frame output.

Protein structure modeling. The protein structural models for Man5A-TM1 and Man5B were constructed using the ModWeb online server for protein structure modeling (modbase.compbio.ucsf.edu/ModWeb20-html/modweb.html). The template for the Man5A-TM1 model was the *Thermobifida fusca* KW3 β-mannanase (Man) (Protein Data Bank Accession No. 1BQC) (Hilge et al., Structure, 6:1433, 1998). Man5A-TM1 and the *T. fusca* Man share 23% amino acid sequence identity over the modeled region of the proteins (amino acids 41-292 for Man5A-TM1 and amino acids 10-255 for Man). The template for the Man5B model was the *Thermotoga maritima* MSB8 endoglucanase (Cel5B) (Protein Data Bank Accession No. 1VJZ). Man5B and Cel5B share 45% amino acid sequence identity over the modeled region of the proteins (amino acids 26-325 for Man5B and amino acids 38-338 for Cel5B). Graphical visualization of the structural models was coordinated using UCSF Chimera (UCSF Chimera website).

Site-directed mutagenesis. Mutagenesis was carried out using PCR-based QUIKCHANGE XL site-directed mutagenesis kit from Stratagene (La Jolla, Calif.) according to the manufacturer's instructions. Mutagenic primers with the desired mutation were designed using the QUIKCHANGE® Primer Design Program (Stratagene website) and are listed in Table 1-2). The DNA templates for the PCR amplifications were the pET28a-Man5A-TM1 plasmid and the pET46-Man5B plasmid for generation of the Man5A-TM1 and Man5B mutants, respectively. Following 18 cycles of PCR using Pfu Turbo, the PCR mixture was digested with DpnI at 37° C. for 12 h to remove the parental DNA, and the resulting DNA was transformed into competent *E. coli* JM109 cells through electroporation. The DNA was sequenced to confirm that there were no PCR-derived nucleotide changes except those introduced by the PCR primers. The mutated genes were then expressed to produce the mutant recombinant proteins. The expression and purification methods were as described above for wild-type Man5A-TM1 and Man5B.

TABLE 1-2

Oligonucleotide Primers Used For Mutagenesis

| Desired mutation[a] | Primer name[b] | SEQ ID | Primer Sequence (5'→3')[c] |
|---|---|---|---|
| Glu177Ala | Man5A-E177A-F | 38 | 5'-TCTGGTTTAA CACCATGAAT GCGCCTGGCT CGTCTA-3' |
| | Man5A-E177A-R | 39 | 5'-TAGACGAGCC AGGCGCATTC ATGGTGTTAA ACCAGA-3' |

TABLE 1-2-continued

Oligonucleotide Primers Used For Mutagenesis

| Desired mutation[a] | Primer name[b] | SEQ ID | Primer Sequence (5'→3')[c] |
|---|---|---|---|
| Glu177Gln | Man5A-E177Q-F | 40 | 5'-GTCTGGTTTA ACACCATGAA TCAGCCTGGC TCG-3' |
|  | Man5A-E177Q-R | 41 | 5'-CGAGCCAGGC TGATTCATGG TGTTAAACCA GAC-3' |
| Glu285Ala | Man5A-E285A-F | 42 | 5'-GTACGTGTTC ATGGAGGCAT ACGGCAAGGA TTACA-3' |
|  | Man5A-E285A-R | 43 | 5'-TGTAATCCTT GCCGTATGCC TCCATGAACA CGTAC-3' |
| Glu285Gln | Man5A-E285Q-F | 44 | 5'-CTTGTACGTG TTCATGGAGC AGTACGGCAA GGATTACAGC G-3' |
|  | Man5A-E285Q-R | 45 | 5'-CGCTGTAATC CTTGCCGTAC TGCTCCATGA ACACGTACAA G-3' |
| Glu137Ala | Man5B-E137A-F | 46 | 5'-TTTAAGCTTT GATCTCGTAA ATGCACCTCC TAATATCGGC C-3' |
|  | Man5B-E137A-R | 47 | 5'-GGCCGATATT AGGAGGTGCA TTTACGAGAT CAAAGCTTAA A-3' |
| Glu137Gln | Man5B-E137Q-F | 48 | 5'-CAAGTTTTTA AGCTTTGATC TCGTAAATCA GCCTCCTAAT ATCGGC-3' |
|  | Man5B-E137Q-R | 49 | 5'-GCCGATATTA GGAGGCTGAT TTACGAGATC AAAGCTTAAA AACTTGC-3' |
| Glu258Ala | Man5B-E258A-F | 50 | 5'-GAGTTAATGT GCACATAGGG GCATTTGGAT GCTTTAATAA GAC-3' |
|  | Man5B-E258A-R | 51 | 5'-GTCTTATTAA AGCATCCAAA TGCCCCTATG TGCACATTAA CTC-3' |
| Glu258Gln | Man5B-E258Q-F | 52 | 5'-GGAGTTAATG TGCACATAGG GCAGTTTGGA TGCTTTAATA AGACC-3' |
|  | Man5B-E258Q-R | 53 | 5'-GGTCTTATTA AAGCATCCAA ACTGCCCTAT GTGCACATTA ACTCC-3' |

[a]Residues were selected for mutagenesis following alignment of amino acid sequences for Man5A and Man5B with biochemically characterized enzymes.
[b]Primers were designed using the QuikChange ® Primer Design Program from Stratagene (La Jolla, CA) and were synthesized by Integrated DNA Technologies (Coralville, IA).
[c]Codons selected for introduction of site-specific mutations are underlined.

Circular dichroism. To ensure that the mutations in Man5A-TM1 and Man5B did not have large structural consequences for the proteins, the secondary structural elements were evaluated by circular dichroism (CD) scan. Wild-type Man5A-TM1, Man5B and the mutants (Man5A-TM1 E177A, Man5A-TM1 E177Q, Man5A-TM1 E285A, Man5A-TM1 E285Q, Man5B E137A, Man5B E137Q, Man5B E258A, Man5B E258Q) were incubated in phosphate buffer (10 mM $NaH_2PO_4$—$Na_2HPO_4$, pH 5.5) at 25° C. in a 0.1 cm path length cuvette, and the CD spectra from 260 nm to 190 nm were recorded at a scan rate of 50 nm $min^{-1}$ and a wavelength step of 0.1 nm using a J-815 circular dichroism (CD) spectropolarimeter from JASCO Inc. (Tokyo, Japan). The protein concentrations were 0.2 mg/mL, the spectra were accumulated 5 times per sample, and all samples were corrected for the baseline signal contributed by the buffer. Each protein was assayed in triplicate and the resulting CD spectra were uploaded onto the DichroWeb online server to identify the relative proportions of secondary structure elements (Lobley et al., Bioinformatics, 18:211, 2002).

TABLE 1-3

CD-Spectra Analysis of Mutant Man5ATM1 and Man5B

| Protein | α-helix (%) | β-sheet (%) | β-turn (%) | unordered (%) |
|---|---|---|---|---|
| Man5ATM1 WT | 43.1 ± 0.6[a] | 29 ± 0.5 | 8.2 ± 0.6 | 20.8 ± 1 |
| Man5ATM1 E177A | 11 ± 0.5 | 35 ± 0.8 | 23 | 30.5 ± 0.5 |
| Man5ATM1 E177Q | 12.1 ± 0.7 | 34 | 23.4 ± 0.7 | 31.1 ± 0.7 |
| Man5ATM1 E285A | 12 | 34 ± 1.0 | 23.3 ± 1.0 | 31 |

TABLE 1-3-continued

CD-Spectra Analysis of Mutant Man5ATM1 and Man5B

| Protein | α-helix (%) | β-sheet (%) | β-turn (%) | unordered (%) |
|---|---|---|---|---|
| Man5ATM1 E285Q | 12.8 ± 0.4 | 33.6 ± 0.5 | 22 ± 0.7 | 31.2 ± 0.4 |
| Man5B WT | 20 ± 1.1 | 25 ± 0.6 | 25.1 ± 1.2 | 30 ± 0.6 |
| Man5B E137A | 34.5 ± 0.3 | 18 | 20 ± 0.8 | 28 ± 0.8 |
| Man5B E137Q | 34 ± 1 | 18.4 ± 0.2 | 20.3 ± 0.6 | 28.1 ± 1.1 |
| Man5B E258A | 33 ± 1 | 18.6 ± 0.8 | 20.6 ± 0.8 | 28 |
| Man5B E258Q | 33.2 ± 0.4 | 20.3 ± 1.2 | 20.1 ± 0.2 | 28.2 ± 0.3 |

The experiments were performed in triplicate, and data are means ± standard deviations from the mean.

Results

Cloning and expression of Man5A derivatives and Man5B. The analysis of the genome sequence of *Caldanaerobius polysaccharolyticus* revealed the presence of two glycoside hydrolase (GH) family 5 genes that are predicted to encode enzymes with β-mannanase activity. Consequently, they were designated Man5A and Man5B. The modular architecture of Man5A was described in an earlier report (Cann et al., J Bacteriol, 181:1643-1651, 1999). Briefly, Man5A is composed of an N-terminal GH 5 catalytic domain, flanked at the C-terminus by a region of unknown function, followed by two family 16 carbohydrate binding modules (CBMs) in tandem, and then three surface layer homology (SLH) repeats. Amino-terminal to the catalytic domain is a predicted signal peptide. The polypeptide sequence of Man5A was deposited as GENBANK Accession No. AAD09354. During development of the present disclosure, two truncation mutants of Man5A were constructed to probe the importance of the SLH and CBM modules for Man5A hydrolytic activity on different mannan containing substrates (FIG. 1A). Man5A truncation mutant 1 (Man5A-TM1) was constructed to delete the three SLH repeats. An additional truncation mutant (Man5A-TM2) was constructed by deleting the CBMs and SLH repeats to facilitate comparison of the GH 5 catalytic modules of Man5A and Man5B (FIG. 1A). In addition, the full length gene for Man5B was also cloned. The three proteins were expressed in *E. coli* cells as N-terminal hexahistidine fusion proteins to facilitate protein purification. Following a two-step purification procedure involving heat denaturation of mesophilic host proteins and metal affinity chromatography, the three proteins were highly purified as determined by SDS-PAGE analysis (FIG. 1B). The molecular weights were calculated from the primary amino acid sequences and the values for Man5A-TM1 (98.3 kDa), Man5A-TM2 (66.5 kDa), and Man5B (39.2 kDa) were in good agreement with the molecular weights estimated by SDS-PAGE.

The coding region of full length Man5A is set forth as SEQ ID NO: 25. The full length amino acid sequence of Man5A including the signal peptide shown in is set forth as SEQ ID NO: 26. The amino acid sequence of the mature form of Man5A is set forth as SEQ ID NO: 27.

The amino acid sequence of the mature form of Man5A-TM1 is set forth as SEQ ID NO: 28. The amino acid sequence of the mature form of Man5A-TM2 is set forth as SEQ ID NO: 29.

The coding region of Man5B is set forth as SEQ ID NO: 30. The amino acid sequence of Man5B is set forth as SEQ ID NO: 31.

Screening for activity with pNP linked sugars. Man5B exhibited hydrolytic activity with pNP-β-D-mannopyranoside and pNP-β-D-cellobioside, the specific activities of which were 14.2 IU/mg and 11.3 IU/mg, respectively. However, Man5A-TM1 and Man5A-TM2 did not exhibit detectable activity with any of the pNP linked substrates that were screened. The temperature and pH optima for Man5B was determined with both pNP-β-D-mannopyranoside and pNP-β-D-cellobioside as substrates. The enzyme was active at temperatures ranging from 45-80° C. Interestingly, Man5B has different temperature optimum with the two pNP substrates. For pNP-β-D-cellobioside, the optimal temperature of the enzyme was around 65-70° C., and about 50% activity was retained at 80° C. The optimal temperature of Man5B against pNP-β-D-mannopyranoside was around 60-65° C. Man5B was active at a pH range of 4.5-7.0 and the optimal pH was around 5.5 with both of the pNP substrates. The optimum temperature and pH of Man5A are 65-75° C. and 5.8, respectively, as previously reported (Cann et al., J Bacteriol, 181: 1643-1651, 1999).

Figure 2:
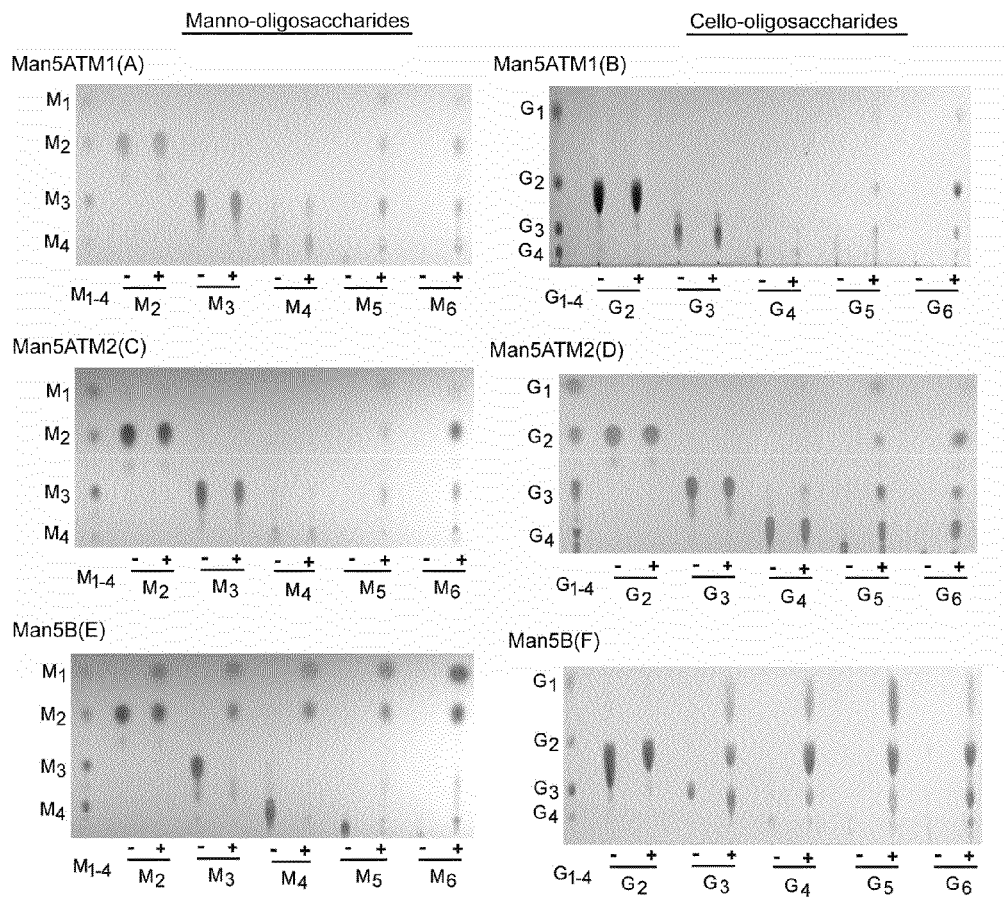
FIGS. 2A and 2B show the hydrolysis of β-1,4 linked manno-oligosaccharides and cello-oligosaccharides by Man5A-TM1.
FIGS. 2C and 2D show the hydrolysis of β-1,4 linked manno-oligosaccharides and cello-oligosaccharides by Man5A-TM2.
FIGS. 2E and 2F show the hydrolysis of β-1,4 linked manno-oligosaccharides and cello-oligosaccharides by Man5B. Each protein (0.5 µM final concentration) was incubated with either manno-oligosaccharides ($M_2$-$M_6$) or cello-oligosaccharides ($G_2$-$G_6$) (final concentration 10 mg/mL) at 65° C. for 12 h. The products were subsequently resolved by thin layer chromatography followed by staining with methanolic orcinol.

Man5A and Man5B exhibit different specificities with oligosaccharide substrates. To compare the substrate specificities of Man5A-TM1, Man5A-TM2, and Man5B, the three purified enzymes were screened for hydrolytic activity with manno- and cello-oligosaccharides. The enzymes were incubated with the oligosaccharides and the products of hydrolysis were resolved by thin layer chromatography. Man5A-TM1 and Man5A-TM2 were unable to hydrolyze mannobiose, mannotriose, and mannotetraose (FIGS. 2A and 2C) and likewise cellobiose, cellotriose, and cellotetraose (FIGS. 2B and 2D). However, as the degree of polymerization of the oligosaccharide increased to 5 and 6, both Man5A-TM1 and Man5A-TM2 hydrolyzed cello- and manno-oligosaccharides, releasing end-products that ranged from trisaccharides to monosaccharides (FIG. 2A-2D). In contrast to the Man5A constructs, Man5B exhibited hydrolytic activity with all of the oligosaccharides tested (FIGS. 2E and 2F) with the exception of cellobiose. All of the manno-oligosaccharides were converted to a mixture of mannobiose and mannose, while the cello-oligosaccharides were converted to shorter oligosaccharides. The products of hydrolysis of cello-oligosaccharides were not completely converted to cellobiose and glucose during the course of the reaction (FIG. 2E-2F).

To provide a more quantitative assessment of the substrate specificities of Man5A-TM1, Man5A-TM2, and Man5B, the catalytic efficiencies for the enzymes were determined with manno- and cello-oligosaccharides. There was no detectable activity for Man5A-TM1 and Man5A-TM2 with oligosaccharides of less than 3 degrees of polymerization (DP). However, for these Man5A derivatives, in general, the catalytic efficiency ($k_{cat}/K_M$) increased with substrates of larger DP (Table I). Furthermore, the $k_{cat}/K_M$ values for the two Man5A derivatives with manno-oligosaccharides were higher than that with cello-oligosaccharides (Table I).

TABLE I

Catalytic Efficiencies ($k_{cat}/K_m$) for Man5A-TM1,
Man5A-TM2 and Man5B with Various Substrates

| Substrate | Man5A-TM1[c] | Man5A-TM2[c] | Man5B[c] |
|---|---|---|---|
| pNP-cellobioside[a] | $(1.8 \pm 0.3) \times 10^{-2}$[d] | $(2.5 \pm 0.3) \times 10^{-2}$ | $25 \pm 2$ |
| pNP-β-D-mannopyranoside[a] | $(1.4 \pm 0.3) \times 10^{-2}$ | $(1.1 \pm 0.2) \times 10^{-2}$ | $1.6 \pm 0.1$ |
| mannobiose[a] | N.D. | N.D. | $0.23 \pm 0.03$ |
| mannotriose[a] | N.D. | N.D. | $0.27 \pm 0.05$ |
| mannotetraose[a] | $17 \pm 4$ | $11 \pm 1$ | $63 \pm 6$ |
| mannopentaose[a] | $33 \pm 3$ | $12 \pm 2$ | $(2.2 \pm 0.3) \times 10^2$ |
| mannohexaose[a] | $(1.2 \pm 0.2) \times 10^2$ | $28 \pm 8$ | $(2.7 \pm 0.7) \times 10^2$ |
| 6-galactosyl-mannobiose[a] | N.D. | N.D. | $1.5 \pm 0.2$ |
| 6-galactosyl-mannotriose[a] | N.D. | N.D. | $30 \pm 7$ |
| cellobiose[a] | N.D. | N.D. | N.D. |
| cellotriose[a] | N.D. | N.D. | $1.0 \pm 0.07$ |
| cellotetraose[a] | $11 \pm 2$ | $1.8 \pm 0.5$ | $1.4 \pm 0.2$ |
| cellopentaose[a] | $9.3 \pm 2$ | $2.2 \pm 0.3$ | $17 \pm 3$ |
| cellohexaose[a] | $20 \pm 2$ | $25 \pm 8$ | $43 \pm 3$ |

[a]The catalytic efficiencies ($k_{cat}/K_m$) for pNP-cellobioside, pNP-β-D-mannopyranoside, and oligosaccharides are reported as $mM^{-1} s^{-1}$.
[b]N.D. indicates that activity was below the detection limit for the assay.
[c]The experiments were performed in triplicate, and data are reported as means ± standard deviations from the mean.

Consistent with the results for the two Man5A derivatives, Man5B showed higher hydrolytic activity with manno-oligosaccharides as compared to cello-oligosaccharides, and the $k_{cat}/K_M$ also increased with substrates of larger DP. Compared to mannobiose, there was a substantial increase in $k_{cat}/K_M$ of Man5B with mannohexaose, and similar results were also observed for cello-oligosaccharides.

Figure 3:
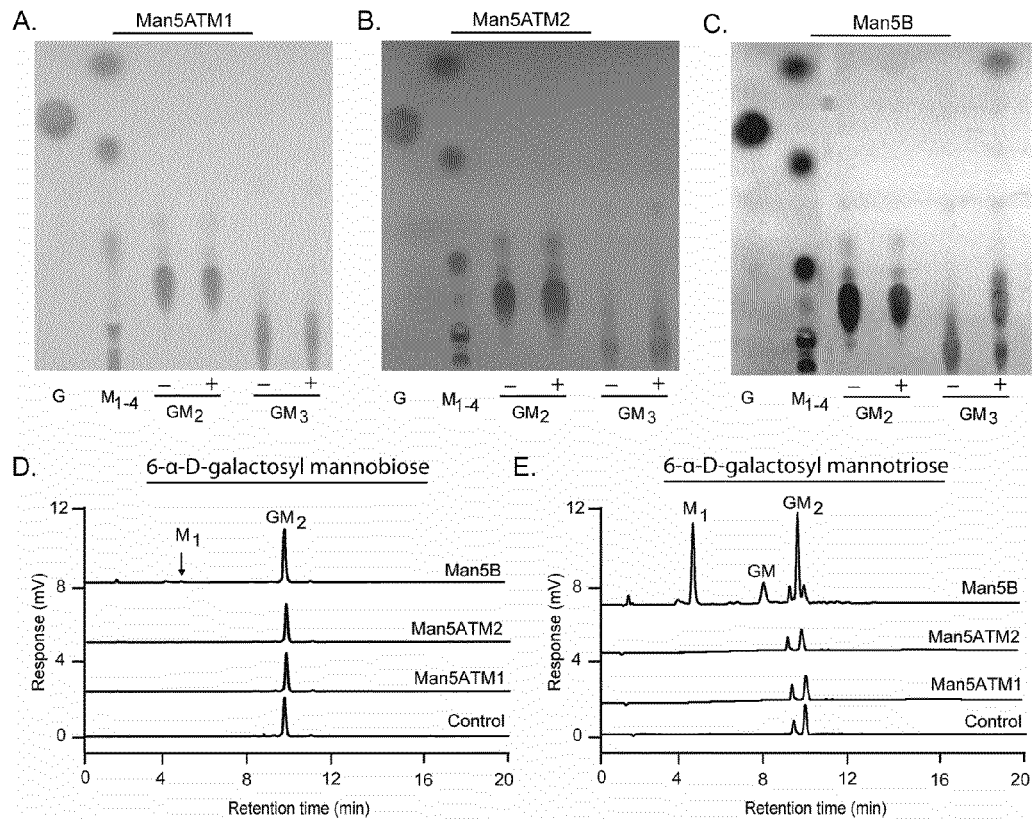
FIGS. 3A, 3B and 3C show the hydrolysis of galactomanno-oligosaccharides by Man5A-TM1, Man5A-TM2, and Man5B, respectively. Enzymes (0.5 µM each, final concentration) were incubated with 6-α-D-galactosyl mannobiose ($GM_2$) or 6-α-D-galactosyl mannotriose ($GM_3$) (10 mg/mL, final concentrations) at 65° C. for 12 h. The products of hydrolysis were resolved by TLC followed by staining with methanolic orcinol. Galactose (G) and manno-oligosaccharides ($M_{1-5}$) were used as standards. The minus sign indicates reactions in which the indicated enzyme was omitted and the plus sign indicates reactions in which the indicated enzyme was included.
FIGS. 3D and 3E show the hydrolysis of galactosyl mannobiose ($GM_2$) or 6-α-D-galactosyl mannotriose ($GM_3$), respectively. Man5A-TM1, Man5A-TM2, and Man5B (0.5 µM each, final concentration) were incubated with $GM_2$ or $GM_3$ (10 mg/mL, final concentration) at 65° C. for 12 h. The products of hydrolysis were analyzed by HPAEC. The peaks corresponding to mannose ($M_1$), 6-α-D-galactosyl mannose (GM), and 6-α-D-galactosyl mannobiose ($GM_2$) were determined by comparison of retention times to calibration standards.

Hydrolysis of substrates of increasing complexity. The capacity of the three enzymes to hydrolyze two substrates of medium complexity, galactosyl mannobiose ($GM_2$) and galactosyl mannotriose ($GM_3$) were investigated. Man5A-TM1 and Man5A-TM2 were incapable of releasing products from both $GM_2$ and $GM_3$ substrates (FIG. 3A-B, 3D-E). Man5B released GM and mannose products from $GM_2$, however this was only detectable by HPAEC analysis (FIG. 3D). Man5B was able to effectively release mannose and $GM_2$ from $GM_3$ (FIG. 3C, 3E). The catalytic efficiency of Man5B for $GM_2$ and $GM_3$ was also determined and the value for $GM_3$ was 20-fold higher than that for $GM_2$ (Table I). For hydrolysis of both $GM_3$ and $GM_2$ with Man5B, galactose was not detected among the products, indicating that Man5B only cleaves the β-1,4-bond between mannose residues, and does not cleave the α-1,6-bond between galactose and mannose (FIG. 3E).

Figure 4:
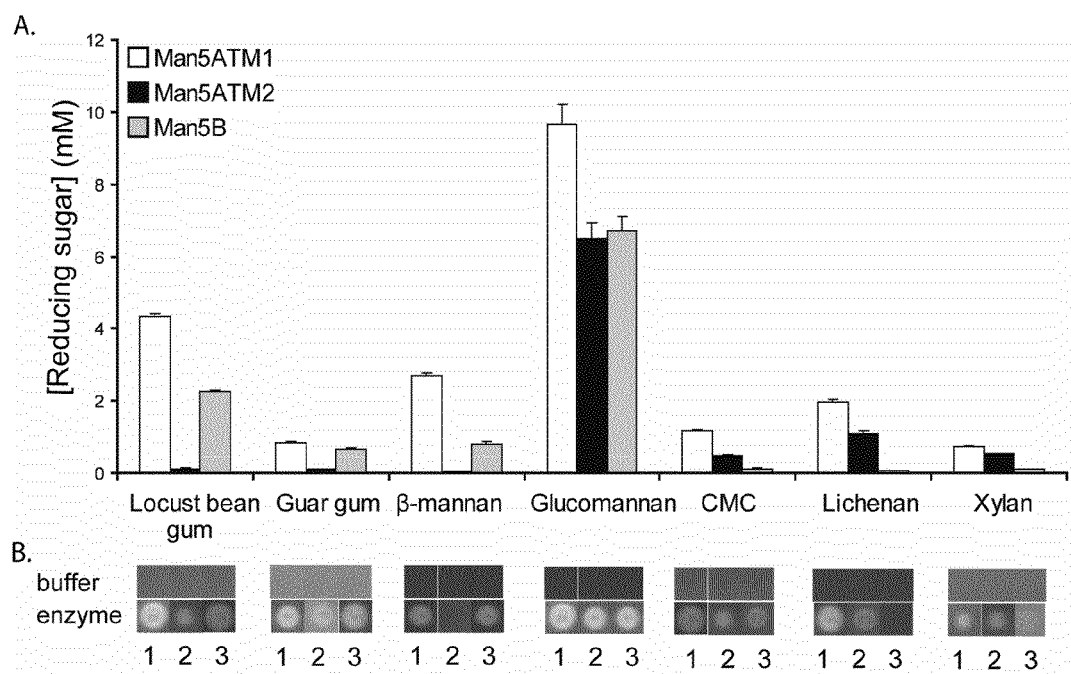
FIG. 4 shows the hydrolysis of polysaccharides by Man5A-TM1, Man5A-TM2 and Man5B.

Agar plates containing 0.1% of locust bean gum, guar gum, β-mannan, glucomannan, lichenan, or xylan was prepared. Purified Man5A-TM1, Man5A-TM2, or Man5B was then spotted onto each plate and the plates were incubated at 65° C. for 3 h, followed by staining with Congo red and destaining with 1M NaCl. In addition, hydrolysis of the artificial substrate carboxymethyl cellulose (CMC) was tested in a similar fashion. As compared to the control, zones of dye exclusion, suggesting hydrolysis of the polysaccharide, were observed with all of the enzyme-substrate combinations except for Man5A-TM2/β-mannan, Man5B/lichenan, and Man5B/xylan (FIG. 4B).

A more quantitative analysis of the hydrolytic activity of these enzymes with the polymeric substrates was performed by incubating each of the enzymes with each substrate in solution and determining the concentrations of reducing ends released. Man5A-TM1 exhibited hydrolytic activity with each of the polymeric substrates, although the highest activity was found with glucomannan (FIG. 4A). The hydrolytic activity for Man5A-TM2 was highly reduced with many of the substrates, especially locust bean gum and β-mannan, as compared to Man5A-TM1. Man5A-TM2, however, maintained relatively high activity with glucomannan as a substrate (FIG. 4A). This indicates that the carbohydrate binding modules that are present in Man5A-TM1, but absent in Man5A-TM2, are generally important for the hydrolytic activity of Man5A with polysaccharide substrates. Man5B exhibited considerable differences in substrate specificity as compared to the two Man5A derivatives, with low activity when incubated with carboxymethyl cellulose, lichenan, or xylan from oat spelts (FIG. 4A). The amount of reducing ends released by Man5A-TM2 and Man5B were similar with glucomannan, however, Man5B had much higher activity with locust bean gum, guar gum, and β-mannan as substrates. This indicates that although Man5A-TM2 and Man5B are similar, in that they lack carbohydrate-binding modules, there are other differences in the catalytic modules that confer different substrate specificities to the two enzymes.

To evaluate the product distribution following hydrolysis of polysaccharide substrates with Man5A-TM1, Man5A-TM2, or Man5B, the enzymes were incubated with guar gum, locust bean gum, glucomannan, β-mannan, or carboxymethyl cellulose and the products of hydrolysis were analyzed by HPAEC. The results indicated that only relatively long oligosaccharides (DP greater than 3) were released from polysaccharides incubated with Man5A-TM1 (locust bean gum, guar gum, β-mannan, glucomannan, carboxymethyl cellulose) and Man5A-TM2 (glucomannan and β-mannan) (FIGS. 10-14). Conversely, when Man5B was incubated with the various polysaccharides, the product distribution was highly enriched for shorter oligosaccharides with mannose and mannobiose being the predominant products (FIGS. 10-14). These results indicate that Man5A and Man5B have distinct differences in the products that they release from polysaccharides with Man5A releasing longer oligosaccharides and Man5B releasing shorter oligosaccharides.

Figure 5:
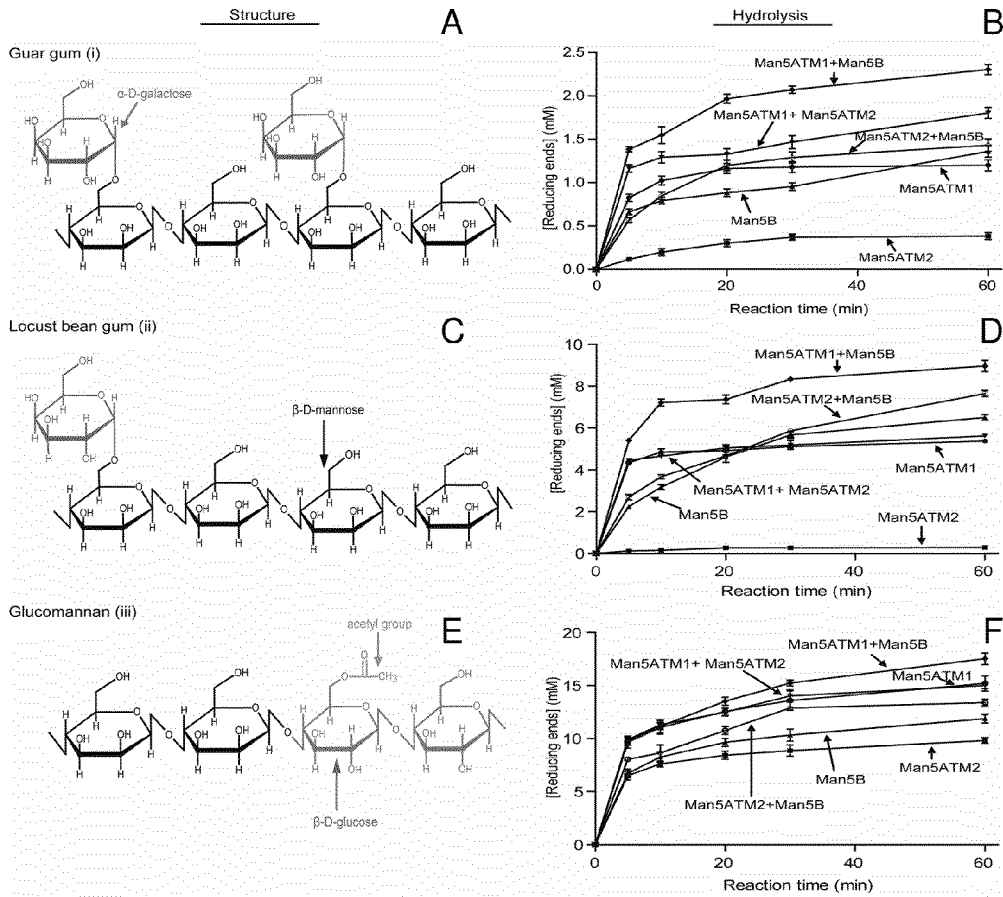
FIG. 5 shows the time course of polysaccharide hydrolysis by Man5A-TM1, Man5A-TM2 and Man5B. For each substrate, the chemical structure is indicated on the left, and the reducing sugars released following incubation of the substrate with enzyme is indicated on the right: guar gum (FIGS. 5A and 5B); locust bean gum (FIGS. 5C and 5D); glucomannan (FIGS. 5E and 5F); beta-mannan (FIGS. 5G and 5H); and CMC (FIGS. 5I and 5J). For the hydrolysis reactions, the enzyme or combination of enzymes was incubated with the appropriate substrate (0.5% w/v) in citrate buffer (50 mM, pH 5.5) at 65° C. At regular time intervals (0, 5, 10, 20, 30, 60 min) aliquots were removed for analysis of reducing ends released and HPAEC analysis as described in the experimental procedures. For reactions with a single enzyme, the final enzyme concentration was 50 nM and for reactions with two enzymes, the final enzyme concentration was 25 nM each of the two enzymes.
Figure 5:
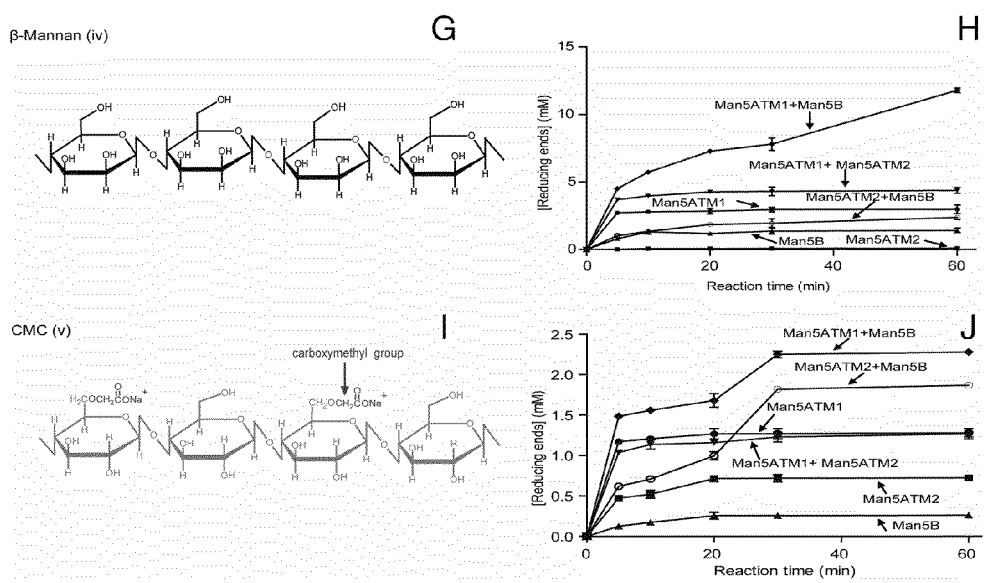

Synergistic activities of Man5A derivatives and Man5B. The *C. polysaccharolyticus* enzymes were tested for synergistic activity. The enzymes were incubated independently or in binary combinations with guar gum, locust bean gum, glucomannan, β-mannan, or CMC as substrate, and the concentration of reducing ends released was followed over time (FIG. 5). In addition, an aliquot of each reaction mixture from all substrate-enzyme combinations was removed at the 1 h time point, and the product composition was analyzed by HPAEC (FIGS. 10-14). The total concentration of enzyme in each of the reactions was maintained at 50 nM.

In the case of locust bean gum, glucomannan and CMC, the activity of Man5A-TM1 was not influenced by addition of Man5A-TM2 to the reaction mixture. In the case of guar gum as the substrate, the release of reducing ends in the presence of the two enzymes was additive. Interestingly, the release of reducing ends by Man5A-TM1 was stimulated in the presence of Man5A-TM2 using β-mannan as the substrate, such that product release by Man5A-TM1 was enhanced in the very similar (FIG. 6C), indicating that there were no large differences in the secondary structures between the wild type and mutant proteins.

To explore whether the mutations influenced the catalytic activity for Man5A-TM1, the specific activities of the four mutants were tested with locust bean gum, guar gum, β-mannan, glucomannan and CMC. The hydrolytic activities of the E177A, E1771Q, E285A, and E285Q mutants were all markedly decreased as compared to the wild type Man5A-TM1 (Table II). These data indicate that the two amino acid residues, E177 and E285 are important for catalysis in Man5A-TM1.

TABLE II

Specific Activities Of Wild Type And Mutant Man5A-TM1 For Natural Substrates.

| Enzyme | Locust bean gum$^{a,b}$ | Guar gum$^{a,b}$ | CMC$^{a,b}$ | β-mannan$^{a,b}$ | Glucomannan$^{a,b}$ |
|---|---|---|---|---|---|
| Man5A-TM1 | $(1.4 \pm 0.04) \times 10^3$ | $(3.1 \pm 0.3) \times 10^2$ | $(1.3 \pm 0.09) \times 10^2$ | $(6.9 \pm 0.6) \times 10^2$ | $(2.4 \pm 0.06) \times 10^3$ |
| Man5A-TM1 E177A | $3.9 \pm 1$ | N.D.$^c$ | N.D. | $1.1 \pm 0.3$ | $3.7 \pm 1.2$ |
| Man5A-TM1 E177Q | $3.1 \pm 0.2$ | $0.15 \pm 0.05$ | $(5.9 \pm 3) \times 10^{-2}$ | $2.1 \pm 0.1$ | $2.6 \pm 0.4$ |
| Man5A-TM1 E285A | $0.69 \pm 0.1$ | N.D. | N.D. | $0.40 \pm 0.1$ | $0.78 \pm 0.3$ |
| Man5A-TM1 E285Q | $3.1 \pm 0.5$ | $(8.1 \pm 3) \times 10^{-2}$ | $(5.0 \pm 2) \times 10^{-2}$ | $0.20 \pm 0.1$ | $1.1 \pm 0.2$ |

Figure 14:
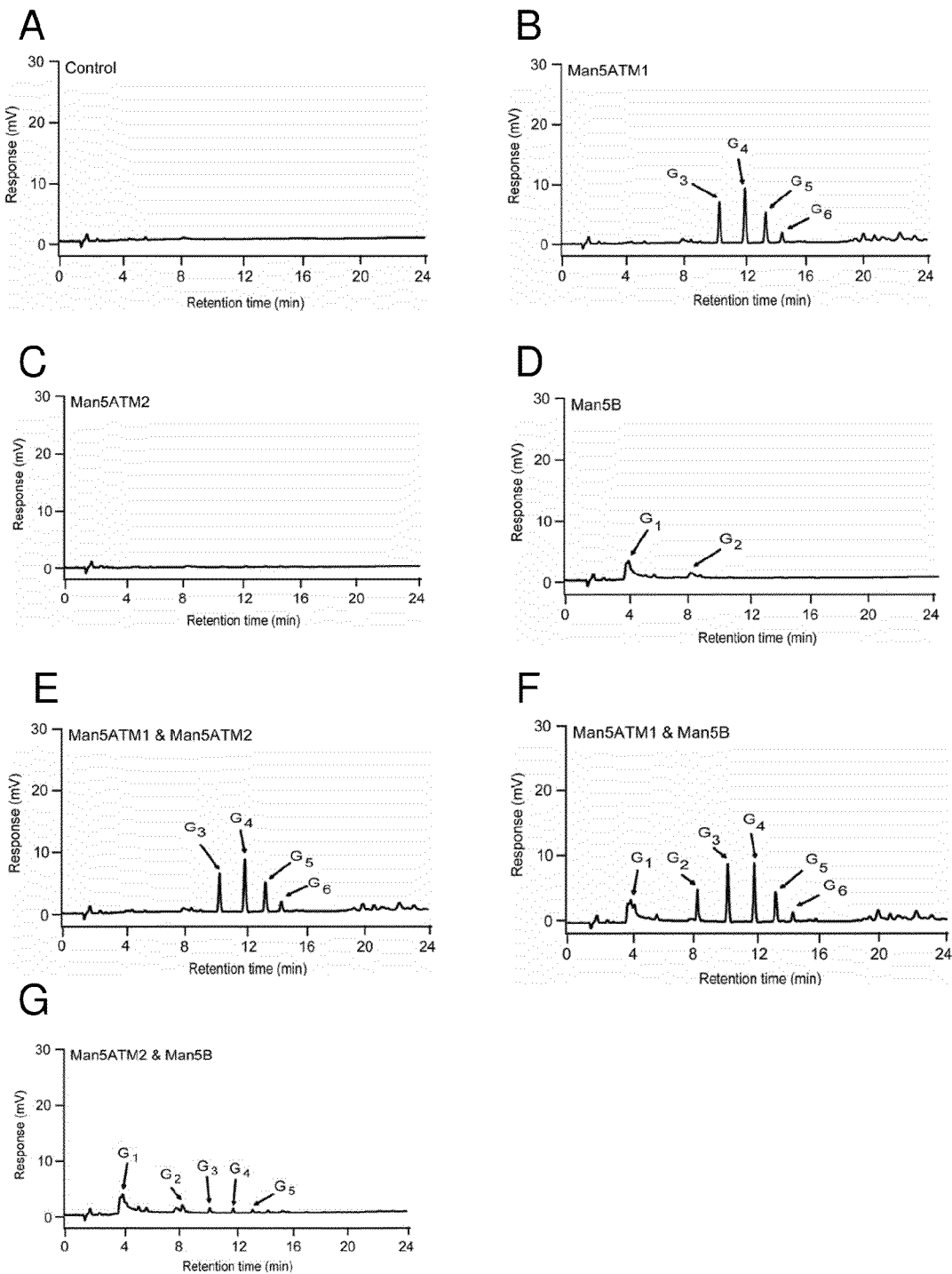
FIGS. 14A-G provides results of HPLC analysis of CMC hydrolysis by Man5ATM1, Man5ATM2 and Man 5B. In CMC hydrolysis reactions, the respective enzymes or combinations thereof were incubated with the substrate (0.5% w/v) in citrate buffer (50 mM, pH 5.5) at 65° C. for 1 h. The products were analyzed by HPAEC. For reactions with a single enzyme, the final enzyme concentration was 50 mM and for reactions with two enzymes, the final enzyme concentration was 25 nM of each enzyme. The peaks corresponding to glucose ($G_1$), cellobiose ($G_2$), cellotriose ($G_3$), cellotetraose ($G_4$), cellopentaose ($G_5$), and cellohexaose ($G_6$) are indicated by arrows.

$^a$The specific activities are reported as μmol min$^{-1}$ mg$^{-1}$.
$^b$The experiments were performed in triplicate, and data are reported as means ± standard deviations from the mean.
$^c$N.D. indicates that activity was below the detection limits for the assay.

presence of Man5A-TM2. The activity of Man5A-TM1 was also studied in the presence of Man5B. The release of reducing ends from guar gum and locust bean gum by Man5A-TM1 in the presence of Man5B was additive. However, Man5A-TM1 and Man5B acted synergistically to release reducing ends from CMC and β-mannan (FIGS. 5H and 5J). This synergistic activity was confirmed by HPAEC analysis for hydrolysis of β-mannan (FIG. 13, Man5A-TM1, Man5B, and Man5A-TM1/Man5B) and CMC (FIG. 14, Man5A-TM1, Man5B, and Man5A-TM1/Man5B).

Figure 6:
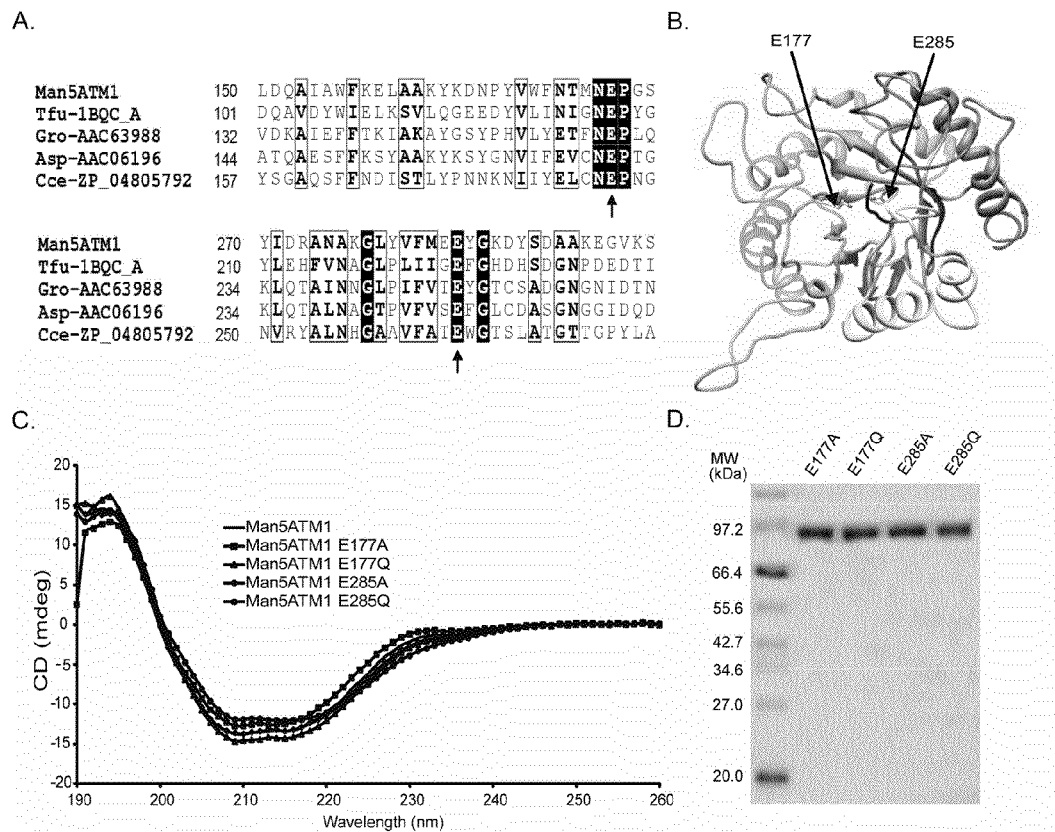
FIG. 6 shows the putative active site residues for Man5A-TM1 and activity of active site mutants.
Figure 7:
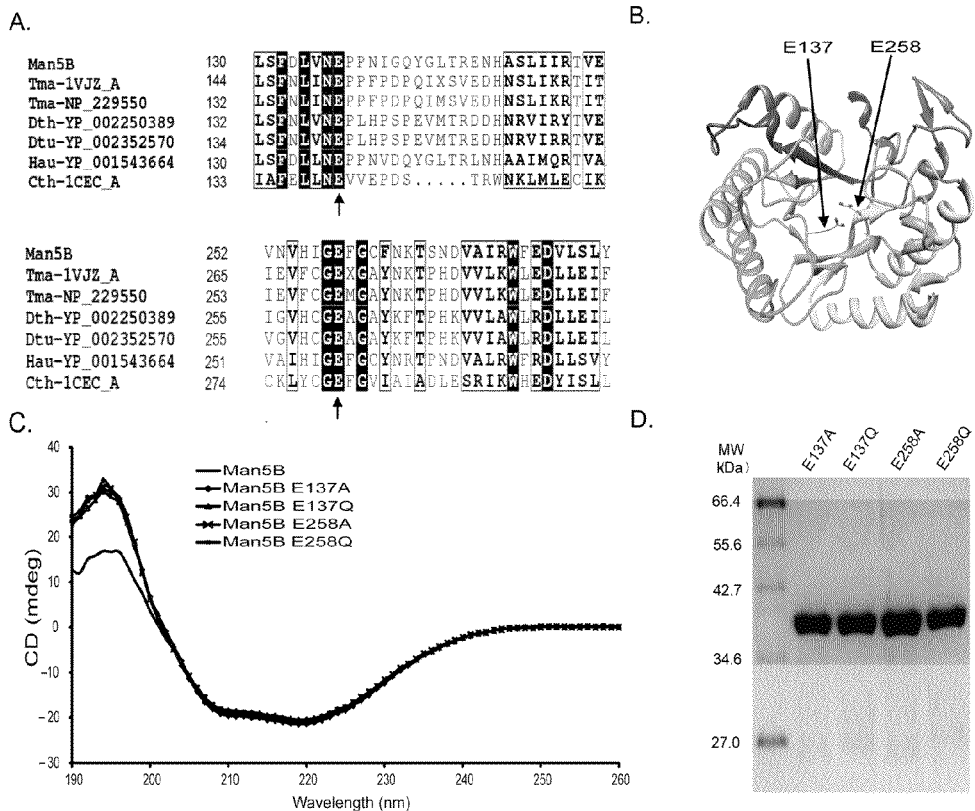
FIG. 7 shows the putative catalytic residues for Man5B and activity of active site mutants.

Mutational analysis to identify catalytic residues in Man5A and Man5B. To identify active site residues for Man5A, amino acid sequence alignments were constructed and a three-dimensional homology model was generated based upon the available crystal structure of a β-mannanase from *Thermobifida fusca* (Protein Databank Accession No. 1BQC) (Hilge et al., Structure, 6:1433, 1998). The sequence alignments and the homology model revealed the presence of two potential catalytic residues E177 and E285 in Man5A (FIGS. 6A and 6B). To determine whether these predicted active site residues were important for catalysis, Man5A-TM1 E177 and Man5A-TM1 E285 were independently changed to glutamine and alanine. The mutant proteins were expressed and purified and the resulting mutant proteins were highly purified (FIG. 6D). To ensure that these mutations did not lead to gross structural changes in the protein, the secondary structural elements of the proteins were analyzed by circular dichroism spectropolarimetry. The CD spectra for the wild type Man5A-TM1 and the four mutant proteins were To identify active site residues important for catalysis in Man5B, amino acid alignments were constructed and a three-dimensional homology model was generated based on the available crystal structure for the *Clostridium thermocellum* endoglucanase CelC (Protein Databank Accession No. 1OEC) (Dominguez et al., Nature Structural Mol Biol, 2:569, 1995; and Navas et al., Biochem Biophy Res Comm, 189: 807, 1992). The sequence alignments revealed the presence of two putative catalytic residues, E137 and E258 in Man5B (FIG. 7A-B). To determine whether these two residues were important for catalysis in Man5B, the two residues were mutated to alanine or glutamine by site-directed mutagenesis. The mutant proteins were expressed and purified and the resulting proteins were highly purified (FIG. 7D). Similar to the studies for Man5A, the mutant proteins were evaluated to determine whether these mutations induced any large changes in the secondary structural elements of the protein. The spectra for the wild type and mutant proteins were quite similar (FIG. 7C), indicating that the mutations did not cause any large structural changes in the protein.

Next, to test whether the mutations introduced in Man5B had any effects on the catalytic activity of this enzyme, the catalytic parameters for the wild type and mutant enzymes were determined using pNP-β-D-cellobioside and pNP-β-D-mannopyranoside as substrates. For the mutants which exhibited very low rates, the $k_{cat(apparent)}$ was determined at 10 mM substrate concentration. As shown in Table III, compared to the wild type the hydrolytic activities of the four mutant proteins were severely decreased with both pNP-β-D-cellobioside and pNP-β-D-mannopyranoside as substrates. These data indicate that both E137 and E258 are important for catalysis in Man5B.

TABLE III

Kinetic Parameters For Wild Type And Mutant Man5B with pNP Linked Sugars.

| Substrate | Enzyme | $k_{cat}$ (s$^{-1}$)[a] | $K_m$ (mM)[a] | $k_{cat}/K_m$ (mM s$^{-1}$)[a] | $^r k_{cat}$ (%)[b] |
|---|---|---|---|---|---|
| pNP-β-D-Cellobiose | Man5B | 2.4 ± 0.1 | (9.7 ± 1) × 10$^{-2}$ | 25 ± 2 | 100 |
| | Man5B E137A | (1.1 ± 0.4) × 10$^{-2}$ | N.D.[c] | N.D. | 0.48 |
| | Man5B E137Q | (4.7 ± 1) × 10$^{-2}$ | (2.9 ± 0.9) × 10$^{-1}$ | (1.6 ± 0.6) × 10$^{-1}$ | 1.96 |
| | Man5B E258A | (1.1 ± 0.1) × 10$^{-2}$ | N.D. | N.D. | 0.55 |
| | Man5B E258Q | (1.2 ± 0.4) × 10$^{-2}$ | N.D. | N.D. | 0.62 |
| pNP-β-D-mannopyranoside | Man5B | 42 ± 3 | 26 ± 4 | 1.6 ± 0.1 | 100 |
| | Man5B E137A | (1.9 ± 0.1) × 10$^{-2}$ | N.D. | N.D. | 0.04 |
| | Man5B E137Q | (1.8 ± 0.6) × 10$^{-2}$ | N.D. | N.D. | 0.04 |
| | Man5B E258A | (1.8 ± 0.3) × 10$^{-2}$ | N.D. | N.D. | 0.04 |
| | Man5B E258Q | (1.2 ± 0.2) × 10$^{-2}$ | N.D. | N.D. | 0.03 |

[a] The experiments were performed in triplicate, and data are reported as means ± standard deviations from the mean.
[b] $^r k_{cat}$ means residual $k_{cat}$.
[c] N.D. $K_m$ could not be measured as the maximum concentration of soluble substrate was <<$K_m$.

Figure 8:
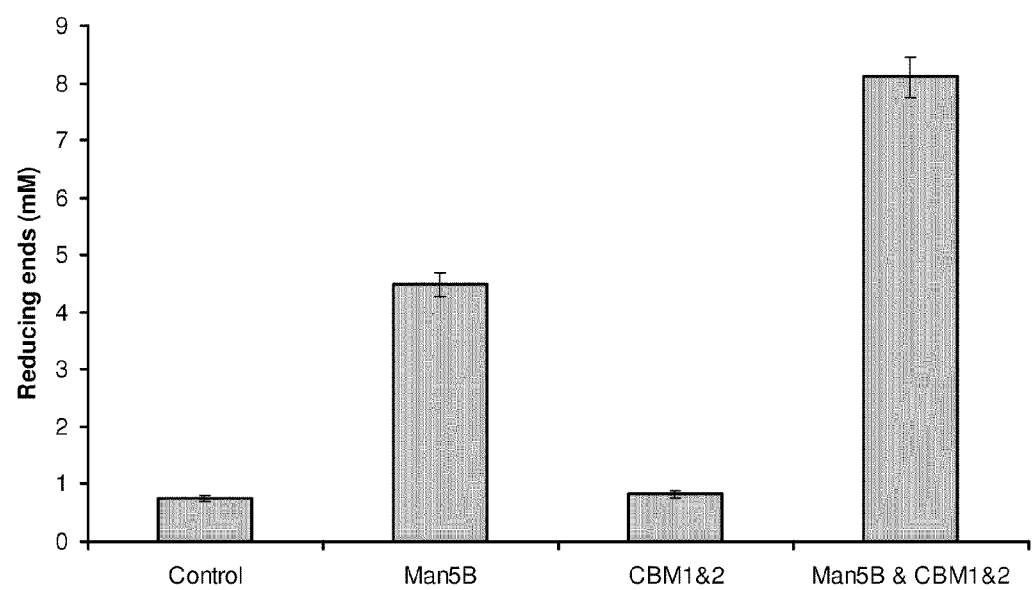
FIG. 8 provides a graph indicating that the hydrolysis of beta-mannan by Man5B was promoted by addition of tandem CBM (CBM1 plus CMB2) from Man5A. Beta mannan (0.5%, w/v) was incubated with CBM1 and CBM2 (final concentration of 50 nM) in citrate buffer (50 mM, pH 5.5) for 60 minutes at 65° C. with rotation (24 rpm). Then Man5B (final concentration of 50 nM) was added, and hydrolysis was continued for another 60 min at 65° C. with rotation (24 rpm). The reaction was terminated by heating at 100° C. for 20 min. The mixture was then centrifuged at 13000 rpm for 10 min. The reducing ends in the supernatant were assayed with the PHBAH method. The experiments were performed in triplicate.
Figure 9:
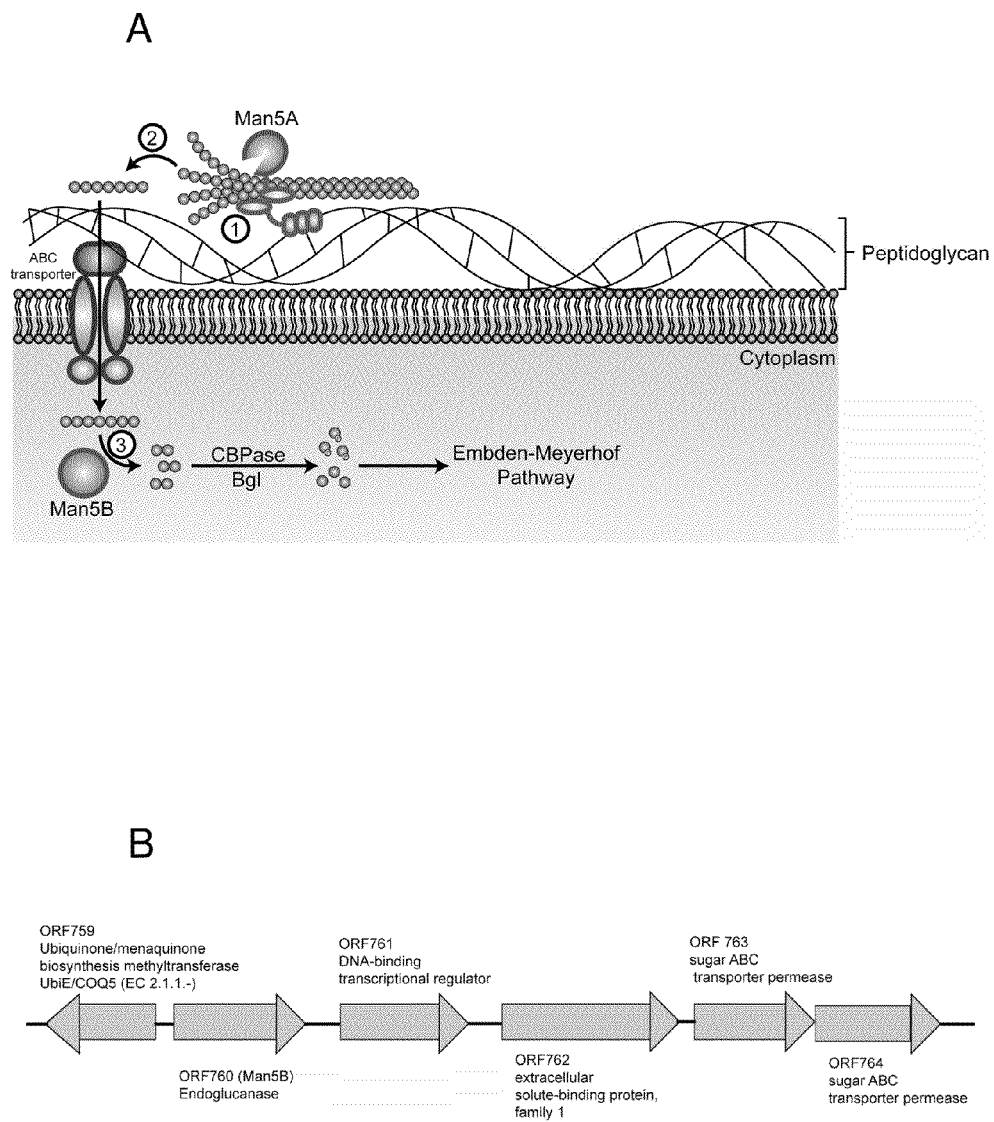
FIG. 9A provides a schematic representation of a mechanism involved in nutrient acquisition from mannan containing polysaccharides by *C. polysaccharolyticus*. Man5A has a signal peptide that allows its transport outside the cell after synthesis inside the cell. The large polypeptide with its three surface layer homology (SLH) domains at the extreme C-terminus is anchored to the peptidoglycan by the SLH repeats of the polypeptide. Upon coming into contact with mannan based polysaccharides, Man5A cleaves the substrate into oligosaccharides that are then transported into the cytoplasm where Man5B cleaves them into disaccharides and monosaccharides for metabolism by *C. polysaccharolyticus*. The genome of the bacterium harbors genes predicted to encode β-glucosidase (Bgl) and cellobiose phosphorylase (CBPase) enzymes, which may be involved in the fermentation of cellobiose.
FIG. 9B provides a schematic of the genomic context of man5B. ORF760 encodes the polypeptide designated Man5B. Genes downstream of man5B are predicted to encode: a DNA-binding transcriptional regulator (ORF0761), an extracellular solute-binding protein (ORF0762), and two permease components of an ABC transport system (ORF0763 and ORF0764). The proximity of these genes to man5B indicates that ORF0762, ORF0763, and ORF0764 encode proteins involved in the transport of mannan containing oligosaccharides.
Figure 10:
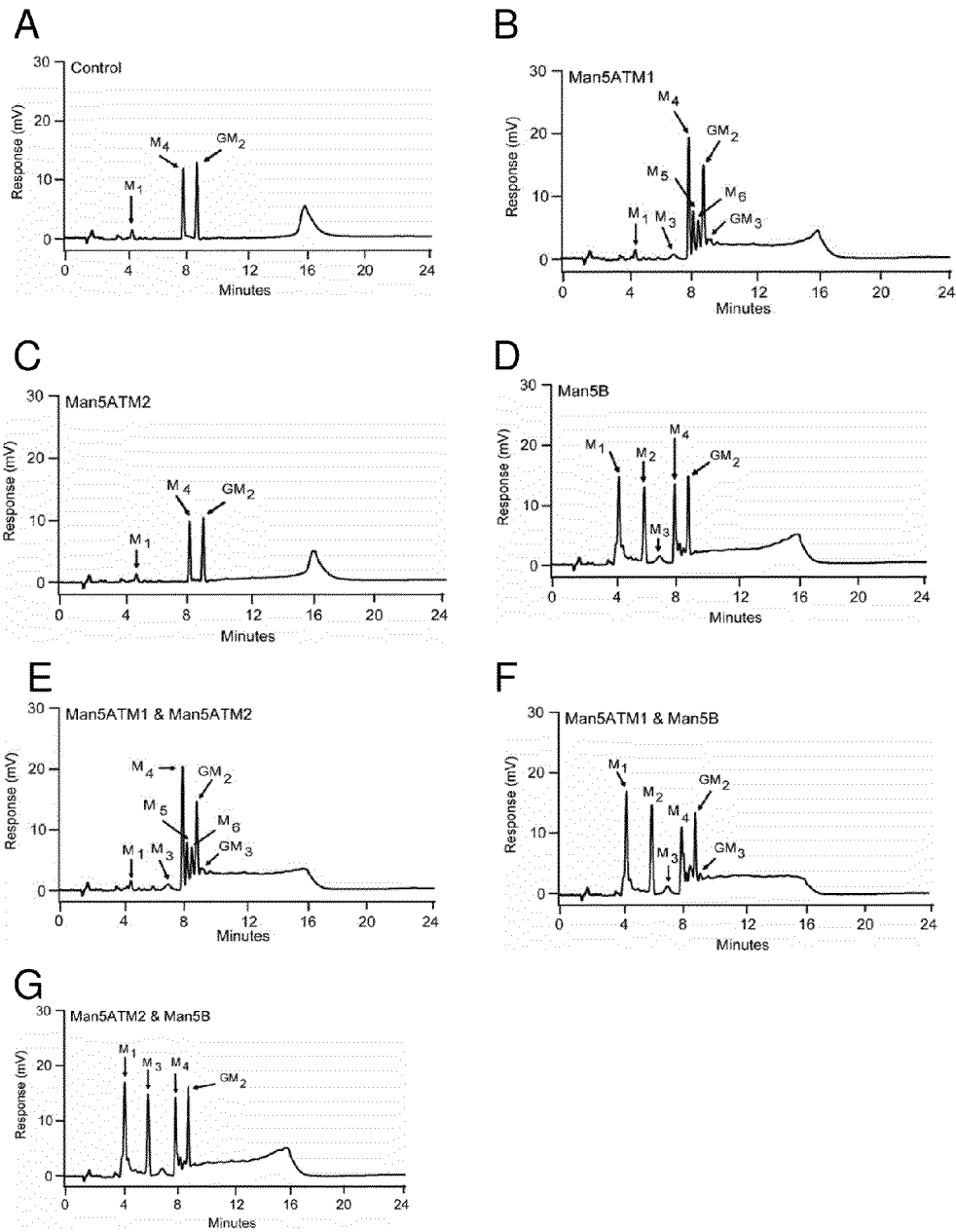
FIGS. 10A-G provides results of HPLC analysis of guar gum hydrolysis by Man5ATM1, Man5ATM2 and Man 5B. In guar gum hydrolysis reactions, the respective enzymes or combinations thereof were incubated with the substrate (0.5% w/v) in citrate buffer (50 mM, pH 5.5) at 65° C. for 1 h. The products were analyzed by HPAEC. For reactions with a single enzyme, the final enzyme concentration was 50 mM and for reactions with two enzymes, the final enzyme concentration was 25 nM of each enzyme. The peaks corresponding to mannose ($M_1$), mannobiose ($M_2$), mannotriose ($M_3$), mannotetraose ($M_4$), mannopentaose ($M_5$), mannohextaose ($M_6$), 1,6-galactosyl mannobiose ($GM_2$) and 1,6-galactosyl mannotriose ($GM_3$) are indicated by arrows.
Figure 11:
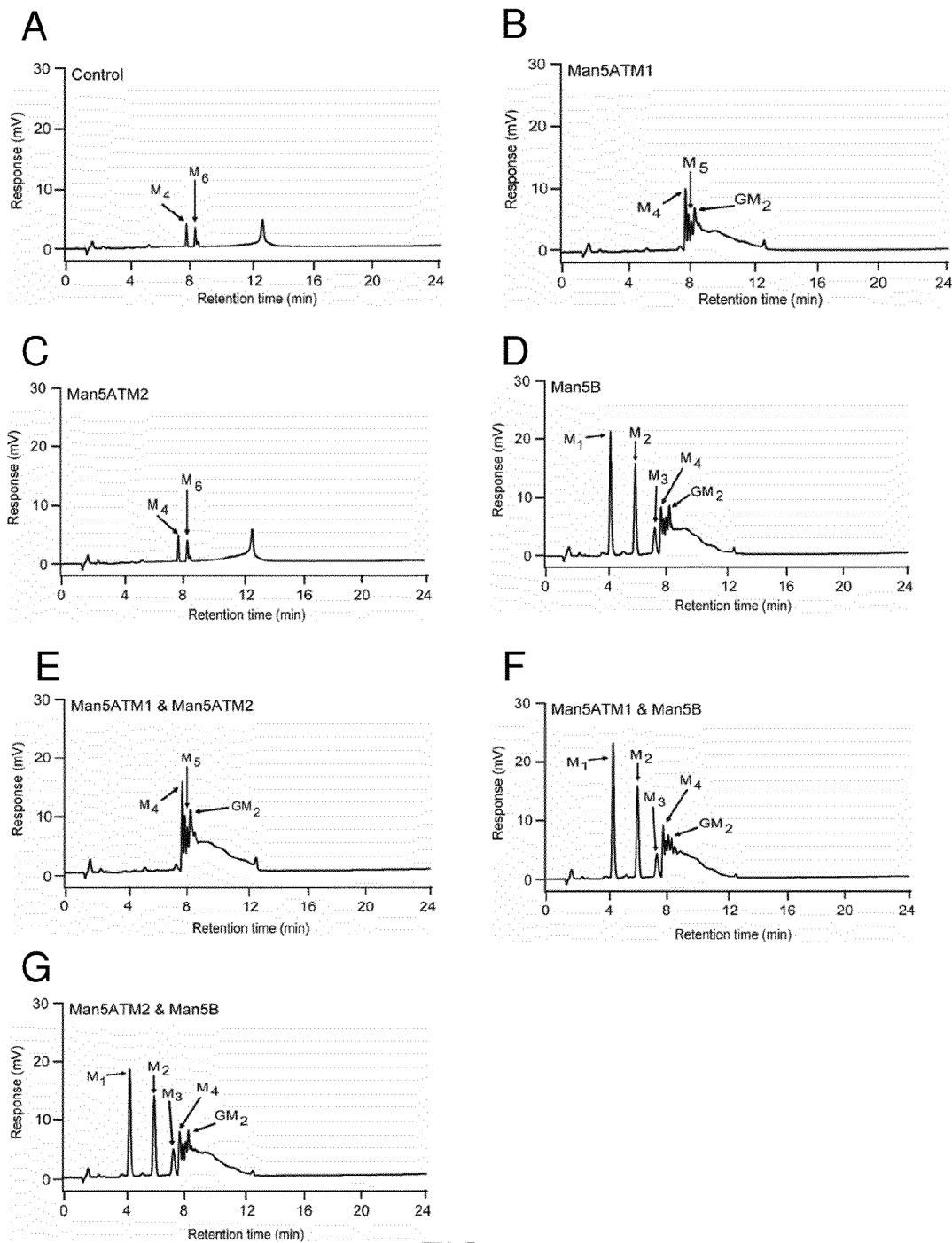
FIGS. 11A-G provides results of HPLC analysis of locust bean gum hydrolysis by Man5ATM1, Man5ATM2 and Man 5B. In locust bean gum hydrolysis reactions, the respective enzymes or combinations thereof were incubated with the substrate (0.5% w/v) in citrate buffer (50 mM, pH 5.5) at 65° C. for 1 h. The products were analyzed by HPAEC. For reactions with a single enzyme, the final enzyme concentration was 50 mM and for reactions with two enzymes, the final enzyme concentration was 25 nM of each enzyme. The peaks corresponding to mannose ($M_1$), mannobiose ($M_2$), mannotriose ($M_3$), mannotetraose ($M_4$), mannopentaose ($M_5$), mannohextaose ($M_6$), and 1,6-galactosyl mannobiose ($GM_2$) are indicated by arrows.
Figure 12:
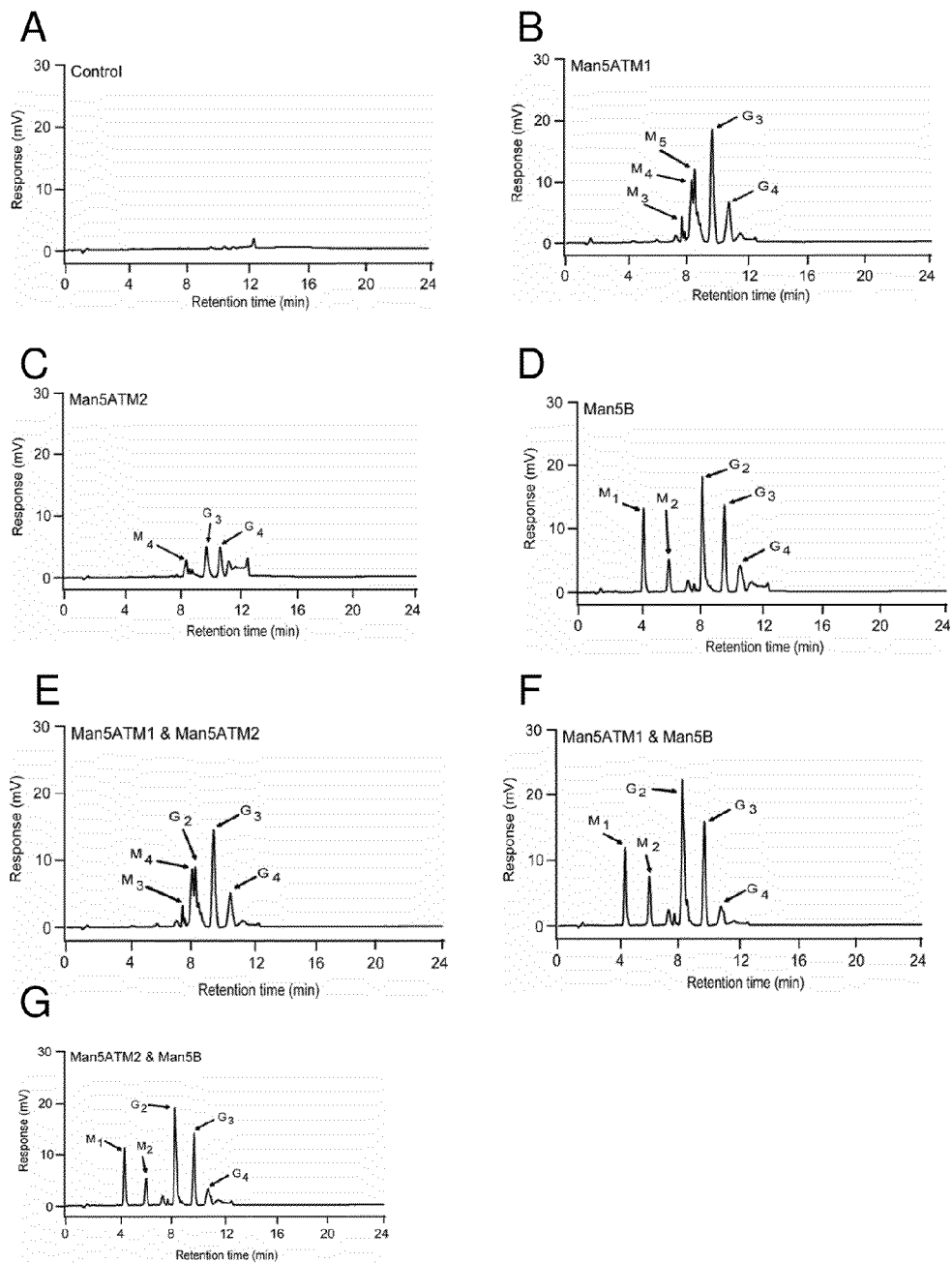
FIGS. 12A-G provides results of HPLC analysis of glucomannan hydrolysis by Man5ATM1, Man5ATM2 and Man 5B. In gluocomannan hydrolysis reactions, the respective enzymes or combinations thereof were incubated with the substrate (0.5% w/v) in citrate buffer (50 mM, pH 5.5) at 65° C. for 1 h. The products were analyzed by HPAEC. For reactions with a single enzyme, the final enzyme concentration was 50 mM and for reactions with two enzymes, the final enzyme concentration was 25 nM of each enzyme. The peaks corresponding to mannose ($M_1$), mannobiose ($M_2$), mannotriose ($M_3$), mannotetraose ($M_4$), mannopentaose ($M_5$), cellobiose ($G_2$), cellotriose ($G_3$) and cellotetraose ($G_4$) are indicated by arrows.
Figure 13:
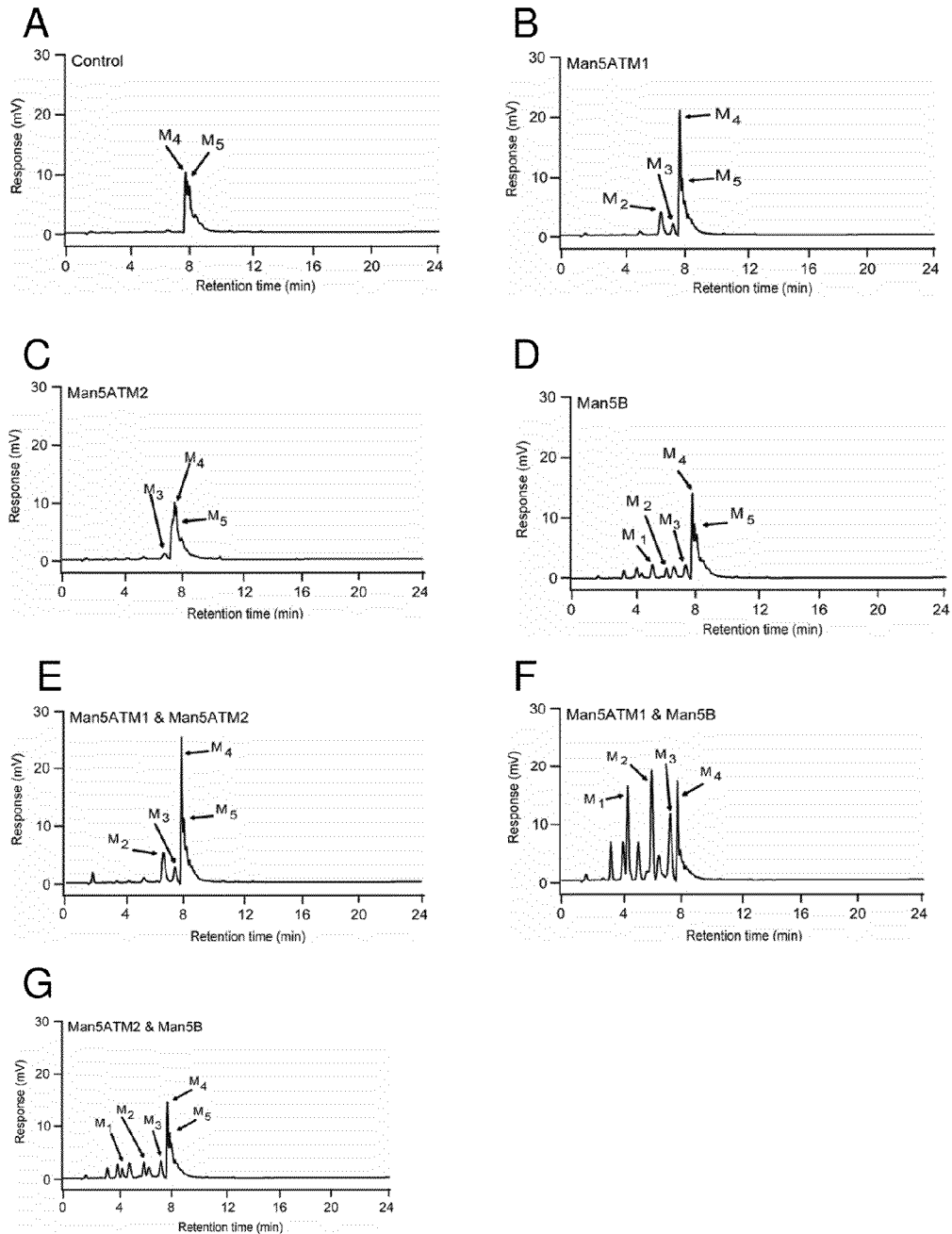
FIGS. 13A-G provides results of HPLC analysis of beta-mannan hydrolysis by Man5ATM1, Man5ATM2 and Man 5B. In beta-mannan hydrolysis reactions, the respective enzymes or combinations thereof were incubated with the substrate (0.5% w/v) in citrate buffer (50 mM, pH 5.5) at 65° C. for 1 h. The products were analyzed by HPAEC. For reactions with a single enzyme, the final enzyme concentration was 50 mM and for reactions with two enzymes, the final enzyme concentration was 25 nM of each enzyme. The peaks corresponding to mannose ($M_1$), mannobiose ($M_2$), mannotriose ($M_3$), mannotetraose ($M_4$), and mannopentaose ($M_5$) are indicated by arrows.

The tandem CBMs of Man5A (CBM1+CBM2) increases release of reducing sugars by Man5B from mannan containing polysaccharides. Carbohydrate binding modules can serve either as motifs that increase the affinity of glycoside hydrolases for the substrates or destabilize the substrate hence increasing the surface area for attack by the catalytic domain. During development of the present disclosure, the tandem CBMs of Man5A were tested for this property. As shown in FIG. 8, adding the protein construct of CBM1+CBM2 to Man5B, leads to release of about twice the amount of reducing sugars compared to Man5B alone, which lacks a CBM in its polypeptide. This experiment only works if the tandem CBM is initially incubated (pre-incubated) with the substrate before addition of the enzyme with the catalytic activity. This indicates that the tandem CBM protein can be added to the mannan containing polysaccharides to increase hydrolysis.

What is claimed is:

1. An isolated protein comprising the amino acid sequence of SEQ ID NO: 31.

2. A composition comprising the isolated protein of claim 1.

3. The composition of claim 2, further comprising a second isolated protein comprising a second amino acid sequence wherein the second amino acid sequence is selected from the group consisting of the amino acid sequence of SEQ ID NO: 27, the amino acid sequence of SEQ ID NO: 28, and the amino acid sequence of SEQ ID NO: 29.

4. A method of converting biomass to sugars comprising contacting the biomass with the composition of claim 2.

5. The method of claim 4, wherein the composition further comprises a second isolated protein comprising a second amino acid sequence wherein the second amino acid sequence is selected from the group consisting of the amino acid sequence of SEQ ID NO: 27, the amino acid sequence of SEQ ID NO: 28, and the amino acid sequence of SEQ ID NO: 29.

6. A method of producing ethanol comprising:
contacting biomass with the composition of claim 2 to yield a sugar solution; and culturing the sugar solution with a fermentative microorganism under conditions sufficient to produce ethanol.

7. The method of claim 6, wherein the composition further comprises a second isolated protein comprising a second amino acid sequence wherein the second amino acid sequence is selected from the group consisting of the amino acid sequence of SEQ ID NO: 27, the amino acid sequence of SEQ ID NO: 28, and the amino acid sequence of SEQ ID NO: 29.

8. The method of claim 4, wherein the biomass comprises a plant material.

9. The method of claim 8, wherein the plant material is selected from the group consisting of Miscanthus, switchgrass, cord grass, rye grass, reed canary grass, common reed, wheat straw, barley straw, canola straw, oat straw, corn stover, soybean stover, oat hulls, sorghum, rice hulls, sugarcane bagasse, corn fiber, Distillers Dried Grains with Solubles (DDGS), Blue Stem, corncobs, pine, willow, aspen, poplar wood, and energy cane.

10. The method of claim 4, wherein the biomass comprises a woody feedstock with a mannan content of at least 2% by weight.

11. The method of claim 6, wherein the contacting is conducted at a temperature between 45 and 80° C.

12. The method of claim 6, wherein the contacting is conducted at a temperature between 60 to 70° C.

13. A method of treating plant material comprising: contacting plant material with the composition of claim 2 to yield a treated plant material.

14. The method of claim 13, wherein the plant material is selected from the group consisting of palm kernel, coconut, konjac, locust bean gum, gum guar, soy beans, barley, oats, flax, wheat, corn, linseed, citrus pulp, cottonseed, groundnut, rapeseed, sunflower, peas, and lupines.

15. A method of textile cleaning comprising: contacting a soiled textile with the composition of claim 2 to yield a clean textile.

16. A method of paper pulp bleaching comprising: contacting paper pulp with the composition of claim 2 to yield bleached paper pulp.

* * * * *